(12) United States Patent
Xu et al.

(10) Patent No.: US 12,246,068 B2
(45) Date of Patent: Mar. 11, 2025

(54) ENZYMATICALLY ACTIVATABLE PEPTIDE-REDOX MODULATOR CONJUGATES AND USE THEREOF

(71) Applicant: BRANDEIS UNIVERSITY, Waltham, MA (US)

(72) Inventors: Bing Xu, Newton, MA (US); Huaimin Wang, Waltham, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 762 days.

(21) Appl. No.: 16/476,183

(22) PCT Filed: Jan. 4, 2018

(86) PCT No.: PCT/US2018/012359
§ 371 (c)(1),
(2) Date: Jul. 5, 2019

(87) PCT Pub. No.: WO2018/129171
PCT Pub. Date: Jul. 12, 2018

(65) Prior Publication Data
US 2020/0023065 A1    Jan. 23, 2020

Related U.S. Application Data

(60) Provisional application No. 62/443,385, filed on Jan. 6, 2017.

(51) Int. Cl.
| | |
|---|---|
| *A61K 47/54* | (2017.01) |
| *A61K 38/00* | (2006.01) |
| *A61K 47/42* | (2017.01) |
| *A61P 35/00* | (2006.01) |
| *C07K 5/107* | (2006.01) |

(52) U.S. Cl.
CPC ............ *A61K 47/548* (2017.08); *A61K 47/42* (2013.01); *A61P 35/00* (2018.01); *C07K 5/1016* (2013.01); *A61K 38/00* (2013.01)

(58) Field of Classification Search
None
See application file for complete search history.

(56) References Cited

U.S. PATENT DOCUMENTS

| | | |
|---|---|---|
| 3,658,600 A | 4/1972 | Pryor et al. |
| 9,408,921 B2 | 8/2016 | Gao et al. |
| 10,093,674 B2 | 10/2018 | Xu |
| 10,232,037 B2 | 3/2019 | Zhao et al. |
| 11,155,576 B2 | 10/2021 | Xu et al. |
| 2008/0108545 A1 | 5/2008 | Eccles et al. |

FOREIGN PATENT DOCUMENTS

| | | |
|---|---|---|
| WO | 2010/151644 A2 | 12/2010 |
| WO | 2012/166705 A2 | 12/2012 |
| WO | 2012/166706 A2 | 12/2012 |
| WO | 2014/074789 A1 | 5/2014 |
| WO | 2015/116242 A1 | 8/2015 |
| WO | 2015/157535 A2 | 10/2015 |
| WO | 2016/138433 A1 | 9/2016 |
| WO | 2017/189996 A1 | 11/2017 |

OTHER PUBLICATIONS

Chen et al. ("Dual-Targeting pro-apoptotic peptide for programmed cancer cell death via specific mitochondria damage" Scientific Reports 3:3468, Dec. 2013).*
Wang et al. ("Integrating Enzymatic Self-Assembly and Mitochondria Targeting for Selectively Killing cancer cells without Acquired drug resistance" J. am. Chem. Soc. Nov. 14, 2016; 138, 16046-16055).*
International Search Report and Written Opinion for corresponding Application No. PCT/US2018/012359 (mailed May 7, 2018).
Melchionna et al., "The Unexpected Advantages of Using D-Amino Acids for Peptide Self-Assembly into Nanostructured Hydrogels for Medicine," Curr. Top Med. Chem. 16(18):2009-2018 (2016).

* cited by examiner

*Primary Examiner* — Julie Ha
*Assistant Examiner* — Tara L Martinez
(74) *Attorney, Agent, or Firm* — Troutman Pepper Locke LLP (Rochester)

(57) ABSTRACT

Disclosed are peptides capable of enzymatically-induced self-assembly to which is conjugated a redox modulator. These peptides are enzymatically responsive hydrogelators, and they can be used to form pericellular hydrogels/nanofibrils upon exposure to target cells that secrete or express a surface bound ectoenzyme having hydrolase activity suitable to induce peptide gelation. These materials, and compositions containing the same, can be used for inhibiting cancer cell migration, inhibiting cancer cell survival, and/or inhibiting cancer cell growth.

18 Claims, 16 Drawing Sheets

Specification includes a Sequence Listing.

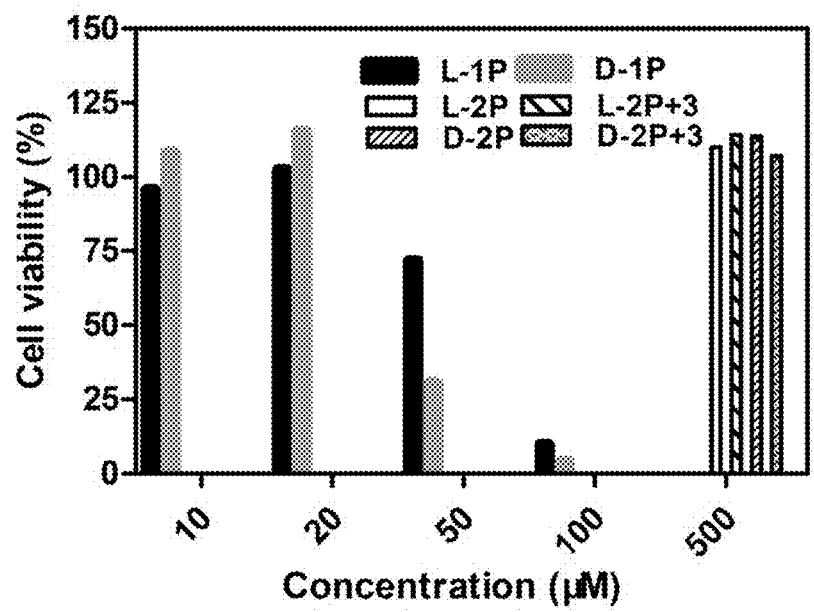
*FIG. 7*
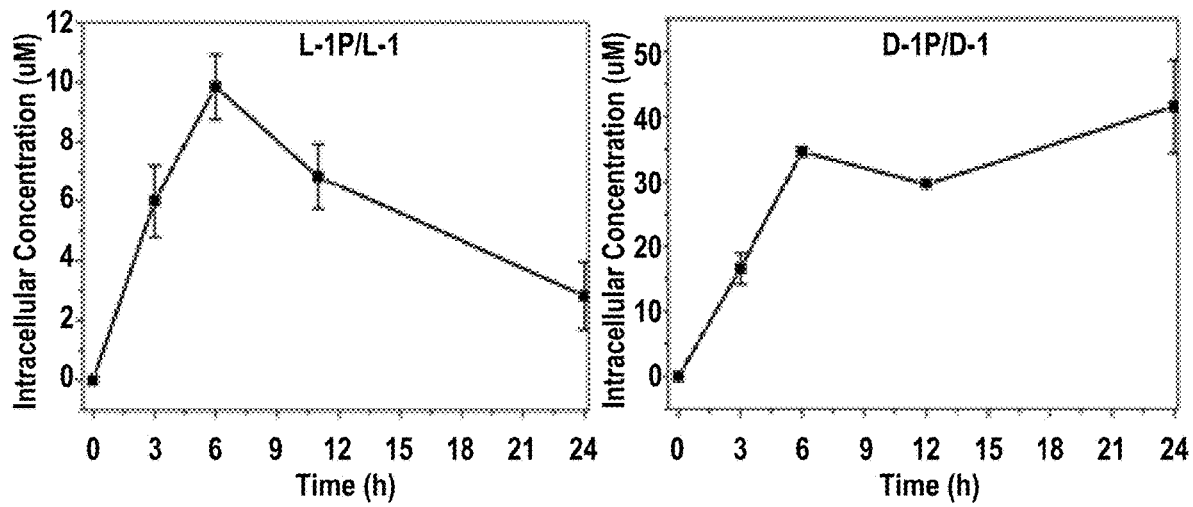
*FIG. 8A*  *Fig. 8B*

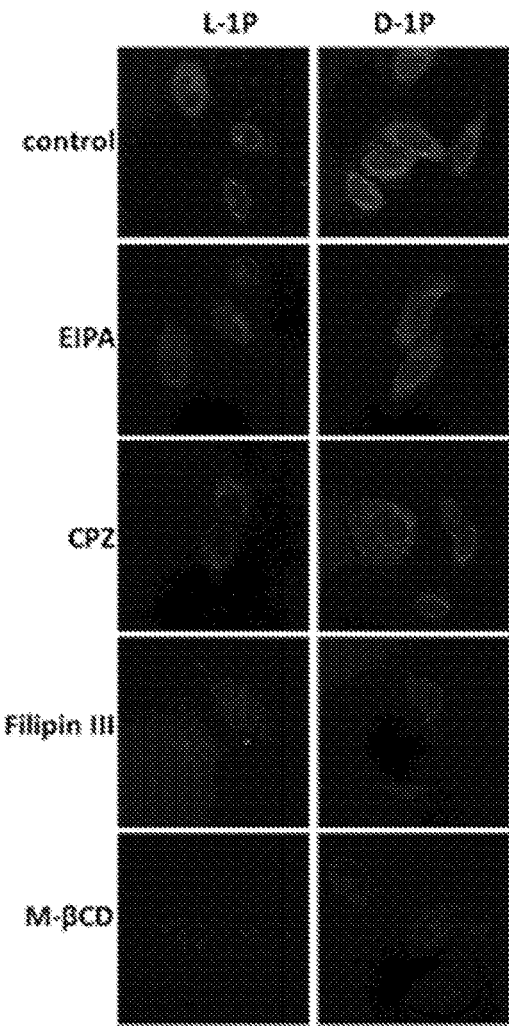
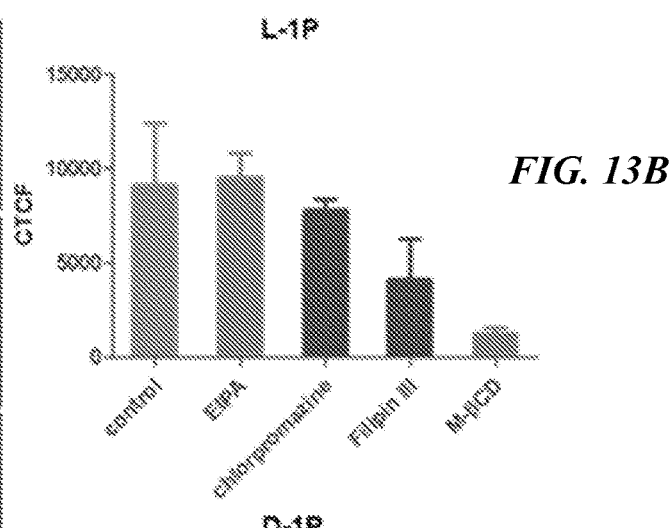
*FIG. 13B*
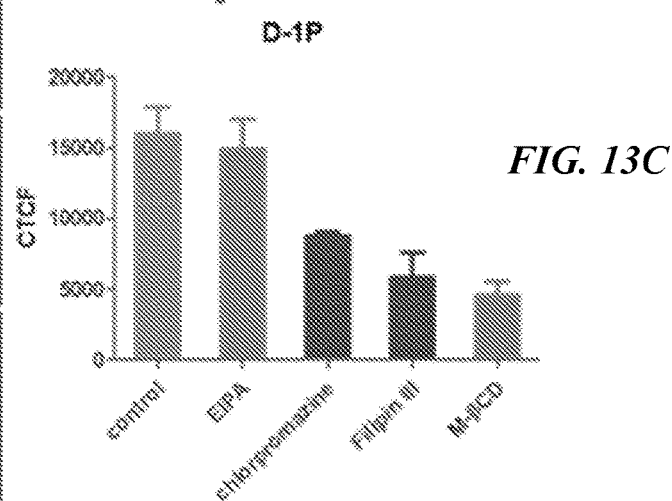
*FIG. 13C*
*FIG. 13A*

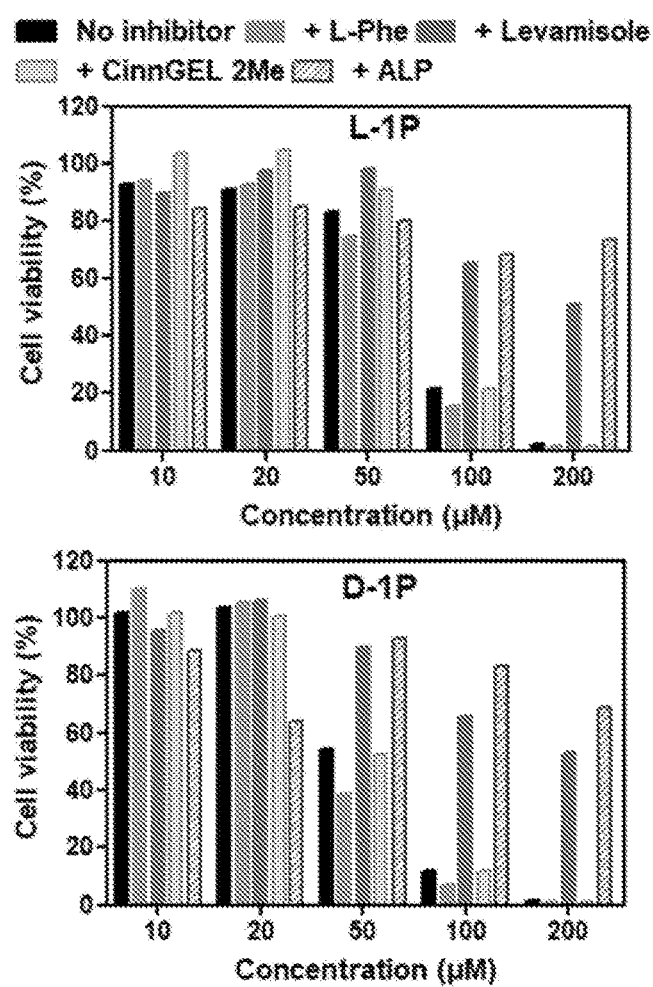
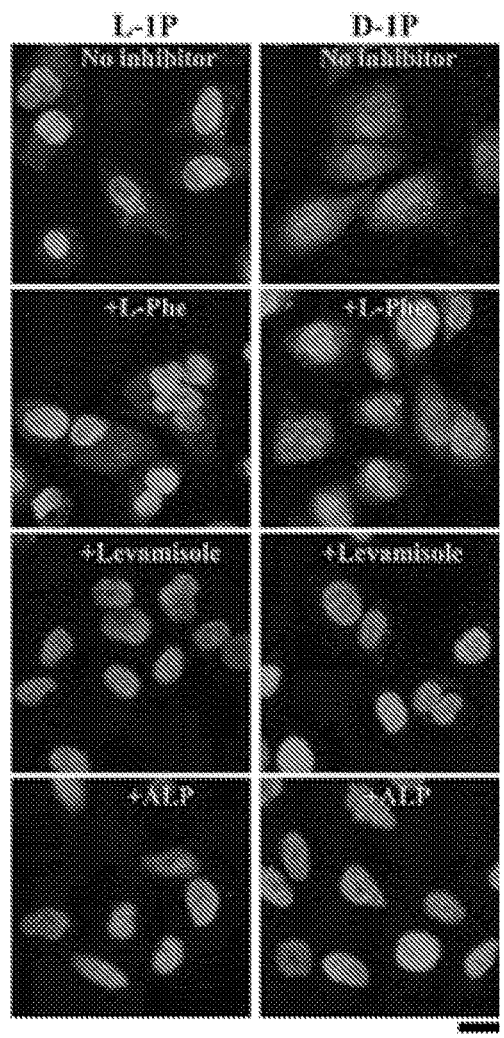
*FIG. 14A*            *FIG. 14B*

SEQUENCE LISTING

```
<160> NUMBER OF SEQ ID NOS: 51

<210> SEQ ID NO 1
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is 4-nitro-2,1,3-
      benzoxadiazolyl-beta-Alanine
<220> FEATURE:
<221> NAME/KEY: MISC_FEATURE
<222> LOCATION: (4)..(4)
<223> OTHER INFORMATION: Xaa at position 4 is phospho-tyrosine or
      tyrosine

<400> SEQUENCE: 1

Xaa Phe Phe Xaa Lys
1               5

<210> SEQ ID NO 2
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine

<400> SEQUENCE: 2

Xaa Phe Xaa Xaa
1

<210> SEQ ID NO 3
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-triphenyl
      phosphinium)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 3

Xaa Phe Xaa Xaa
1
```

```
<210> SEQ ID NO 4
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine

<400> SEQUENCE: 4

Xaa Phe Xaa Xaa
1

<210> SEQ ID NO 5
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-triphenyl
      phosphinium)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 5

Xaa Phe Xaa Xaa
1

<210> SEQ ID NO 6
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine

<400> SEQUENCE: 6

Xaa Phe Xaa Xaa
```

```
<210> SEQ ID NO 7
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 7

Xaa Phe Xaa Xaa
1

<210> SEQ ID NO 8
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine

<400> SEQUENCE: 8

Xaa Phe Xaa Xaa
1

<210> SEQ ID NO 9
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 9
```

```
Xaa Phe Xaa Xaa
1

<210> SEQ ID NO 10
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine

<400> SEQUENCE: 10

Xaa Phe Xaa Xaa
1

<210> SEQ ID NO 11
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 11

Xaa Phe Xaa Xaa
1

<210> SEQ ID NO 12
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine
```

<400> SEQUENCE: 12

Xaa Phe Xaa Xaa
1

<210> SEQ ID NO 13
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 13

Xaa Phe Xaa Xaa
1

<210> SEQ ID NO 14
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine

<400> SEQUENCE: 14

Xaa Phe Xaa Xaa
1

<210> SEQ ID NO 15
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine
<220> FEATURE:
<221> NAME/KEY: MISC_FEATURE
<222> LOCATION: (4)..(4)
<223> OTHER INFORMATION: Xaa at position 4 is phospho-tyrosine

```
<400> SEQUENCE: 15

Xaa Phe Xaa Xaa
1

<210> SEQ ID NO 16
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is phospho-tyrosine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine

<400> SEQUENCE: 16

Xaa Phe Xaa Xaa
1

<210> SEQ ID NO 17
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine
<220> FEATURE:
<221> NAME/KEY: MISC_FEATURE
<222> LOCATION: (4)..(4)
<223> OTHER INFORMATION: Xaa at position 4 is phospho-tyrosine

<400> SEQUENCE: 17

Xaa Phe Xaa Xaa
1

<210> SEQ ID NO 18
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine
      having a C-terminal-di(isopropyloxycarbonyl-oxymethyl)phosphoester

<400> SEQUENCE: 18

Xaa Phe Tyr Xaa
```

-continued

```
<210> SEQ ID NO 19
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 19

Xaa Phe Xaa Xaa
1

<210> SEQ ID NO 20
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine
      having a C-terminal-di(isopropyloxycarbonyl-oxymethyl)phosphoester

<400> SEQUENCE: 20

Xaa Phe Tyr Xaa
1

<210> SEQ ID NO 21
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 21

Xaa Phe Xaa Xaa
1
```

```
<210> SEQ ID NO 22
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine having a C-terminal-di(isopropyloxycarbonyl-
      oxymethyl)phosphoester

<400> SEQUENCE: 22

Xaa Phe Tyr Xaa
1

<210> SEQ ID NO 23
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-triphenyl
      phosphinium)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 23

Xaa Phe Xaa Xaa
1

<210> SEQ ID NO 24
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine having a C-terminal-
      di(isopropyloxycarbonyloxymethyl)phosphoester

<400> SEQUENCE: 24

Xaa Phe Tyr Xaa
1

<210> SEQ ID NO 25
<211> LENGTH: 4
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-triphenyl
      phosphinium)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 25

Xaa Phe Xaa Xaa
1

<210> SEQ ID NO 26
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine having a C-terminal-di(isopropyl-
      oxycarbonyloxymethyl)phosphoester

<400> SEQUENCE: 26

Xaa Phe Tyr Xaa
1

<210> SEQ ID NO 27
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 27

Xaa Phe Xaa Xaa
1

<210> SEQ ID NO 28
```

```
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine having a C-terminal-di(isopropyloxy-
      carbonyloxymethyl)phosphoester

<400> SEQUENCE: 28

Xaa Phe Tyr Xaa
1

<210> SEQ ID NO 29
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 29

Xaa Phe Xaa Xaa
1

<210> SEQ ID NO 30
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine having a
      C-terminal-di(isopropyl-oxycarbonyloxymethyl)phosphoester

<400> SEQUENCE: 30

Xaa Phe Tyr Xaa
1

<210> SEQ ID NO 31
<211> LENGTH: 4
<212> TYPE: PRT
<213> ORGANISM: Artificial
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl) phosphoester

<400> SEQUENCE: 31

Xaa Phe Xaa Xaa
1

<210> SEQ ID NO 32
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine having a
      C-terminal-di(isopropyloxycarbonyloxymethyl)phosphoester

<400> SEQUENCE: 32

Xaa Phe Tyr Xaa
1

<210> SEQ ID NO 33
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine
<220> FEATURE:
<221> NAME/KEY: MISC_FEATURE
<222> LOCATION: (4)..(4)
<223> OTHER INFORMATION: Xaa at position 4 is tyrosine having a
      C-terminal-di(isopropyloxycarbonyloxymethyl)-phosphoester

<400> SEQUENCE: 33

Xaa Phe Xaa Xaa
1

<210> SEQ ID NO 34
<211> LENGTH: 4
<212> TYPE: PRT
```

```
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine

<400> SEQUENCE: 34

Xaa Phe Tyr Xaa
1

<210> SEQ ID NO 35
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-triphenyl
      phosphinium)-lysine

<400> SEQUENCE: 35

Xaa Phe Xaa Tyr
1

<210> SEQ ID NO 36
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-triphenyl
      phosphinium)-lysine

<400> SEQUENCE: 36

Xaa Phe Tyr Xaa
1

<210> SEQ ID NO 37
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
```

```
<222> LOCATION: (3)..(3)
<223> OTHER INFORMATION: Xaa at position 3 is (epsilon-triphenyl
      phosphinium)-lysine

<400> SEQUENCE: 37

Xaa Phe Xaa Tyr
1

<210> SEQ ID NO 38
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine

<400> SEQUENCE: 38

Xaa Phe Tyr Xaa
1

<210> SEQ ID NO 39
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine

<400> SEQUENCE: 39

Xaa Phe Xaa Tyr
1

<210> SEQ ID NO 40
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-
      phthalazinedione)-lysine

<400> SEQUENCE: 40

Xaa Phe Tyr Xaa
1
```

-continued

```
<210> SEQ ID NO 41
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-
      phthalazinedione)-lysine

<400> SEQUENCE: 41

Xaa Phe Xaa Tyr
1

<210> SEQ ID NO 42
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine

<400> SEQUENCE: 42

Xaa Phe Tyr Xaa
1

<210> SEQ ID NO 43
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine

<400> SEQUENCE: 43

Xaa Phe Xaa Tyr
1

<210> SEQ ID NO 44
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
```

N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is
      (epsilon-N,N'-diethylaminotriphenylmethane)-lysine

<400> SEQUENCE: 44

Xaa Phe Tyr Xaa
1

<210> SEQ ID NO 45
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is
      (epsilon-N,N'-diethylaminotriphenylmethane)-lysine

<400> SEQUENCE: 45

Xaa Phe Xaa Tyr
1

<210> SEQ ID NO 46
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine

<400> SEQUENCE: 46

Xaa Phe Tyr Xaa
1

<210> SEQ ID NO 47
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is naphthyl-acetyl-
      phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine

<400> SEQUENCE: 47

Xaa Phe Xaa Tyr
1

```
<210> SEQ ID NO 48
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (4)..(4)
<223> OTHER INFORMATION: Xaa at position 4 is (epsilon-porphyrin)-lysine

<400> SEQUENCE: 48

Xaa Phe Tyr Xaa
1

<210> SEQ ID NO 49
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is
      N-(4-nitro-2,1,3-benzoxadiazolylacetyl)phenylalanine
<220> FEATURE:
<221> NAME/KEY: MISC_FEATURE
<222> LOCATION: (3)..(3)
<223> OTHER INFORMATION: Xaa at position 3 is (epsilon-porphyrin)-lysine

<400> SEQUENCE: 49

Xaa Phe Xaa Tyr
1

<210> SEQ ID NO 50
<211> LENGTH: 4
<212> TYPE: PRT
<213> ORGANISM: Artificial
<220> FEATURE:
<223> OTHER INFORMATION: Synthetic peptide

<400> SEQUENCE: 50

Phe Phe Tyr Lys
1

<210> SEQ ID NO 51
<211> LENGTH: 4
<212> TYPE: PRT
<213> ORGANISM: Artificial
<220> FEATURE:
<223> OTHER INFORMATION: Synthetic peptide

<400> SEQUENCE: 51

Phe Phe Lys Tyr
1
```

US 12,246,068 B2

ENZYMATICALLY ACTIVATABLE PEPTIDE-REDOX MODULATOR CONJUGATES AND USE THEREOF

This application is a national stage application under 35 U.S.C. § 371 of PCT Application No. PCT/US2018/012359, filed Jan. 4, 2018, which claims the benefit of U.S. Provisional Patent Application Ser. No. 62/443,385, filed Jan. 6, 2017, which is hereby incorporated by reference in its entirety.

This invention was made with government support under R01CA142746 awarded by the National Institutes of Health. The government has certain rights in this invention.

This application contains a computer readable Sequence Listing, which has been submitted electronically in TXT format and is hereby incorporated by reference in its entirety. Said TXT copy, created on Sep. 19, 2023, is named Revised_Sequence_Listing_147376_00362_ST25.txt and is 22,707 bytes in size.

BACKGROUND OF THE INVENTION

Molecular-targeted therapeutics, which are mostly based on ligand-receptor interaction or enzyme inhibition of a specific target, have been a key strategy for developing anticancer drugs. However, recent advances in cancer biology have revealed the great complexity of cancers (Hanahan et al., *Cell* 144:646 (2011)), such as redundant signaling pathways (Stommel et al., *Science* 318:287 (2007); Thornberry et al., *J. Biol. Chem.* 272:17907 (1997)), acquired drug resistance (Hayes et al., *Crit. Rev. Biochem. Mol. Biol.* 30:521 (1995)), genomic instability (Campbell et al., *Nature* 467:1109 (2010); Negrini et al., *Nat. Rev. Mol. Cell Biol.* 11:220 (2010)), intratumoral heterogeneity (Patel et al., *Science* 344:1396 (2014); Campbell et al., *Cell Cycle* 6:2332 (2007)), and tumor microenvironment (Mantovani et al., *Nature* 454:436 (2008); Vaupel et al., *Cancer Res.* 49:6449 (1989)). These conceptual advances not only elucidate the mechanism of the drug resistance of the current chemotherapy that aims at only one or two molecular targets (e.g., enzymes, receptors, or transcription factors), but also underscore an urgent need of new approaches for cancer therapy. Contrasting to targeting a specific enzyme or protein, targeting a subcellular organelle or antagonizing an essential protein in organelle represent a unique approach for killing cancer cells (Murphy, M. P. *Biochim. Biophys. Acta, Bioenerg.* 1777:1028 (2008)) without inducing drug resistance. Because the release of cytochrome c (Cyt c) from mitochondria is a major event in intrinsic cell death signaling pathway (Liu et al., *Cell* 86:147 (1996); Luo et al., *Cell* 94:481 (1998)), targeting mitochondria (Kang et al., *Cell* 131:257 (2007); Chevalier et al., *J. Am. Chem. Soc.* (2016)) (e.g., modulating the redox potential of mitochondria (Green et al., *Science* 281:1309 (1998))) to induce the death of cancer cells may be advantageous over the specific ligand-receptor interaction in countering drug resistance in cancer therapy (Kang et al., *Cell* 131:257 (2007)).

Since the report by Murphy et al. that triphenyl phosphinium (TPP) is a facile molecular motif for targeting the mitochondrial matrix (Burns et al., *Arch. Biochem. Biophys.* 322:60 (1995)), considerable research activities have focused on targeting mitochondria (Yasueda et al., *J. Am. Chem. Soc.* (2016); Zha et al., *Science* 290:1761 (2000); Weinberg et al., *Nat. Chem. Biol.*, 11:9 (2015); Wang et al., *Nat. Med.* 17:71 (2011); Fulda et al., *Nat. Rev. Drug Discovery*, 9:447 (2010)). For example, attachment of bioactive molecules or therapeutic agents to TPP is the most facile and explored strategy (Fulda et al., *Nat. Rev. Drug Discovery*, 9:447 (2010)), which endow the resulted molecules with targeting and enhanced activity, even against drug resistant cancer (Armstrong, J., *Br. J. Pharmacol.* 151:1154 (2007); Marrache et al., *Proc. Natl. Acad. Sci. U.S.A* 111:10444 (2014)). One prominent example is gamitrinib, a HSP90 inhibitor designed to target the mitochondria of human cancer cell (Kang et al., *J. Clin. Invest.* 119:454 (2009)) because the essential role of HSP90 in the survival of cancer cells (Hendrick et al., *Annu. Rev. Biochem.* 62:349 (1993); Whitesell et al., *Nat. Rev. Cancer,* 5:761 (2005)). Similar strategy also applied to other anticancer drugs, which show activity in mitochondria (Fulda et al., *Nat. Rev. Drug Discovery,* 9:447 (2010); D'Souza et al., *Biochimica et Biophysica Acta (BBA)-Bioenergetics* 1807:689 (2011)). Besides TPP, mitochondria penetrating peptides constitute another promising candidate explored for modulating the intracellular distribution of bioactive molecules (Horton et al., *Chem. Biol.* 15:375 (2008); Yousif et al., *ChemBioChem* 10:2081 (2009); Jean et al., *Acc. Chem. Res.* (2016)). Although these preclinical studies indicate that targeting an organelle (e.g., mitochondria) or a nodal protein (e.g., HSP90) in multiple signaling networks is a promising approach for killing cancer cells without inducing drug resistance, they still suffer drawbacks and remain to be improved. In particular, the targeted organelles or nodal proteins also are critical to the functions of normal cells. Moreover, if the antagonist of a nodal protein is based on specific ligand-receptor interaction, drug resistance still may emerge due to the mutation of the receptors. Therefore, there remains an unfulfilled need to develop novel approaches that are multiple-targeting and minimize the emergence of drug resistance (Wang et al., *J. Am. Chem. Soc.* 138:10758-10761 (2016)).

It would be desirable, therefore, to provide a therapeutic agent that can selectively target cancer cells using a mode of action that resists the emergence of drug resistance. The present invention overcomes these and other deficiencies in the art.

SUMMARY OF THE INVENTION

A first aspect of the invention relates to a peptide capable of enzymatically-induced self-assembly to which is conjugated a redox modulator.

In certain embodiments, the peptide comprises up to about 35 amino acids, including a plurality of aromatic amino acid residues and either (i) an amino acid residue that is phosphorylated or sulfated, or (ii) a phosphoester moiety, or both (i) and (ii), wherein, upon exposure to a cell that expresses an ectoenzyme that hydrolyzes the phosphate group, the sulfate group, or the phosphoester moiety, the peptide self-assembles to form nanofibrils externally of the cell. In certain embodiments, the peptide also includes a fluorophore conjugated to the peptide.

Also encompassed by this aspect of the invention are enzymatically activated peptide-redox modulator conjugates, and supramolecular hydrogels and/or nanofibrils formed upon self-assembly of the enzymatically activated peptides.

A second aspect of the invention relates to a pharmaceutical composition comprising a pharmaceutically acceptable carrier and a peptide-redox modulator conjugate according to the first aspect of the invention. One or more structurally distinct peptides can be included in the composition.

A third aspect of the invention relates to a method for forming a nanofibril network on or near the surface of target cells. This method involves contacting a target cell that expresses a cell surface-bound enzyme having hydrolytic (hydrolase) activity, secretes an enzyme having hydrolytic (hydrolase) activity, or both, with the peptide-redox modulator conjugate according to the first aspect of the invention or the pharmaceutical composition according to the second aspect of the invention, wherein said contacting is effective to hydrolyze the phosphate group, the sulfate group, or the phosphoester moiety and cause in situ self-assembly of the peptides to form a nanofibril network on or near the surface of the target cell.

A fourth aspect of the invention relates to a method for treating a cancerous condition in a subject. This method involves administering to a subject having a cancerous condition a therapeutically effective amount of the peptide-redox modulator conjugate according to the first aspect of the invention or the pharmaceutical composition according to the second aspect of the invention, wherein said administering is effective to hydrolyze the phosphate group, the sulfate group, or the phosphoester moiety and cause in vivo self-assembly of the peptides to form a nanofibril network on or near the surface of cancer cells.

The examples show enzyme-instructed self-assembly ("EISA"), a bioinspired molecular process, selectively generates assemblies of peptide-redox modulator (e.g., triphenyl phosphinium ("TPP")) conjugates in the pericellular space of cancer cells for uptake, which allows selectively targeting the mitochondria of cancer cells. The attachment of TPP to a pair of enantiomeric, phosphorylated peptides produces the precursors (L-1P or D-1P) that form oligomers. Upon dephosphorylation catalyzed by ectophosphatases (e.g., alkaline phosphatase ("ALP")) overexpressed on cancer cells (e.g., Saos2), the oligomers self-assemble to form nanoscale assemblies only on the surface of the cancer cells. The cancer cells uptake these assemblies of TPP-peptide conjugates via endocytosis, mainly via caveolae/raft dependent pathway. Inside the cells, the assemblies of TPP-peptide conjugates escape from lysosome, induce dysfunction of mitochondria to release cytochrome c, and result in cell death, while the controls (i.e., omitting TPP motif, inhibiting ALP, or removing phosphate trigger) hardly kill the Saos2 cells. Most importantly, the repeated stimulation of the cancer cells by the precursors unexpectedly sensitizes the cancer cells to the precursors. As the first example of the integration of subcellular targeting with cell targeting, this study validates the spatial control of the assemblies of non-specific cytotoxic agents by EISA as a promising molecular process for selectively killing cancer cells without inducing acquired drug resistance. Thus, the peptide-redox modulator conjugates of the invention afford cancer cell-specific uptake and, thus, targeted delivery of the redox modulator to cancer cells, where the redox modulator can interfere with cancer cell survival, migration, and/or growth.

BRIEF DESCRIPTION OF THE DRAWINGS

FIG. 7 is a graph showing the viability of Saos2 cells after being incubated with L-1P, D-1P, L-2P, D-2P, L-2P+3, or D-2P+3 for 48 h.

FIGS. 8A-B are graphs showing the time dependent intracellular concentration of L-1P/L-1 (FIG. 8A) or (D-1P/D-1 (FIG. 8B)) inside/outside of Saos2 cell lines. The incubating concentration of L-1P or D-1P is 50 μM.

FIG. 13A shows CLSM images (in color versions, green represents the fluorescence of NBD at excitation of 488 nm) and the corrected total cell fluorescence (CTCF, quantified from the gray scale of CLSM images) of Saos-2 cells treated with L-1P or D-1P (50 μM) for 1 h in the absence (control) or presence of the inhibitors EIPA (100 ethyl-isopropyl-amiloride), CPZ (30 chlorpromazine), Filipin III (5 μg/mL) and M-βCD (5 mM). Scale bar is 15 μm. FIGS. 13B-C are graphs illustrating the CTCF measurements following the L-1P or D-1P treatment in the absence or presence of the recited inhibitors.

FIG. 14A is a pair of graphs showing cell viability of Saos2 cell line treated by L-1P or D-1P (50 μM) in the presence of L-Phenylalanine phosphatase inhibitors (levamisole or CinnGEL Me) or exogenous ALP for 48 h. FIG. 14B shows CLSM images (in color versions, green represent the fluorescence of NBD at excitation of 488 nm and blue represent the fluorescence of Hoechst 3342 to stain cellular nucleus) of Saos2 cells treated with L-1P or D-1P (50 μM) for 4 h in the absence or presence of phosphatase inhibitors or exogenous ALP. The scale bar is 10 μm. [L-Phe]= [levamisole]=1 mM, CinnGEL 2Me=2 [ALP]=10 U/mL.

DETAILED DESCRIPTION OF THE INVENTION

Figure 1:
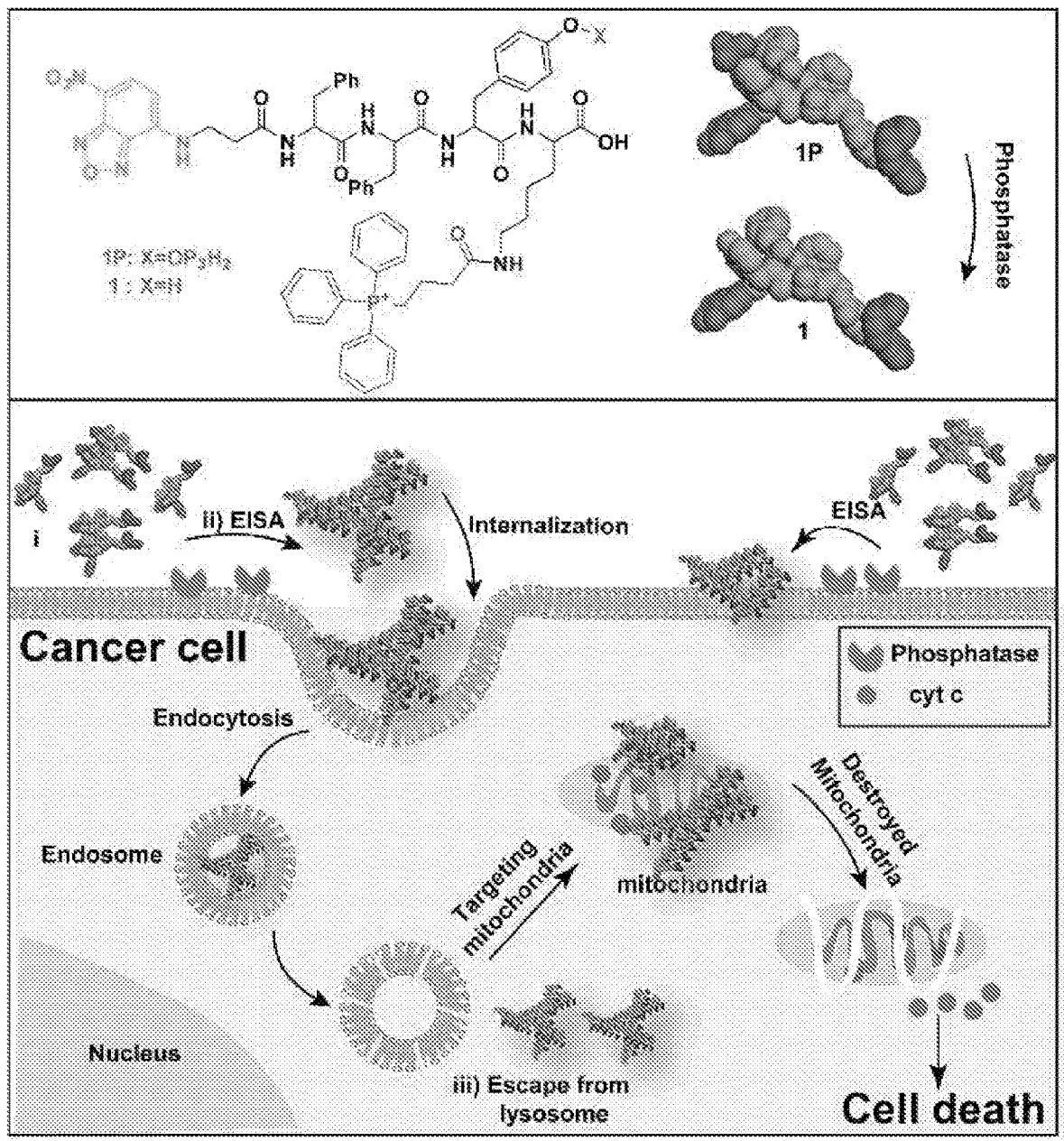
FIG. 1 shows an illustration of enzyme-instructed self-assembly for targeting mitochondria and inducing death of cancer cell.

A first aspect of the invention relates to a peptide capable of enzymatically-induced self-assembly ("EISA") to which is conjugated a redox modulator. This is referred to herein as a peptide-redox modulator conjugate.

The peptide component is substantially innocuous to normal cells (i.e., has low cytotoxicity below 500 μM), but upon exposure to cellular enzymes, particularly ectoenzymes, on the surface of or expressed by target cells, the peptides self-assemble into nanofibrils or nanonets on the surface of target cells. Exemplary ectoenzymes include, without limitation, phosphatases, sulfatases, and peptidases (esterases), particularly those having hydrolytic (hydrolase) activity.

In accordance with certain embodiments of the invention, the peptide component is preferably one that contains up to about 35 amino acids, including a plurality of aromatic amino acid residues and either (i) an amino acid residue that is phosphorylated or sulfated, or (ii) an amino acid comprising a covalently bonded phosphoester moiety, or both (i) and (ii), wherein, upon exposure to a cell that expresses an ectoenzyme that hydrolyzes the phosphate group, the sulfate group, or the phosphoester moiety, the peptide self-assembles to form nanofibrils externally of the cell.

Target cells that can be covered by the nanofibrils/nanonets include cells that express or secrete the ectoenzyme. Exemplary target cells include without limitation, cancer cells, mammalian progenitor cells, virus-infected cells, bacterial pathogens, protozoa, and fungi.

As used herein, the term "nanofibril" is defined as a fiber of material having any shape wherein at least one dimension, e.g. the diameter, width, thickness, and the like, is about 100 nm or less. Nanofibril diameters may be about 50 nm or less, about 40 nm or less, about 30 nm or less, about 20 nm or less, about 10 nm or less, about 5 nm or less, about 4 nm or less, about 3 nm or less, about 2 nm or less, or about 1 nm or less in diameter. Although a hydrogelator upon self-assembly, as described herein, forms nanofibrils, persons of skill in the art should appreciate that such a hydrogelator may also form microfibrils that are larger than 100 nm thick.

As used herein, the term "nanonet" or "nanonets" is defined as a three-dimensional assembly of nanofibrils. As used herein, the term "nanonet(s)" does not preclude the assembly from containing a portion of fibrils that are larger than 100 nm thick.

Peptide nanofibril self-assembly occurs both in vivo and ex vivo. Nanofibrils and nanonets have the capacity to physically alter the target cells and their interactions with the cellular microenvironment. Use of these peptides, and compositions thereof, is contemplated for the treatment of patients with cancerous or precancerous conditions, as well as for the inhibition of target/cancer cell migration, inhibiting target/cancer cell survival, and inhibiting target/cancer cell growth.

In one embodiment, the aromatic amino acids used in the peptides include natural and/or non-natural aromatic amino acid residues such as, without limitation, any one or more of phenylalanine, phenylalanine derivatives, tyrosine, tyrosine derivatives, tryptophan, and tryptophan derivatives. Any known or hereinafter developed phenylalanine derivatives, tyrosine derivatives, or tryptophan derivatives can be used in the present invention, as long as the derivatives facilitate self-assembly of the nanofibrils. Exemplary derivatives of these amino acids include the addition of one or more ring substituents.

The peptides can include all D-amino acids, all L-amino acids, or a mixture of L-amino acids and D-amino acids. In preferred embodiments, the peptide includes only D-amino acids or a mixture of D-amino acids and L-amino acids where the D-amino acid content is greater than 50%, 60%, 70%, 80%, 90%, or 95%.

As a consequence of utilizing entirely D-amino acids or a high proportion of D-amino acids, it is possible to render the peptide component protease resistant, e.g., resistant to proteinase K digestion.

In certain embodiments, a phosphorylated amino acid residue is present in the peptide without any other moiety to inhibit self-assembly. Alternatively, the peptide can include both the phosphorylated amino acid residue and an amino acid residue comprising a phosphoester moiety linked via peptide bond (to said residue). Exemplary amino acid residues that are readily phosphorylated and catalytically dephosphorylated by an enzyme possessing hydrolase activity include, without limitation, serine, threonine, tyrosine, and histidine.

In certain embodiments, a sulfated amino acid residue is present in the peptide without any other moiety to inhibit self-assembly. Alternatively, the peptide can include both the sulfated amino acid residue and an amino acid residue comprising a phosphoester moiety linked via peptide bond (to said residue). Exemplary amino acids residues that are readily sulfated and catalytically desulfated by an enzyme possessing hydrolytic activity include, without limitation, serine, threonine, tyrosine, and hydroxyproline.

In certain embodiments, the peptide does not possess a phosphorylated or sulfated amino acid residue, but instead includes only the amino acid conjugated to a phosphoester moiety linked via peptide bond. In this and the preceding embodiments, the amino acid residue to which a phosphoester moiety is linked can be any amino acid, whether or not the amino acid contains an aromatic side chain. In these embodiments, the phosphoester moiety can be any ester-containing compound that also possesses a primary amino group that can react with the C-terminal carboxylic acid to form a peptide bond. Suitable ester moieties include, without limitation, 4-(2-aminoethyl)-4-oxobutanoic acid; 5-aminovaleric acid; 4-[(8-aminooctyl)amino]-4-oxobutanoic acid; 4-[(5-amino-1-oxopentyl)amino]butanoic acid; and 4-[(5-aminopentyl)amino]-4-oxobutanoic acid.

In certain embodiments, the peptide possess phosphoester and phosphoamidate group. Suitable phosphoester and phosphoamidate groups that can be used in accordance with the present invention include monoesters, symmetrical or usymetrical diesters, mono amidates, symmetrical or unsymmetrical di-amidates, and mixed ester-amides:

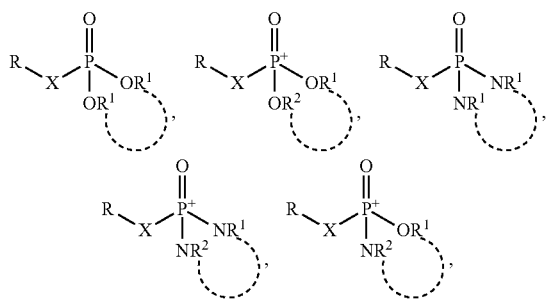

where X is O, R is peptide, $R^1$ and $R^2$ are each independently selected from the group consisting of: H, optionally substituted alkyl, optionally substituted aryl, optionally substituted aryl, optionally substituted heteroaryl (see Wiemer, "Prodrugs of Phosphonates and Phosphates: Crossing the Membrane Barrier," Top Curr. Chem. 360: 115-160 (2015), which is hereby incorporated by reference in its entirety). Suitable phosphoesters include, without limitation, pivaloylmethyl (POM) derivatives, isopropyloxycarbonyloxymethyl (POC) derivatives, S-acylthioalkyl ester (SATE) derivatives, and cycloSal derivatives (see Wiemer, "Prodrugs of Phosphonates and Phosphates: Crossing the Membrane Barrier," Top Curr. Chem. 360: 115-160 (2015), which is hereby incorporated by reference in its entirety). Suitable phosphoamidates include, without limitation, those described in Wiemer, "Prodrugs of Phosphonates and Phosphates: Crossing the Membrane Barrier," Top Curr. Chem. 360: 115-160 (2015), which is hereby incorporated by reference in its entirety. Suitable mixed ester-amides include, without limitation, amidate/phenyl ester, amidate/naphthyl ester, and amidate/alkyl ester (see Wiemer, "Prodrugs of Phosphonates and Phosphates: Crossing the Membrane Barrier," Top Curr. Chem. 360: 115-160 (2015), which is hereby incorporated by reference in its entirety).

In each of the preceding embodiments, the peptide may optionally include an N-terminal amino acid capped by a capping moiety. The capping moiety preferably includes an acyl group due to the reaction of a carboxylic acid with the N-terminal amino group to form a peptide bond.

The capping moiety may or may not include an aromatic or heteroaromatic group. Exemplary capping moieties include, without limitation, alkylacyls such as acetyl, proprionyl, or fatty acid derivatives, or an arylacyl such as 2-naphthalacetyl or 3-((7-nitrobenzo(c)-1,2,5-oxadiazol-4-yl)amino)proprionyl, or heteroarylacyls such as an acylated nucleoside. These capping moieties can protect against enzymatic degradation of the peptide, as well as promote self-assembly in the case where aromatic groups are present in the capping moiety.

Exemplary nucleobases include, without limitation, thyminyl, uracilyl, cytosinyl, adeninyl, and guaninyl. These nucleobases are preferably acylated, e.g., acetyl, proprionyl, etc.

In certain embodiments, the capping moiety may or may not include a fluorophore, a chemotherapeutic agent, an antiangiogenic agent, a thermoablative nanoparticle, an immunomodulating agent, or an antigen. Numerous examples of each of these categories are well known in the art.

In certain embodiments, where the peptide does not include a C-terminal linked phoshoester moiety, the peptide may instead include at its C-terminal amino acid a glycoside moiety or 3-aminophenyl boronic acid, which is linked to the peptide by a peptide bond. The glycoside can be any monosaccharide or disaccharide, including without limitation, fructosyl, galactosyl, glucosyl, or mannosyl. One exemplary glycoside is D-glucosamine ("GlcN"). In accordance with this embodiment, the peptide may comprise an N-terminal heterocyclic aromatic group. The heterocyclic aromatic group can protect against enzymatic degradation of the peptide, as well as promote self-assembly.

In certain embodiments, the peptide does not contain a nucleobase capping moiety except when the peptide also includes a C-terminal glycoside moiety, 3-aminophenyl boronic acid, or a C-terminal phosphoester moiety.

The peptides of the present invention can have any length that is sufficient to allow for self-assembly once the enzyme (preferably an ectoenzyme having hydrolase activity) dephosphorylates, desulfates, and/or de-esterifies the peptide. This includes peptides up to about 35 amino acids, up to about 30 amino acids, up to about 25 amino acids, up to about 20 amino acids, up to about 15 amino acids, or up to about 10 amino acids. In certain embodiments, the peptides contain from 2 to 10 amino acids, 2 to 9 amino acids, 2 to 8 amino acids, 3 to 7 amino acids, 3 to 6 amino acids, or 3 to 5 amino acids.

In certain embodiments, the peptide contains about 10 percent up to about 100 percent of aromatic amino acid residues.

Although numerous oligopeptides are known to form supermolcular hydrogels, those containing multiple aromatic groups facilitate aromatic-aromatic interactions that likely stabilize the intermolecular hydrogen bonding in water to afford the hydrogels. Du et al., "Supramolecular Hydrogels Made of Basic Biological Building Blocks," Chem. Asian J. 9(6):1446-1472 (2014), which is hereby incorporated by reference in its entirety. Examples include, without limitation, the conjugation of aromatic moieties (e.g., phenyl, naphthyl, fluorenyl, pyrenyl, cinnamoyl) via simple amide bond to either or both of aromatic amino acids (e.g., phenylalanine, tyrosine, and tryptophan) and non-aromatic amino acids. In addition, aromatic derivatives of amino acids can be used, such as naphthylalanine.

The redox modulator that is conjugated to the peptide is preferably one that is targeted to mitochondria and induces mitochondrial dysfunction, thereby contributing to either the cell death of targeted cells, the cessation of growth and division in the targeted cells, as well as the cessation of target cell migration.

Exemplary redox modulators include, without limitation, a triphenylphosphonium (TPP) moiety having the structure:

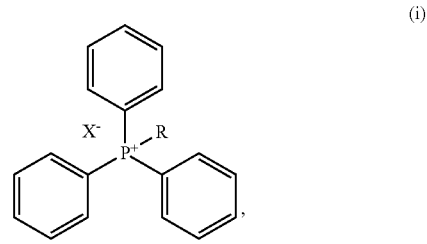

(i)

where R is a linker having a reactive group that is capable of reaction with an amino acid sidechain of the peptide and X⁻ is a pharmaceutically acceptable anion. By way of example, the linker, R, can be a hydrocarbon having a reactive terminal group. Exemplary reactive terminal groups include an amino group reactive with, e.g., glutamic acid or aspartic acid sidechains; an N-hydroxysuccinimide group reactive with, e.g., glutamic acid or aspartic acid sidechains; a carboxylic acid group reactive with, e.g., lysine, arginine, or histidine sidechains; a thiol group reactive with, e.g., cysteine sidechain, or an unsaturated olefin group reactive with, e.g., allylglycine or propargylglycine using a ruthenium-catalyzed olefin metathesis (see Hoveyda et al., *Nature* 450:243-251 (2007), which is hereby incorporated by reference in its entirety) which is compatible with solid-phase peptide synthesis reactions described hereinafter.

(ii) mitochondrially-targeted phthalazinediones of the type identified in U.S. Pat. No. 7,326,690 to Henry et al., which is hereby incorporated by reference in its entirety and which identifies 5- and 6-substituted phthalazinediones

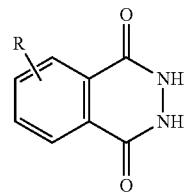

where R is one of the exemplary amino or substituted amino groups exemplified below, or a derivative thereof that allows for linkage to an amino acid side chain in the manner described above for TPP derivatives. In general, aminophthalazinediones, haloaminophthalazinediones (e.g., bromoaminophthalazinedione, chloroaminophthalazinedione, fluoroaminophthalazinedione, iodoaminophthalazinedione), alkylaminophthalazinediones (e.g., methylaminophthalazinedione, ethylaminophthalazinedione, propylaminophthalazinedione, isopropylaminophthalazinedione, dimethylaminophthalazinedione), acylaminophthalazinediones (e.g., methanoylamino-phthalazinedione, ethanoylaminophthalazinedione, propanoylamino-phthalazinedione, hydroxylaminophthalazinedione, carboxylaminophthalazinedione), alkanolaminophthalazinediones (e.g., methanolaminophthalazinedione, ethanolamino-phthalazinedione, propano-laminophthalazinedione), alkenylaminophthalazinediones (e.g., methenylaminophthalazinedione, ethenylaminophthalazinedione, propenylamino-phthalazinedione), alkoxyaminophthalazinediones (e.g., methoxyaminophthalazinedione, ethoxyaminophthalazinedione, propoxyaminophthalazinedione), haloalkylamino-phthalazinediones, allylaminophthalazinediones, and sulfhydrylaminophthalazinediones are preferred classes. Exemplary 5- and 6-substituted phthalazinedione include, without limitation, 5-amino-2,3-dihydrophthalazine-1,4-dione (luminol), 6-amino-2,3-dihydrophthalazine-1,4-dione (isoluminol), 5-amino-2,3-dihydrophthalazine-1,4-dion-8-yl (luminyl), N-bromo-5-amino-2,3-dihydrophthalazine-1,4-dione, N-chloro-5-amino-2,3-dihydrophthalazine-1,4-dione, N-fluoro-5-amino-2,3-dihydrophthalazine-1,4-dione, N-iodo-5-amino-2,3-dihydrophthalazine-1,4-dione, N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydrophthalazine-1,4-dione, N-ethanoyl-5-amino-2,3-dihydrophthalazine-1,4-dione, N-propanoyl-5-amino-2,3-dihydrophthalazine-1,4-dione, N-hydroxyl-5-amino-2,3-dihydrophthalazine-1,4-dione, N-carboxyl-5-amino-2,3-dihydrophthalazine-1,4-dione, N-methanol-5-amino-2,3-dihydrophthalazine-1,4-dione, N-ethanol-5-amino-2,3-dihydrophthalazine-1,4-dione, N-propanol-5-amino-2,3-dihydrophthalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydrophthalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5-amino-2,3-dihydrophthalazine-1,4-dione, N-acetylcysteine-5-amino-2,3-dihydrophthalazine-1,4-dione, and N-acetylglutathione-5-amino-2,3-dihydrophthalazine-1,4-dione.

(iii) mitochondria-targeting lipophilic agents of the type identified in U.S. Patent No. 20160279154 to Skulachev et al., which includes the substituted N,N'-diethylaminotriphenylmethane (DEATPM) structure illustrated below:

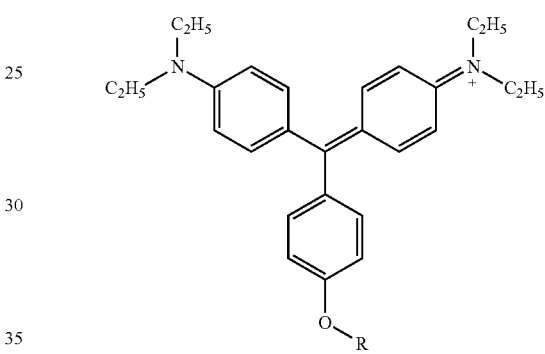

where R is a straight or branched hydrocarbon chain optionally substituted by one or more double or triple bonds, or ether bond, or ester bond, or C—S, or S—S, or peptide bond; and which is optionally substituted by one or more substituents preferably selected from alkyl, alkoxy, halogen, keto group, amino group, another functional group of the type described above, or a natural isoprene chain.

(iv) porphyrin redox modulators include, but are not limited to Cu porphyrins, Mn porphyrins, and Fe porphyrins. Suitable porphyrins include compounds of formula

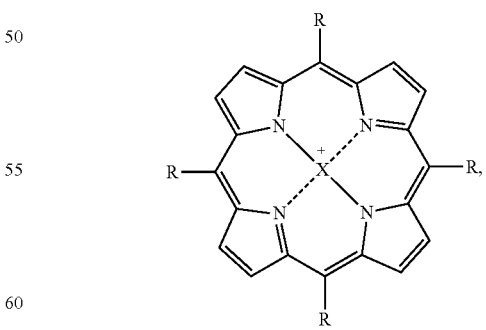

where R independently at each occurrence is selected from the group consisting of optionally substituted $C_{1-6}$ alkyl, optionally substituted $C_{3-6}$ cycloalkyl, optionally substituted aryl, optionally substituted heteroaryl; and X is 2H or a metal (e.g. Cu, Mn or Fe), and wherein at least one R group contains a suitable moiety that can be used to link the porphyrin redox modulators to a peptide of the type described above. Suitable moieties include, but are not limited to, —NH$_2$, —NHR', —COOH, —COR', —SH, —OH, —C(R')=C—(R')$_2$, or —N$_3$ moiety, and where R' is independently selected from the group consisting of H, optionally substituted C$_{1-6}$ alkyl, optionally substituted —OC$_{1-6}$ alkyl, halogen, —NH$_2$, and any suitable leaving group. (see Tovmasyan et al., "Design, Mechanism of Action, Bioavailability and Therapeutic Effects of Mn Porphyrin-Based Redox Modulators," *Med. Princ. Pract.* 22:103-130 (2013); Miriyala et al., "Manganese superoxide dismutase, MnSOD and its mimics," *Biochim. Biophys. Acta.* 1822(5):794-814 (2012), which are hereby incorporated by reference in their entirety). Suitable porphyrins also include

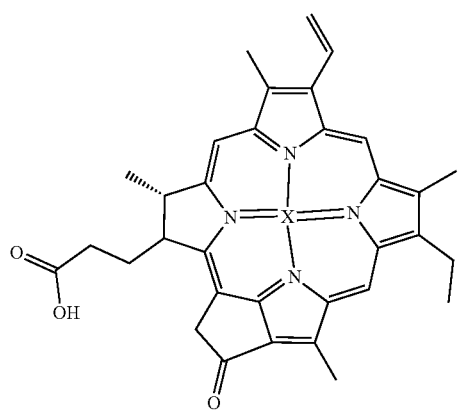

Pyropheophorbide A
X = 2H or Fe, Cu

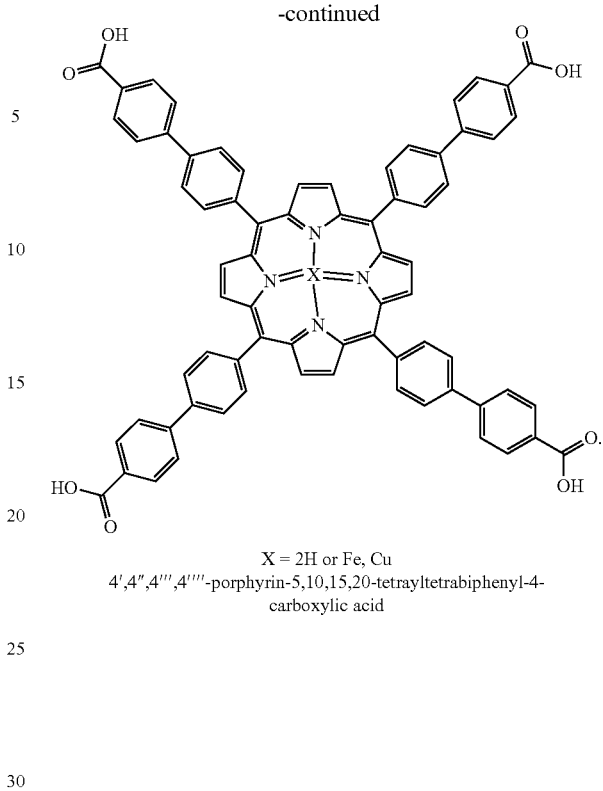

X = 2H or Fe, Cu
4',4'',4''',4''''-porphyrin-5,10,15,20-tetrayltetrabiphenyl-4-carboxylic acid Additional exemplary porphyrins include, without limitation,

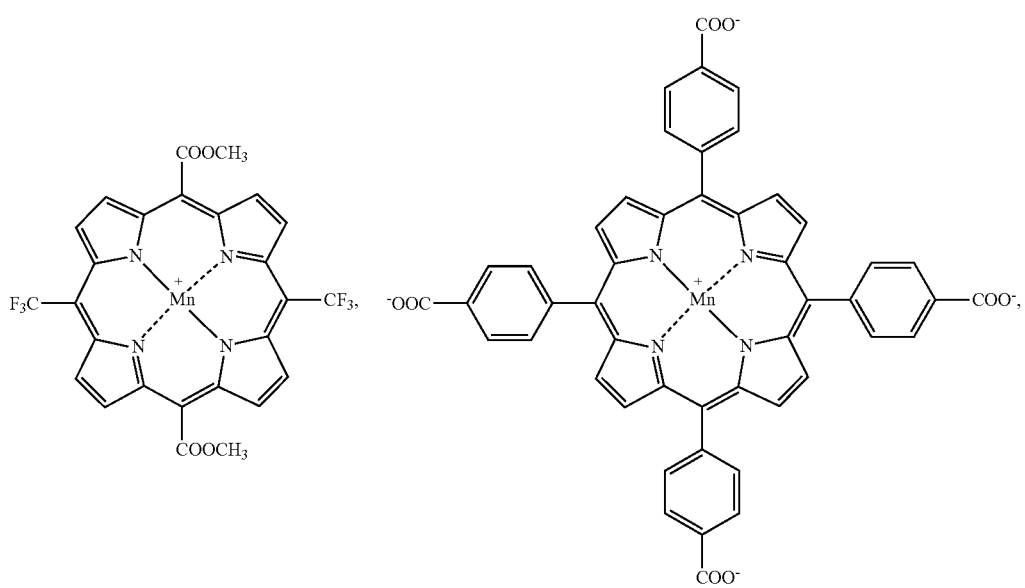

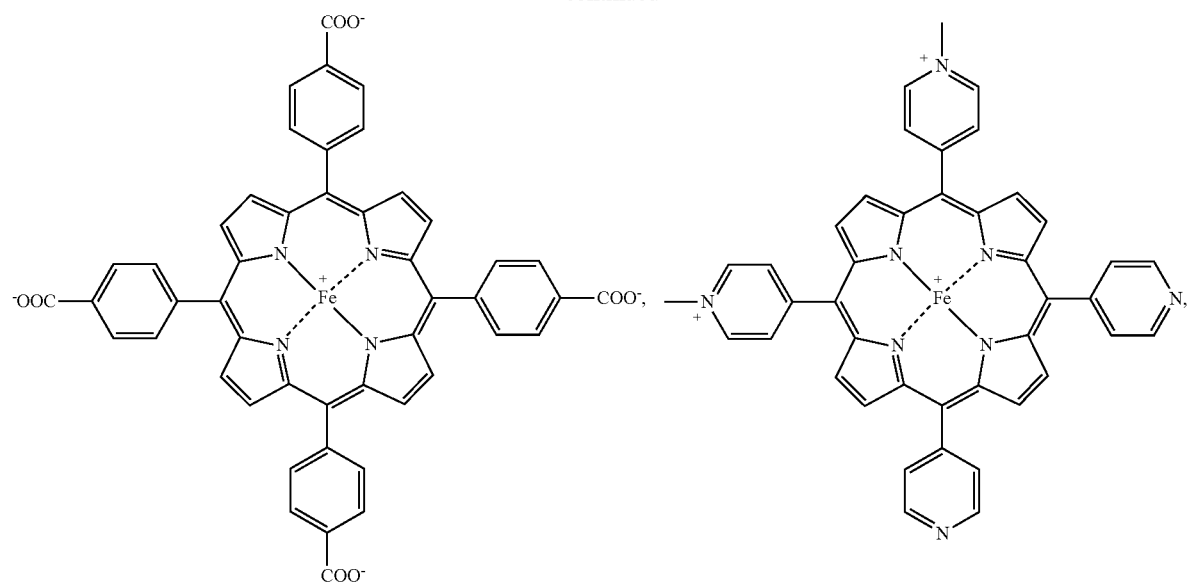
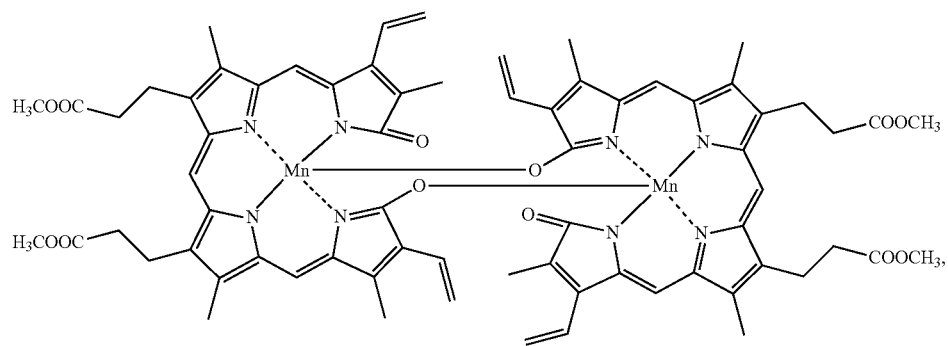
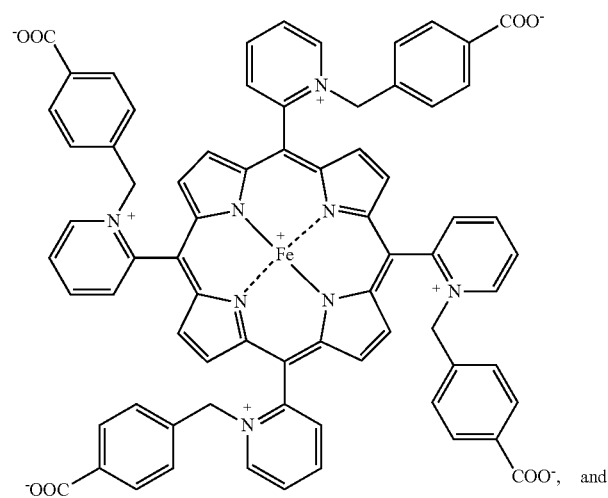

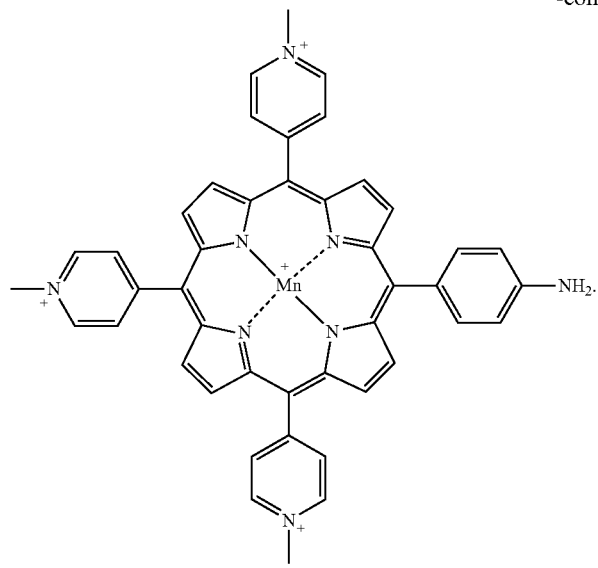

Additional porphyrin redox modulators are identified in Tovmasyan et al., "Design, Mechanism of Action, Bioavailability and Therapeutic Effects of Mn Porphyrin-Based Redox Modulators," *Med. Princ. Pract.* 22:103-130 (2013), and Miriyala et al., "Manganese superoxide dismutase, MnSOD and its mimics," *Biochim. Biophys. Acta.* 1822(5): 794-814 (2012), each of which is hereby incorporated by reference in its entirety.

Porphyrin derivatives containing a carboxylic acid group can be connected to the peptide using NHS to activate the carboxy group to form NHS ester, and then reacting the ester with the peptide (through ε-amino group on the lysine) or using triphosgen to activate a carboxylic acid to form acyl chloride, which can react with ε-amino group on the lysine.

Thus, according to one embodiment, peptide-redox modulator conjugates of the present invention include the TPP-conjugated amino acid:

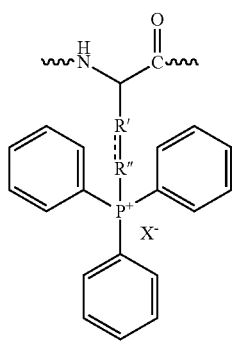

where R' is the modified sidechain of an amino acid reactive with the functional group of the linker R of TPP, R" is the residue of R in TPP, and the bond formed between R" and R' can be any covalent bond formed between the two reactive groups such as a disulfide bond, olefin bond, peptide bond, ester bond, or imine bond. Exemplary amino acids derivatized in this manner include, e.g., Glu(TPP), Asp(TPP), Lys(TPP), Arg(TPP), His(TPP), Cys(TPP), and allylGly(TPP), including both L- and D-amino acids.

According to another embodiment, peptide-redox modulator conjugates of the present invention include the phthalazinedione-conjugated amino acid:

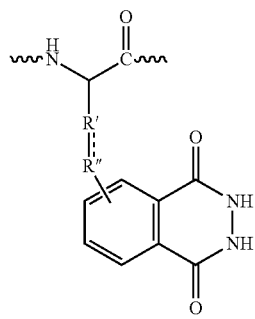

where R' is the modified sidechain of an amino acid reactive with the functional group of the linker R of the substituted phthalazinedione, R" is the residue of R in the substituted phthalazinedione, and the bond formed between R" and R' can be any covalent bond formed between the two reactive groups such as a disulfide bond, olefin bond, peptide bond, ester bond, or imine bond. Exemplary amino acids derivatized in this manner include, e.g., Glu(phthalazinedione), Asp(phthalazinedione), Lys(phthalazinedione), Arg(phthalazinedione), His(phthalazinedione), Cys(phthalazinedione), and allylGly(phthalazinedione), including both L- and D-amino acids.

According to another embodiment, peptide-redox modulator conjugates of the present invention include the substituted-DEATPM-conjugated amino acid:

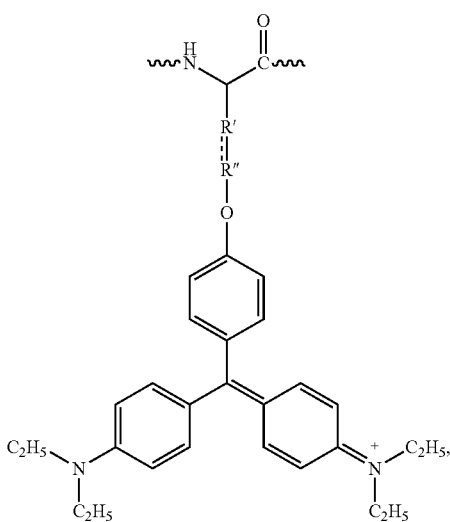

where R' is the sidechain of an amino acid reactive with the functional group of the linker R of the substituted-DEATPM molecule and R" is the residue thereof, and the bond formed between R" and R' can be any covalent bond formed between the two reactive groups such as a disulfide bond, olefin bond, peptide bond, ester bond, or imine bond. Exemplary amino acids derivatized in this manner include, e.g., Glu(DEATPM), Asp(DEATPM), Lys(DEATPM), Arg(DEATPM), His(DEATPM), Cys(DEATPM), and allylGly(DEATPM), including both L- and D-amino acids.

According to yet another embodiment, peptide-redox modulator conjugates of the present invention include the substituted-porphyrin-conjugated amino acid:

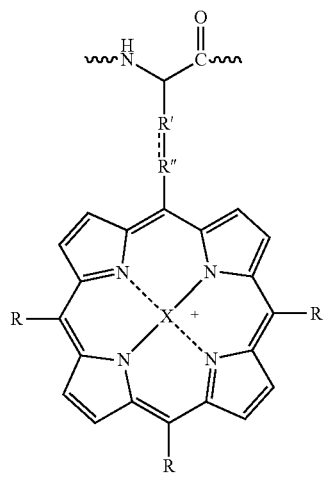

where R' is the modified sidechain of an amino acid reactive with the functional group of the porphyrin sidechain, R; R" is the residue of R in the porphyrin, and the bond formed between R" and R' can be any covalent bond formed between the two reactive groups such as a disulfide bond, olefin bond, peptide bond, ester bond, or imine bond, R independently at each occurrence is selected from the group consisting of optionally substituted $C_{1-6}$ alkyl, optionally substituted $C_{3-6}$ cycloalkyl, optionally substituted aryl, optionally substituted heteroaryl; and X is 2H or a metal (e.g. Cu, Mn or Fe), and wherein at least one R contains a suitable moiety that can be used to link the porphyrin redox modulators to a peptide. Suitable moieties include, but are not limited to, —$NH_2$, —NHR', —COOH, —COR', —SH, —OH, —C(R')=C—(R')$_2$, or —$N_3$ moiety, and where R' is independently selected from the group consisting of H, optionally substituted $C_{1-6}$ alkyl, optionally substituted —$OC_{1-6}$ alkyl, halogen, —$NH_2$, and any suitable leaving group. Exemplary amino acids derivatized in this manner include, e.g., Glu(porphyrin), Asp(porphyrin), Lys(porphyrin), Cys(porphyrin), and allylGly(porphyrin), including both L- and D-amino acids.

Exemplary peptide-redox modulator conjugates of the present invention include, without limitation:

Naphthyl-acetyl-NH-D-Phe-D-Phe-D-Tyr(phospho)-D-Lys(TPP)-COOH;
Naphthyl-acetyl-NH-D-Phe-D-Phe-D-Lys(TPP)-D-Tyr(phospho)-COOH;
Naphthyl-acetyl-NH-L-Phe-L-Phe-L-Tyr(phospho)-L-Lys(TPP)-COOH (SEQ ID NO: 2);
Naphthyl-acetyl-NH-L-Phe-L-Phe-L-Lys(TPP)-L-Tyr(phospho)-COOH (SEQ ID NO: 3);
NBD-acetyl-NH-D-Phe-D-Phe-D-Tyr(phospho)-D-Lys(TPP)-COOH;
NBD-acetyl-NH-D-Phe-D-Phe-D-Lys(TPP)-D-Tyr(phospho)-COOH;
NBD-acetyl-NH-L-Phe-L-Phe-L-Tyr(phospho)-L-Lys(TPP)-COOH (SEQ ID NO: 4);
NBD-acetyl-NH-L-Phe-L-Phe-L-Lys(TPP)-L-Tyr(phospho)-COOH (SEQ ID NO: 5);
Naphthyl-acetyl-NH-D-Phe-D-Phe-D-Tyr(phospho)-D-Lys(phthalazinedione)-COOH;
Naphthyl-acetyl-NH-D-Phe-D-Phe-D-Lys (phthalazinedione)-D-Tyr(phospho)-COOH;
Naphthyl-acetyl-NH-L-Phe-L-Phe-L-Tyr(phospho)-L-Lys(phthalazinedione)-COOH (SEQ ID NO: 6);
Naphthyl-acetyl-NH-L-Phe-L-Phe-L-Lys (phthalazinedione)-L-Tyr(phospho)-COOH (SEQ ID NO: 7);
NBD-acetyl-NH-D-Phe-D-Phe-D-Tyr(phospho)-D-Lys(phthalazinedione)-COOH;
NBD-acetyl-NH-D-Phe-D-Phe-D-Lys (phthalazinedione)-D-Tyr(phospho)-COOH;
NBD-acetyl-NH-L-Phe-L-Phe-L-Tyr(phospho)-L-Lys(phthalazinedione)-COOH (SEQ ID NO: 8);
NBD-acetyl-NH-L-Phe-L-Phe-L-Lys (phthalazinedione)-L-Tyr(phospho)-COOH (SEQ ID NO: 9);
Naphthyl-acetyl-NH-D-Phe-D-Phe-D-Tyr(phospho)-D-Lys(DEATPM)-COOH;
Naphthyl-acetyl-NH-D-Phe-D-Phe-D-Lys (DEATPM)-D-Tyr(phospho)-COOH;
Naphthyl-acetyl-NH-L-Phe-L-Phe-L-Tyr(phospho)-L-Lys(DEATPM)-COOH (SEQ ID NO: 10);
Naphthyl-acetyl-NH-L-Phe-L-Phe-L-Lys (DEATPM)-L-Tyr(phospho)-COOH (SEQ ID NO: 11);
NBD-acetyl-NH-D-Phe-D-Phe-D-Tyr(phospho)-D-Lys(DEATPM)-COOH;
NBD-acetyl-NH-D-Phe-D-Phe-D-Lys (DEATPM)-D-Tyr(phospho)-COOH;
NBD-acetyl-NH-L-Phe-L-Phe-L-Tyr(phospho)-L-Lys(DEATPM)-COOH (SEQ ID NO: 12);
NBD-acetyl-NH-L-Phe-L-Phe-L-Lys (DEATPM)-L-Tyr(phospho)-COOH (SEQ ID NO: 13);
Naphthyl-acetyl-NH-D-Phe-D-Phe-D-Tyr(phospho)-D-Lys(porphyrin)-COOH;
Naphthyl-acetyl-NH-D-Phe-D-Phe-D-Lys (porphyrin)-D-Tyr(phospho)-COOH;
Naphthyl-acetyl-NH-L-Phe-L-Phe-L-Tyr(phospho)-L-Lys(porphyrin)-COOH (SEQ ID NO: 14);

Naphthyl-acetyl-NH-L-Phe-L-Phe-L-Lys (porphyrin)-L-Tyr (phospho)-COOH (SEQ ID NO: 15);
NBD-acetyl-NH-D-Phe-D-Phe-D-Tyr(phospho)-D-Lys (porphyrin)-COOH;
NBD-acetyl-NH-D-Phe-D-Phe-D-Lys (porphyrin)-D-Tyr (phospho)-COOH;
NBD-acetyl-NH-L-Phe-L-Phe-L-Tyr(phospho)-L-Lys (porphyrin)-COOH (SEQ ID NO: 16);
NBD-acetyl-NH-L-Phe-L-Phe-L-Lys (porphyrin)-L-Tyr (phospho)-COOH (SEQ ID NO: 17);
Naphthyl-acetyl-NH-D-Phe-D-Phe-D-Tyr-D-Lys (porphyrin)-di(isopropyloxycarbonyloxymethyl)phosphoester;
Naphthyl-acetyl-NH-D-Phe-D-Phe-D-Lys (porphyrin)-D-Tyr-di(isopropyloxycarbonyloxymethyl)phosphoester;
Naphthyl-acetyl-NH-L-Phe-L-Phe-L-Tyr-L-Lys (porphyrin)-di(isopropyloxycarbonyloxymethyl)phosphoester (SEQ ID NO: 18);
Naphthyl-acetyl-NH-L-Phe-L-Phe-L-Lys (porphyrin)-L-Tyr-di(isopropyloxycarbonyloxymethyl)phosphoester (SEQ ID NO: 19);
NBD-acetyl-NH-D-Phe-D-Phe-D-Tyr-D-Lys (porphyrin)-di(isopropyloxycarbonyloxymethyl)phosphoester;
NBD-acetyl-NH-D-Phe-D-Phe-D-Lys (porphyrin)-D-Tyr-di(isopropyloxycarbonyloxymethyl)phosphoester;
NBD-acetyl-NH-L-Phe-L-Phe-L-Tyr-L-Lys (porphyrin)-di(isopropyloxycarbonyloxymethyl)phosphoester (SEQ ID NO: 20);
NBD-acetyl-NH-L-Phe-L-Phe-L-Lys (porphyrin)-L-Tyr-di(isopropyloxycarbonyloxymethyl)phosphoester (SEQ ID NO: 21);
Naphthyl-acetyl-NH-D-Phe-D-Phe-D-Tyr-D-Lys(TPP)-di(isopropyloxycarbonyloxymethyl) phosphoester;
Naphthyl-acetyl-NH-D-Phe-D-Phe-D-Lys(TPP)-D-Tyr-di(isopropyloxycarbonyloxymethyl) phosphoester;
Naphthyl-acetyl-NH-L-Phe-L-Phe-L-Tyr-L-Lys(TPP)-di(isopropyloxycarbonyloxymethyl) phosphoester (SEQ ID NO: 22);
Naphthyl-acetyl-NH-L-Phe-L-Phe-L-Lys(TPP)-L-Tyr-di(isopropyloxycarbonyloxymethyl) phosphoester (SEQ ID NO: 23);
NBD-acetyl-NH-D-Phe-D-Phe-D-Tyr-D-Lys(TPP)-di(isopropyloxycarbonyloxymethyl) phosphoester;
NBD-acetyl-NH-D-Phe-D-Phe-D-Lys(TPP)-D-Tyr-di(isopropyloxycarbonyloxymethyl) phosphoester;
NBD-acetyl-NH-L-Phe-L-Phe-L-Tyr-L-Lys(TPP)-di(isopropyloxycarbonyloxymethyl) phosphoester (SEQ ID NO: 24);
NBD-acetyl-NH-L-Phe-L-Phe-L-Lys(TPP)-L-Tyr-di(isopropyloxycarbonyloxymethyl) phosphoester (SEQ ID NO: 25);
Naphthyl-acetyl-NH-D-Phe-D-Phe-D-Tyr-D-Lys(TPP)-di(isopropyloxycarbonyloxymethyl) phosphoester;
Naphthyl-acetyl-NH-D-Phe-D-Phe-D-Lys (phthalazinedione)-D-Tyr-di(isopropyloxycarbonyl-oxymethyl) phosphoester;
Naphthyl-acetyl-NH-L-Phe-L-Phe-L-Tyr-L-Lys (phthalazinedione)-di(isopropyloxycarbonyl-oxymethyl)phosphoester (SEQ ID NO: 26);
Naphthyl-acetyl-NH-L-Phe-L-Phe-L-Lys (phthalazinedione)-L-Tyr-di(isopropyloxycarbonyl-oxymethyl) phosphoester (SEQ ID NO: 27);
NBD-acetyl-NH-D-Phe-D-Phe-D-Tyr-D-Lys (phthalazinedione)-di(isopropyloxycarbonyl-oxymethyl)phosphoester;
NBD-acetyl-NH-D-Phe-D-Phe-D-Lys (phthalazinedione)-D-Tyr-di(isopropyloxycarbonyl-oxymethyl)phosphoester;
NBD-acetyl-NH-L-Phe-L-Phe-L-Tyr-L-Lys (phthalazinedione)-di(isopropyloxycarbonyl-oxymethyl)phosphoester (SEQ ID NO: 28);
NBD-acetyl-NH-L-Phe-L-Phe-L-Lys (phthalazinedione)-L-Tyr-di(isopropyloxycarbonyl-oxymethyl)phosphoester (SEQ ID NO: 29);
Naphthyl-acetyl-NH-D-Phe-D-Phe-D-Tyr-D-Lys (DEATPM)-di(isopropyloxycarbonyl-oxymethyl)phosphoester;
Naphthyl-acetyl-NH-D-Phe-D-Phe-D-Lys (DEATPM)-D-Tyr-di(isopropyloxycarbonyl-oxymethyl)phosphoester;
Naphthyl-acetyl-NH-L-Phe-L-Phe-L-Tyr-L-Lys (DEATPM)-di(isopropyloxycarbonyl-oxymethyl)phosphoester (SEQ ID NO: 30);
Naphthyl-acetyl-NH-L-Phe-L-Phe-L-Lys (DEATPM)-L-Tyr-di(isopropyloxycarbonyl-oxymethyl)phosphoester (SEQ ID NO: 31);
NBD-acetyl-NH-D-Phe-D-Phe-D-Tyr-D-Lys (DEATPM)-di(isopropyloxycarbonyloxymethyl)phosphoester;
NBD-acetyl-NH-D-Phe-D-Phe-D-Lys (DEATPM)-D-Tyr-di(isopropyloxycarbonyloxymethyl)phosphoester;
NBD-acetyl-NH-L-Phe-L-Phe-L-Tyr-L-Lys (DEATPM)-di(isopropyloxycarbonyloxymethyl)phosphoester (SEQ ID NO: 32);
NBD-acetyl-NH-L-Phe-L-Phe-L-Lys (DEATPM)-L-Tyr-di(isopropyloxycarbonyloxymethyl)phosphoester (SEQ ID NO: 33); and
Naphthyl-acetyl-NH-D-Phe-D-Phe-D-Tyr-D-Lys (DEATPM)-di(isopropyloxycarbonyl-oxymethyl)phosphoester;

where NBD is the fluorophore 4-nitro-2,1,3-benzoxadiazole group, the di(isopropyloxycarbonyloxymethyl)phosphoester group has the following structure attached to the C-terminal carbonyl:

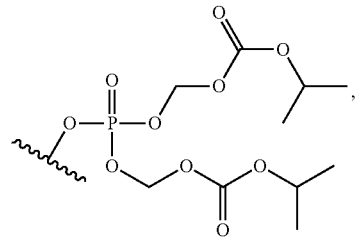 [SMILES: *OP(=O)(OCOC(=O)OC(C)C)OCOC(=O)OC(C)C]

and the di(ethyl)phosphoester group has the following structure attached to the C-terminal carbonyl:

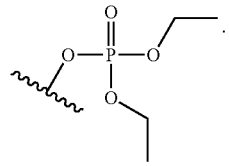 [SMILES: *OP(=O)(OCC)OCC]

The peptide component of the conjugate can be synthesized using standard peptide synthesis operations. These include both 9-Fluorenylmethyloxy-carbonyl ("FMOC") and tert-Butyl oxy carbonyl ("tBoc") synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. This can be followed with standard HPLC purification to achieve a purified peptide product.

Where N-terminal capping groups or C-terminal moieties are introduced, these can also be introduced using standard peptide synthesis operations as described above. For example, carboxylic acid containing precursors can be coupled by peptide bond to the N-terminus of the peptide, and amino containing precursors can be coupled by peptide bond to the C-terminus of the peptide.

In general, amino groups present in lysine side chains (if present), as well as the N-terminal amino group, can be reacted with reagents possessing amine-reactive functional groups using known reaction schemes. Exemplary amine-reactive functional groups include, without limitation, activated esters, isothiocyanates, and carboxylic acids. Reagents to be conjugated include those listed above.

In general, guanidine groups present in arginine can be reacted with reagents possessing guanidine-reactive groups using known reaction schemes. Exemplary guanidine-reactive functional groups include, without limitation, NHS esters using gas phase synthesis (McGee et al., *J. Am. Chem. Soc.*, 134 (28):11412-11414 (2012), which is hereby incorporated by reference in its entirety).

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

In general, carboxyl groups present in glutamic or aspartic acid side chains, or at the C-terminal amino acid residue, can be reacted with reagents possessing carboxyl-reactive functional groups using known reaction schemes. Exemplary carboxyl-reactive functional groups include, without limitation, amino groups, amines, bifunctional amino linkers. Reagents to be conjugated include those listed above.

In each of the types of modifications described above, it should be appreciated that the conjugate can be directly linked via the functional groups of the peptide and the reagent to be conjugated, or via a bifunctional linker that reacts with both the peptide functional groups and the functional groups on the reagent to be conjugated.

In general, the enzymatically activated peptide-redox modulator conjugates of the present invention can be either (i) dephosphorylated or desulfated, (ii) hydrolyzed at a phosphoester bond, or both (i) and (ii) to form a derivative hydrogelator. Exemplary derivative hydrogelators include:

Naphthyl-acetyl-NH-D-Phe-D-Phe-D-Tyr-D-Lys(TPP)-COOH;
Naphthyl-acetyl-NH-D-Phe-D-Phe-D-Lys(TPP)-D-Tyr-COOH;
Naphthyl-acetyl-NH-L-Phe-L-Phe-L-Tyr-L-Lys(TPP)-COOH (SEQ ID NO: 34);
Naphthyl-acetyl-NH-L-Phe-L-Phe-L-Lys(TPP)-L-Tyr-COOH (SEQ ID NO: 35);
NBD-acetyl-NH-D-Phe-D-Phe-D-Tyr-D-Lys(TPP)-COOH;
NBD-acetyl-NH-D-Phe-D-Phe-D-Lys(TPP)-D-Tyr-COOH;
NBD-acetyl-NH-L-Phe-L-Phe-L-Tyr-L-Lys(TPP)-COOH (SEQ ID NO: 36);
NBD-acetyl-NH-L-Phe-L-Phe-L-Lys(TPP)-L-Tyr-COOH (SEQ ID NO: 37);
Naphthyl-acetyl-NH-D-Phe-D-Phe-D-Tyr-D-Lys (phthalazinedione)-COOH;
Naphthyl-acetyl-NH-D-Phe-D-Phe-D-Lys (phthalazinedione)-D-Tyr-COOH;
Naphthyl-acetyl-NH-L-Phe-L-Phe-L-Tyr-L-Lys (phthalazinedione)-COOH (SEQ ID NO: 38);
Naphthyl-acetyl-NH-L-Phe-L-Phe-L-Lys (phthalazinedione)-L-Tyr-COOH (SEQ ID NO: 39);
NBD-acetyl-NH-D-Phe-D-Phe-D-Tyr-D-Lys (phthalazinedione)-COOH;
NBD-acetyl-NH-D-Phe-D-Phe-D-Lys (phthalazinedione)-D-Tyr-COOH;
NBD-acetyl-NH-L-Phe-L-Phe-L-Tyr-L-Lys (phthalazinedione)-COOH (SEQ ID NO: 40);
NBD-acetyl-NH-L-Phe-L-Phe-L-Lys (phthalazinedione)-L-Tyr-COOH (SEQ ID NO: 41);
Naphthyl-acetyl-NH-D-Phe-D-Phe-D-Tyr-D-Lys (DEATPM)-COOH;
Naphthyl-acetyl-NH-D-Phe-D-Phe-D-Lys (DEATPM)-D-Tyr-COOH;
Naphthyl-acetyl-NH-L-Phe-L-Phe-L-Tyr-L-Lys (DEATPM)-COOH (SEQ ID NO: 42);
Naphthyl-acetyl-NH-L-Phe-L-Phe-L-Lys (DEATPM)-L-Tyr-COOH (SEQ ID NO: 43);
NBD-acetyl-NH-D-Phe-D-Phe-D-Tyr-D-Lys (DEATPM)-COOH;
NBD-acetyl-NH-D-Phe-D-Phe-D-Lys (DEATPM)-D-Tyr-COOH;
NBD-acetyl-NH-L-Phe-L-Phe-L-Tyr-L-Lys (DEATPM)-COOH (SEQ ID NO: 44);
NBD-acetyl-NH-L-Phe-L-Phe-L-Lys (DEATPM)-L-Tyr-COOH (SEQ ID NO: 45);
Naphthyl-acetyl-NH-D-Phe-D-Phe-D-Tyr-D-Lys (porphyrin)-COOH;
Naphthyl-acetyl-NH-D-Phe-D-Phe-D-Lys (porphyrin)-D-Tyr-COOH;
Naphthyl-acetyl-NH-L-Phe-L-Phe-L-Tyr-L-Lys (porphyrin)-COOH (SEQ ID NO: 46);
Naphthyl-acetyl-NH-L-Phe-L-Phe-L-Lys (porphyrin)-L-Tyr-COOH (SEQ ID NO: 47);
NBD-acetyl-NH-D-Phe-D-Phe-D-Tyr-D-Lys (porphyrin)-COOH;
NBD-acetyl-NH-D-Phe-D-Phe-D-Lys (porphyrin)-D-Tyr-COOH;
NBD-acetyl-NH-L-Phe-L-Phe-L-Tyr-L-Lys (porphyrin)-COOH (SEQ ID NO: 48); and
NBD-acetyl-NH-L-Phe-L-Phe-L-Lys (porphyrin)-L-Tyr-COOH (SEQ ID NO: 49).

A second aspect of the invention relates to a pharmaceutical composition comprising a pharmaceutically acceptable carrier and a peptide-redox modulator conjugate according to the first aspect of the invention, which is present in an effective amount.

In certain embodiments, more than one peptide-redox modulator conjugate can be provided. The peptides can be similar in structure, but possess different conjugated agents as described above. In alternative embodiments, the peptides can be structurally distinct, including different structures that are nevertheless capable of self-assembly due to the structural compatibility of the aromatic amino acid residues in the different peptides.

In certain embodiments, the carrier is an aqueous medium that is well tolerated for administration to an individual, typically a sterile isotonic aqueous buffer. Exemplary aqueous media include, without limitation, normal saline (about 0.9% NaCl), phosphate buffered saline ("PBS"), sterile water/distilled autoclaved water ("DAW"), as well as cell growth medium (e.g., MEM, with or without serum), aqueous solutions of dimethyl sulfoxide ("DMSO"), polyethylene glycol ("PEG"), and/or dextran (less than 6% per by weight.)

To improve patient tolerance to administration, the pharmaceutical composition preferably has a pH of about 6 to about 8, preferably about 6.5 to about 7.4. Typically, sodium hydroxide and hydrochloric acid are added as necessary to adjust the pH.

The pharmaceutical composition suitably includes a weak acid or salt as a buffering agent to maintain pH. Citric acid has the ability to chelate divalent cations and can thus also prevent oxidation, thereby serving two functions as both a buffering agent and an antioxidant stabilizing agent. Citric acid is typically used in the form of a sodium salt, typically 10-500 mM. Other weak acids or their salts can also be used.

The composition may also include solubilizing agents, preservatives, stabilizers, emulsifiers, and the like. A local anesthetic (e.g., lidocaine, benzocaine, etc.) may also be included in the compositions, particularly for injectable forms, to ease pain at the site of the injection.

Effective amounts of the peptide will depend on the nature of use, including the nature of the cancerous condition which is being treated, tumor volume and stage, and its location(s). By way of example only, suitable peptide concentrations may range from about 1 µM to about 10 mM, preferably about 10 µM to about 5 mM, about 50 µM to about 2 mM, or about 100 µM to about 1 mM. The volume of the composition administered, and thus, dosage of the peptide administered can be adjusted by one of skill in the art to achieve optimized results.

Further aspects of the invention relate to methods of forming a nanofibril network on or near the surface of target cells, particularly cancer cells, and methods of treating a cancerous condition in a patient.

In accordance with another aspect of the invention, relating to methods of forming a nanofibril network on or near the surface of target cells, the method involves contacting a target cell that expresses a cell surface-bound enzyme having hydrolytic (hydrolase) activity, secretes an enzyme having hydrolytic (hydrolase) activity, or both, with a peptide of the invention or a pharmaceutical composition containing the same, wherein the contacting is effective to hydrolyze the phosphate group, the sulfate group, or the phosphoester moiety and cause in situ self-assembly of the peptides to form a nanofibril network on or near the surface of the target cell. As a consequence of forming the nanofibril network on or near the target cell surface, one or more of the following occurs: target cell migration is inhibited, target cell survival is inhibited, target cell growth is inhibited, and/or passage of intracellular signaling molecules to or from the nanofibril network-covered target cell is inhibited. The target cell can be ex vivo or in vivo (in accordance with the method of treatment described below).

In each of the above embodiments relating to methods of forming a nanofibril network on or near the surface of target cells, the target cells may be cancer cells. In accordance with these embodiments of the method of forming a nanofibril network on or near the surface of target cells, the nanofibril network is partially internalized are routed to mitochondria. This mitochondrial uptake of the gel containing the redox modulator causes disruption of mitochondrial processes and, eventually, inhibition of cancer cell migration, inhibition of cancer cell survival, and/or inhibition of cancer cell growth.

In accordance with another aspect of the invention, relating to methods of treating a cancerous condition in a subject, the method involves administering to a subject having a cancerous condition a therapeutically effective amount of a peptide of the invention or a pharmaceutical composition containing the same, wherein the administering is effective to hydrolyze the phosphate group, the sulfate group, or the phosphoester moiety and cause in vivo self-assembly of the peptides to form a nanofibril network on or near the surface of cancer cells, which has the effects noted above. Exemplary subjects include any mammal that is susceptible to cancerous conditions including, without limitation, rodents, rabbits, canines, felines, ruminants, and primates such as monkeys, apes, and humans.

In this aspect of the invention, the contacting step is effective to inhibit target cell migration, inhibit target cell survival, and/or inhibit target cell growth.

Administration of the peptide or pharmaceutical composition can be carried out using any suitable approach. By way of example, administration can be carried out parenterally, subcutaneously, intravenously, intradermally, intramuscularly, intraperitoneally, by implantation, by intracavitary or intravesical instillation, intraarterially, intralesionally, intradermally, peritumorally, intratumorally, or by introduction into one or more lymph nodes. In certain embodiments, administration is carried out intralesionally, intratumorally, intradermally, or peritumorally. This administration can be repeated periodically during the course of a treatment regimen, for example, one or more times per week, daily, or even one or more times per day.

In certain embodiments, the peptide is also conjugated with a chemotherapeutic agent, an antiangiogenic agent, an immunomodulating agent, or an antigen. In one embodiment, the peptide may be conjugated with a thermoablative nanoparticle. In accordance with this embodiment, the method of treating a cancerous condition in subject further comprises exposing a tumor-containing region of the subject's body to a suitable energy source (e.g., ultrasound, laser light, near infrared light, or alternating magnetic field), thereby causing thermal heating of the thermoablative nanoparticle and destroying cancer cells covered by the nanofibril network.

In these several aspects of the invention relating to methods of forming a nanofibril network on or near the surface of target cells, and methods of treating a cancerous condition in a patient, the target cells express a cell surface-bound phosphatase, secrete a phosphatase, or both; express a cell surface-bound sulfatase, secrete a sulfatase, or both; express a cell surface-bound esterase, secrete an esterase, or both; or any combination thereof. In these embodiments, the enzyme produced by the target cells is an ectoenzyme having hydrolytic activity, i.e., the enzyme hydrolyzes a phosphate group, a sulfate group, or a (carboxyl) ester group.

The target cells to be treated in accordance with these aspects can be a cancer cell and may be present in a solid tumor, present as a metastatic cell, or present in a heterogenous population of cells that includes both cancerous and noncancerous cells. Exemplary cancer conditions include, without limitation, cancers or neoplastic disorders of the brain and CNS (glioma, malignant glioma, glioblastoma, astrocytoma, multiforme astrocytic gliomas, medulloblastoma, craniopharyngioma, ependymoma, pinealoma, hemangioblastoma, acoustic neuroma, oligodendroglioma, meningioma), pituitary gland, breast (Infiltrating, Pre-invasive, inflammatory cancers, Paget's Disease, Metastatic and Recurrent Breast Cancer), blood (Hodgkin's Disease, Leukemia, Multiple Myeloma, Lymphoma), lymph node cancer, lung (Adenocarcinoma, Oat Cell, Non-small Cell, Small Cell, Squamous Cell, Mesothelioma), skin (melanoma, basal cell, squamous cell, Kapsosi's Sarcoma), bone cancer (Ewing's Sarcoma, Osteosarcoma, Chondrosarcoma), head and neck (laryngeal, pharyngeal, and esophageal cancers), oral (jaw, salivary gland, throat, thyroid, tongue, and tonsil cancers), eye, gynecological (Cervical, Endometrial, Fallopian, Ovarian, Uterine, Vaginal, and Vulvar), genitourinary (Adrenal, bladder, kidney, penile, prostate, testicular, and urinary cancers), and gastrointestinal (appendix, bile duct (extrahepatic bile duct), colon, gallbladder, gastric, intestinal, liver, pancreatic, rectal, and stomach cancers). Suitable cancer target cells include cancer cells derived from the forms of cancer.

Use of the peptides and pharmaceutical compositions can be coordinated with previously known therapies. For instance, where the peptide is conjugated with a thermoablative nanoparticle, after formation of the pericellular nanofibril network, a tumor-containing region of the subject's body can be exposed to a suitable energy source, thereby causing thermal heating of the thermoablative nanoparticle and destruction of cancer cells covered by the nanofibril network.

In addition, chemotherapeutic agents, immunotherapeutic agents, or radiotherapeutic agents, as well as surgical intervention can be used in a coordinated manner with the peptides or pharmaceutical compositions of the present invention. Thus, a chemotherapeutic agent, an immunotherapeutic agent, or a radiotherapeutic agent can be administered to a patient before or after treatment with the peptides or pharmaceutical compositions of the present invention. Alternatively, surgical resection of a tumor can be carried out before or after treatment with the peptides or pharmaceutical compositions of the present invention.

Additional target cells that express ectoenzymes of the types described above are mammalian progenitor cells, virus-infected cells, bacterial pathogen, protozoa, and fungi. Some of the bacterial pathogens expressing an ectoenzyme are described in PCT Publication No. WO 02/10442 to Zyskind, which is hereby incorporated by reference in its entirety. Ectophosphatase activities have been reported in several microorganisms (Freitas-Mesquita et al., *Int. J. Mol. Sci.* 15:2289-2304 (2014), which is hereby incorporated by reference in its entirety), including protozoa such as *Leishmania* (Remaley et al., *Exp. Parasitol.* 60:331-341 (1985); De Almeida-Amaral et al., *Exp. Parasitol.* 114:334-340 (2006), which are hereby incorporated by reference in their entirety), *Trypanosoma* (Fernandes et al., *Z. Naturforschung* 52C:351-358 (1997); Meyer-Fernandes et al., *Z. Naturforschung* 54:977-984 (1999); Dos-Santos et al., *Int. J. Parasitol.* 42:819-827 (2012), which are hereby incorporated by reference in their entirety), and bacteria, such as *Mycobacterium bovis* (Braibant et al., *FEMS Microbiol. Lett.* 195: 121-126 (2001), which is hereby incorporated by reference in its entirety). In fungi, ectophosphatases have been described in a large number of species (Freitas-Mesquita et al., *Int. J. Mol. Sci.* 15:2289-2304 (2014), which is hereby incorporated by reference in its entirety), including *Aspergillus fumigatus* (Bernard et al., *Microbiology* 148:2819-2829 (2002), which is hereby incorporated by reference in its entirety), and *Candida albicans* (Portela et al., *Oral Dis.* 16:431-437 (2010), which is hereby incorporated by reference in its entirety).

EXAMPLES

The following examples are intended to illustrate the present invention, but are not intended to limit the scope of the appended claims.

Materials and Methods for Examples 1-10
Experimental Materials and Instruments

2-Cl-trityl chloride resin (0.6 mmol/g), Fmoc protected amino acid, HBTU and Fmoc-OSu were obtained from GL Biochem (Shanghai, China). N, N-Diisopropylethylamine (DIPEA), TPP and other chemical reagents and solvents were obtained from Fisher Scientific; all chemical reagents and solvents were used as received from commercial sources without further purification; alkaline phosphatase was purchased from Biomatik. Dulbecco's modified Eagle's medium (DMEM), McCoy's 5a Medium and 1640 Medium were purchased from ATCC and fetal bovine serum (FBS) and penicillin/streptomycin were purchased from Gibco by life technologies. 3-(4,5-Dimethylthiazol-2-yl)-2,5-diphenyltetrazolium bromide (MTT) were purchased from ACROS Organics. All precursors were purified with Water Delta600 HPLC system, equipped with an XTerra C18 RP column. LC-MS spectrum was obtained on Waters Acquity Ultra Performance LC with Waters MICROMASS detector, and $^1$H-NMR spectra on Varian Unity Inova 400, and TEM images on Morgagni 268 transmission electron microscope. MTT assay for cell viability test on DTX880 Multimode Detector.

TEM Sample Preparation

First the sample solution was placed by use of a pipettor on the carbon coated grid (5 µL, sufficient to cover the grid surface). After 30 seconds, the grid was placed with the face of sample to a large drop of ddH$_2$O on parafilm and the grid was allowed to touch the water drop for 5 seconds, then grid was tilted and water was gently absorbed from the edge of the grid using a filter paper sliver. This process was repeated three times.

Staining was done immediately after rinsing, by place a large drop of the UA (uranyl acetate, 2% v/v) stain solution on parafilm and letting the grid touch the stain solution drop, with the sample-loaded surface facing the parafilm. The grid was tilted and the stain solution was gently absorbed from the edge of the grid using a filter paper sliver. The grid was allowed to dry in the air and was examined as soon as possible.

Cell Culture and MTT Assay

Saos2, HeLa, HepG2, T98G, MCF-7 and HS-5 cells were purchased from American-type Culture Collection (ATCC, USA). Saos2 cells were cultured in Macyo's 5A medium supplemented with 15% v/v fetal bovine serum, 100 U/mL penicillin and 100 µg/mL streptomycin. HeLa, HepG2, T98G, MCF-7 cells were cultured in MEM Medium supplemented with 10% v/v fetal bovine serum, HS-5 cells were cultured in Dulbecco's Modified Eagle's medium (DMEM) supplemented with 10% v fetal bovine serum (FBS), 100 U/mL penicillin and 100 µg/mL streptomycin. All cells were cultured at 37° C. in a humidified atmosphere of 5% CO$_2$.

For the MTT Assay, all cells were seeded in a 96-well plate with the density of 1*10$^4$ cells per-well (total medium volume of 100 µL). 24 hours post seeding, the solutions with a serial of concentrations (5 concentrations) of different precursors were added to each well. Cells without the treatment of the precursors were used as the control. At designated time (24/48/72 hours), 10 µL MTT solution (5 mg/mL) was added to each well and incubated at 37° C. for another 4 h, and then 100 µL of SDS-HCl solution was added to stop the reduction reaction and dissolve the purple formazan. The absorbance of each well at 595 nm was measured by a multimode microplate reader. The cytotoxicity assay was performed three times and the average value of the three measurements was taken.

CLSM General Image Process

Saos2 cells at the density of 1.5*10$^5$ were seeded onto a 3.5 cm confocal dish. After the growth of Saos2 cells in a cell incubator for 24 h, L-1P (or D-1P) at the designed concentration was added to the above solution with completed medium. After 1 h or 4 h, PBS was used to wash the Saos2 cells three times for one minute each wash. Hoechst 3342 was then used to stain the cell nucleus for 10 minutes, then the Saos2 cells were washed using live cell imaging three times for one minute each wash, keeping the Saos2 cells in the live cell imaging solution for CLSM immediately.

For staining the lysosome (or mitochondria), after the Saos2 cells were treated with L-1P (or D-1P) for 1 h or 4 h, the medium was removed from the confocal dish and the cells washed by PBS three times. Pre-warmed (at 37° C.) LysoTracker® (or Mito-Tracker®) containing medium was then added. The Saos cells were incubated for 1 h (for Mito-Tracker® 30 to 45 minutes is fine) under growth conditions. Then the staining solution was removed, and the cells were washed with live cell imaging solution three times. The cell nucleus was then stained using Hoechst 3342. Then the cells were washed with live cell imaging solution and imaged immediately by CLSM.

For endocytosis mechanism experiments, first the Saos2 cells were pre-incubated with different endocytosis inhibitors such as EIPA (100 µM, ethyl-isopropyl-amiloride), CPZ (30 µM, chlorpromazine), Filipin III (5 µg/mL), and M-βCD (5 mM) for 30 minutes. Then 50 µM of L-1P (or D-1P) was added to the confocal dish. After co-incubating the inhibitor with L-1P (or D-1P) for another 1 h, the culture medium was removed, and the Saos2 cells were washed by live cell imaging solution three times. Then the Saos2 cells were stained with Hoechst 3342 for 10 minutes, and washed with live cell imaging solution another three times, followed by CLSM immediately after.

Actin Staining

The procedure recommended by Molecular Probes™ (Thermo Fisher Scientific) for actin staining was used. The cells were seeded in a 3.5 cm confocal dish at $1.5 \times 10^5$ cells per dish. After incubating for 24 h, the culture medium was removed, and fresh medium added containing L-1P or D-1P for 4 h. After 4 h, the medium was removed and PBS was used to wash the cells three times. After fixing by 4% paraformaldehyde for 15 minutes, 1 mL of 0.1% Triton X-100 in PBS buffer was added for 30 minutes. After washing the cells three times with PBS, 1 mL of 0.1% BSA in PBS was added for 30 minutes, and the cells were washed with PBS three times. One mL of PBS containing 5 units of Alexa 633 was added to the cells for 1 h. After removing the staining solution and washing the cells three times with PBS, 1 mL of Hoechst (1 µg/mL) was added for 10 minutes. Then, the cells were washed three times with PBS buffer before imaging.

Apoptotic Signaling Assay

The assay was performed according to the procedure provided by Cell Signaling Technology, Inc. After the Saos2 cells grow to 80-90% confluence in 10 cm culture dish, the cells were treated with L-1P (or D-1P) at the desired time; untreated cells were used as a control. The culture medium was removed and the cells were washed 3 times with pre-cold PBS, then 0.5 ml ice-cold cell lysis buffer diluted with PBS to 1× its original concentration, plus protease inhibitors was added to each plate and the plate incubated on ice for 5 min. Then, the cells were scraped off the plate and transferred to a 1.5 mL tube. The collected cell fraction was freeze-thawed for three cycles. A microcentrifuge was used for 20 min (12,000 rpm) at 4° C. and the supernatant transferred to a new tube. The recovered supernatant is the cell lysate. The amounts of phosphorylated p53, p53, active Caspase3, active PARP, phosphorylated Bad and Bad were measured according to the manufactures instructions.

Time Dependent Western Blot

After the Saos2 cells reached to about 90% confluence in 10 cm culture dish, the culture medium was removed, and fresh culture medium was added that contains 50 µM L-1P (or D-1P) at different times. At desired time, the cells were collected (each time contains two 10 cm culture dish) by trypsin and centrifuged at 600 g for 5 minutes at 4° C. The Saos2 cells were washed with 5 mL of pre-cold PBS for two times, each time centrifuge at 600 g for 5 minutes and remove supernatant. The cells were re-suspended with 0.3 mL of cytosol extraction buffer containing DTT and protease inhibitors. The suspension was incubated on ice for 10 minutes. Then, cells were homogenized on ice and the homogenate transferred to a 1.5 mL tube, and centrifuged at 700 g for 10 minutes at 4° C. The supernatant was collect carefully and the pellet discarded. The supernatant was transfer to a fresh 1.5 mL tube and centrifuged for 30 minutes at 4° C. The supernatant was carefully transferred to a new 1.5 mL tube, this is the cytosolic fraction of Saos2 cells. Then, a bradford protein assay was used to quantify the concentration of protein and standard Western blot was preformed.

Example 1—Molecule Design and Synthesis

FIG. 1 shows the representative structure of the molecules designed for integrating EISA with mitochondria targeting. The molecules consist of four key features: a self-assembling backbone (i.e., a peptide containing D- or L-Phe-Phe-Tyr-Lys (FFYK), SEQ ID NO: 50), an enzymatic trigger (i.e., tyrosine phosphate ($_p$Y) as a substrate of ALP), an environment-sensitive fluorophore (4-nitro-2,1,3-benzoxadiazole (NBD)-β-Ala), and a mitochondria targeting motif (i.e., TPP). FFYK (SEQ ID NO: 50) was chosen because tyrosine provides a facile way to introduce the enzymatic triggers and FFY has acted as a motif for EISA (Gao et al., J. Am. Chem. Soc. 131:13576 (2009), which is hereby incorporated by reference in its entirety). NBD was used because NBD is a sensitive fluorophore for reporting molecular self-assembly in cellular milieu (Gao et al., Nat. Commun., 3:1033 (2012); Gao et al., Langmuir 29:15191 (2013); Zhou et al., J. Am. Chem. Soc. 137:10040 (2015); Gao et al., ACS Nano 7:9055 (2013), which are hereby incorporated by reference in their entirety). TPP was utilized because TPP is an efficient and well-established molecule for targeting the mitochondrial matrix (Smith et al., Proc. Natl. Acad. Sci. U.S.A 100:5407 (2003), which is hereby incorporated by reference in its entirety). To understand the effect of stability and stereochemistry of the peptides on the activity of the designed molecules, both L-amino acid residues and D-amino acid residues were used to form the peptide backbone. Such a design gives L-1P and D-1P as the precursors, and L-1 and D-1 as the self-assembling molecules. An acetyl group was used to replace TPP to generate L-2P and D-2P as the controls of L-1P and D-1P, respectively. Based on the design shown in FIG. 1, the cancer cells that overexpress ALP would generate the assemblies of the TPP-conjugates selectively on the cancer cells so that TPP only targets the mitochondria of cancer cells. It is expected that NBD, as an imaging probe, would help reveal the dynamic of the TPP assemblies during and after EISA of the TPP-conjugates on the cancer cells. NBD, however, could be eliminated from a final version of a therapeutic agent, or replaced with a suitable capping moiety that also facilitates peptide self-assembly (e.g., a naphthylacetyl moiety).

Figure 2:
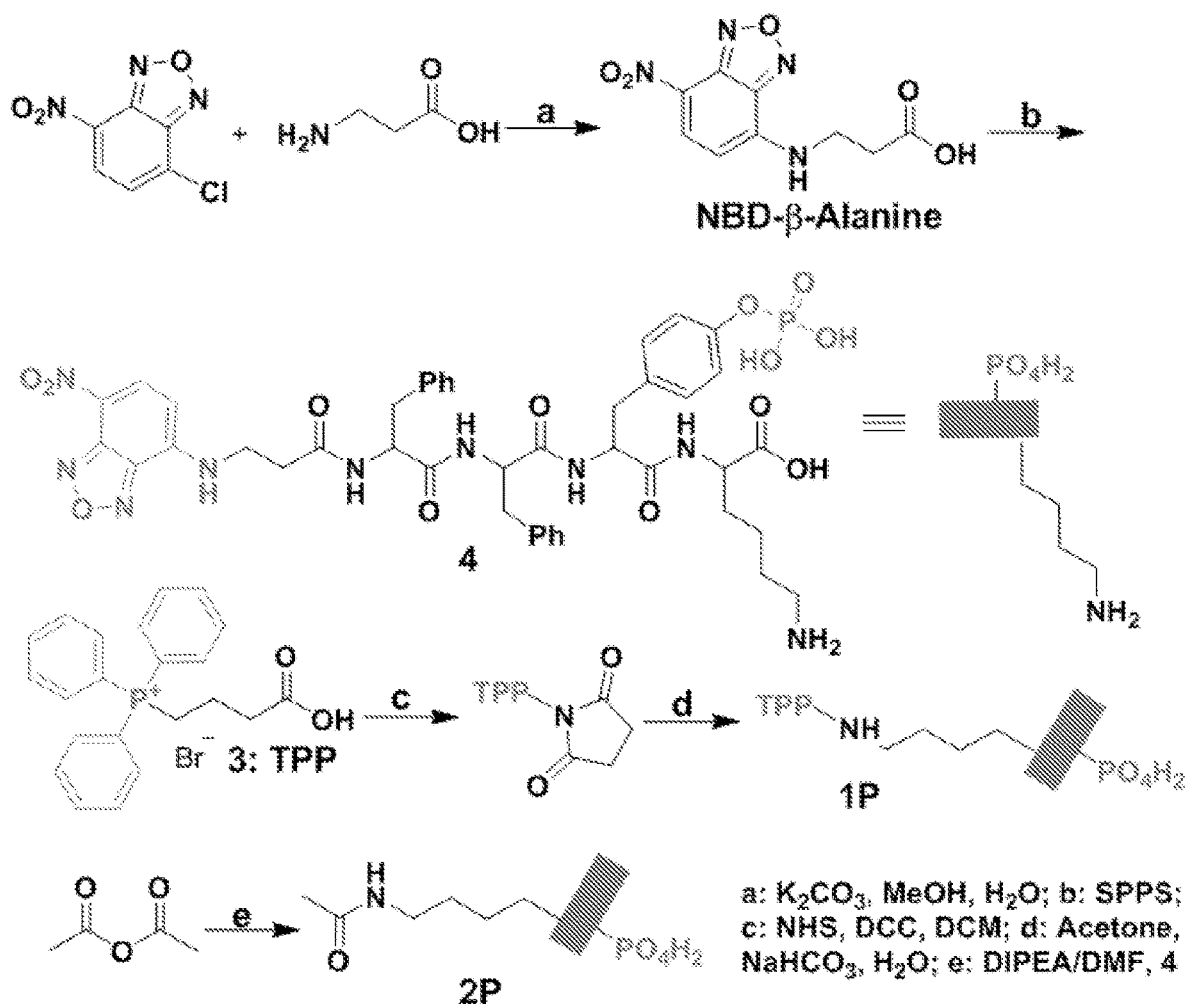
FIG. 2 shows the structures and the synthetic route of the peptide precursors containing phosphotyrosine NBD-β-Ala-Phe-Phe-pTyr-Lys (4, SEQ ID NO: 1) and 3-carboxypropyl-TPP (3), to form TPP-conjugated peptide hydrogelators, L-1P and D-1P, as well as the control molecules L-2P and D-2P (lacking TPP).

FIG. 2 shows a facile and general procedure for synthesizing the designed molecules. After using one step reaction of amine active NBD-Cl with β-alanine to produce NBD-β-alanine in over 90% yield and using Fmoc (9-fluorenyl-methoxycarbonyl) to protect phosphorylated tyrosine (Ottinger et al., *Biochemistry* 32:4354 (1993), which is hereby incorporated by reference in its entirety), NBD-BA-FF$_p$YK (L or D enantiomer) (SEQ ID NO: 1) was subsequently synthesized by standard solid-phase (Fmoc) peptide chemistry (Coin et al., *Nat. Protoc.* 2:3247 (2007); Wellings et al., *Methods Enzymol.* 289:44 (1997), which are hereby incorporated by reference in their entirety).

All the peptides were prepared by standard solid-phase peptide synthesis (SPPS) using 2-chlorotrityl chloride resin and the corresponding Fmoc-protected amino acids with side chains properly protected. The first amino acid was loaded onto the resin at about 0.6 mmol/g of resin. After loading the first amino acid to the resin, the capping regent (DCM:MeOH:DIPEA=17:2:1) was used to ensure all the active sites of the resin were protected. The solution of 20% piperidine in DMF was used to remove the Fmoc group, the next Fmoc-protected amino acid was coupled to the free amino group using HBTU as the coupling reagent. The growth of the peptide chain followed the established Fmoc SPPS protocol. The last capping group of NBD-β-Alanine was synthesized according to the reported method (Cai, Y. et al., *Anal. Chem.* 86, 2193 (2014), which is hereby incorporated by reference in its entirety). The crude peptides were collected using TFA-mediated cleavage method: The peptide derivative was cleaved using 95% of trifluoroacetic acid with 2.5% of TIS and 2.5% of H$_2$O for 1 h. 20 mL per gram of resin of ice-cold diethyl ether was then added to cleavage reagent. The resulting precipitate was centrifuged for 10 min at room temperature at 10,000 rpm. Afterward the supernatant was decanted and the resulting solid was use for the next step for synthesis.

100 mg of 3-carboxypropyl triphenylphosphonium bromide (TPP) was dissolved in 10 mL of dichloromethane (DCM), followed by 1.1 equiv. (29 mg) of N-Hydroxysuccinimide (NHS) and 57.6 mg of N,N'-dicyclohexylcarbodiimide (DCC) with catalytic amount of 4-dimethylamiopryidine were added. After being stirred at room temperature for 2 hrs, the solution was filtered through filter paper to remove precipitations. The filtrate was evaporated under reduced pressure to yield a white power, which was used directly for the next step. After the white powder obtained above being dissolved in 5 mL of N,N-dimethylformamide, 1.3 equiv. of corresponding peptide was then added with 3 equiv. N-diisopropylethylamine (DIPEA).

After N-hydroxysuccinimide (NHS) activates the carboxyl group of TPP, TPP-NHS ester reacts with NBD-βA-FF$_p$YK (SEQ ID NO: 1) via ε-amino group of lysine to form stable amide bonds to result in L-1P or D-1P.

Instead of TPP-NHS ester, the use of acetic anhydride to react with ε-amine of lysine produces the control precursors of L-2P and D-2P in a similar way (FIG. 2).

Specifically, acetic anhydride was used directly to react with peptide at the solution of DMF with DIPEA (adjusting pH to 8), after stirring at room temperature for 1 h, DMF was removed by air compressor, and methanol added to dissolve the product.

After purifying all the precursors by high-performance liquid chromatography (HPLC), $^1$H-NMR and LC-MS were used to confirm their purity and identity. Final products were purified by reverse-phase HPLC.

Example 2—Enzymatic Self-Assembly In Vitro

Figure 3:
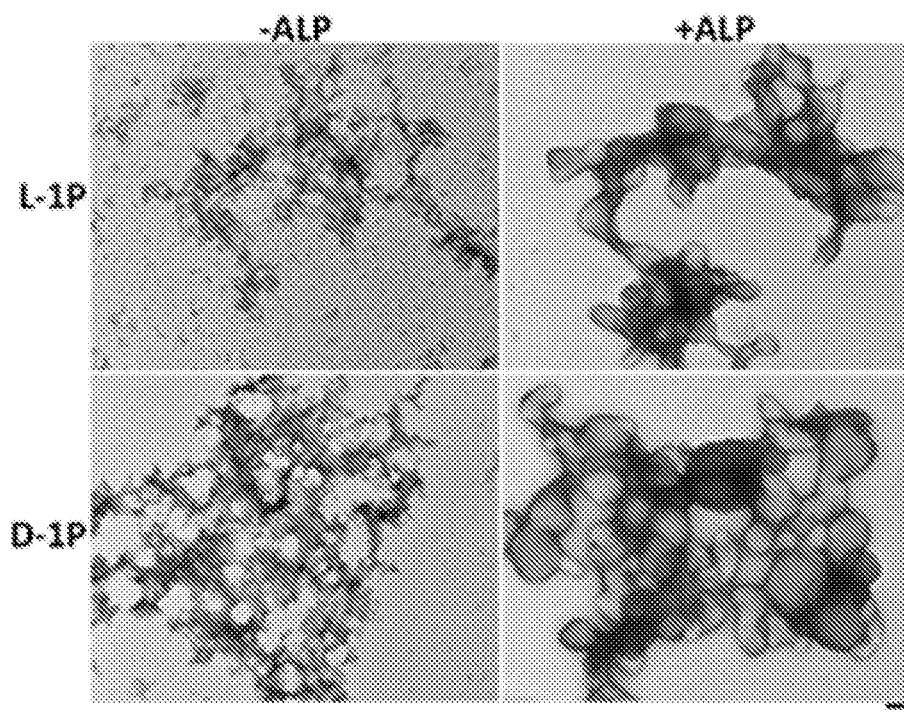
FIG. 3 shows TEM images of L-1P and D-1P (50 μM) in PBS buffer (pH 7.4) without or with ALP (1 U/mL) after 24 h.
Figure 4:
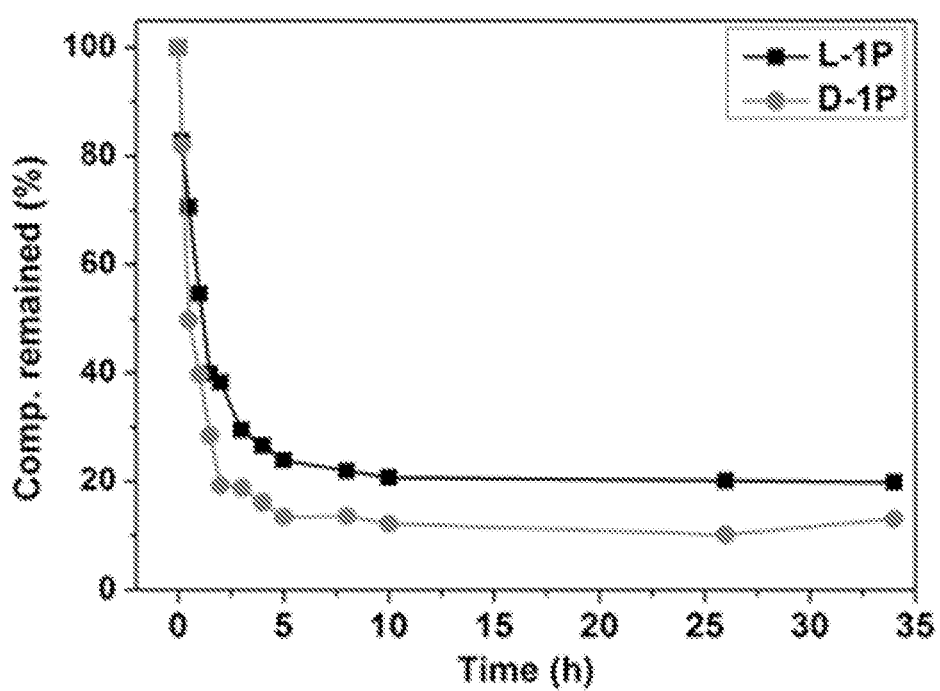
FIG. 4 shows the time-dependent dephosphorylation process of the precursors L-1P and D-1P at the concentration of 0.1 wt % treated with ALP (0.1 U/mL) at 37° C.
Figure 5:
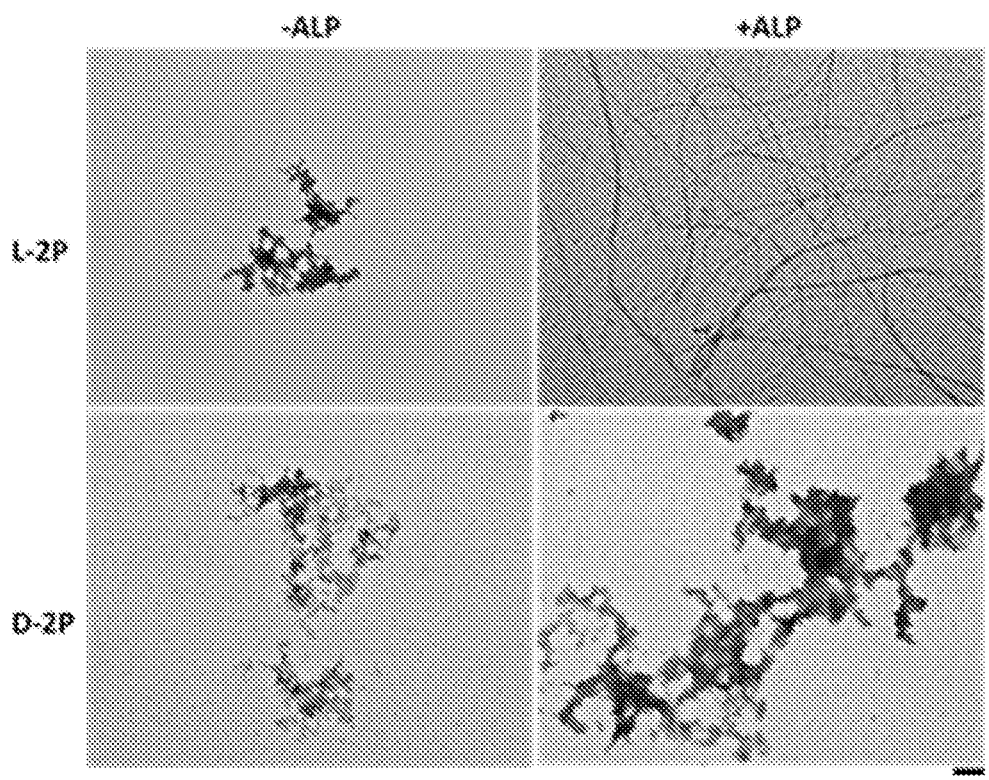
FIG. 5 shows TEM images of control molecules L-2P and D-2P (50 μM) in PBS buffer (pH 7.4) without or with ALP (1 U/mL) after 24 h.

After obtaining all the precursors in Example 1, their behaviors were evaluated for EISA in vitro by using TEM and static light scattering (SLS) to examine the nanostructures formed before and after the addition of ALP into the solutions of the precursors. After drying from solution, L-1P (50 µM) shows many tiny nanoparticles with diameter of 5±2 nm, which tend to aggregate to result in irregular fibrous structures with diameter of 7±2 nm (FIG. 3), while at higher concentration, L-1P (100 µM) mainly forms irregular fibrous structure with few oligomers. As a contrast, D-1P (50 µM) forms slightly more regular fibrous structures with diameter of 8±2 nm, which then interact with each other to form dense 2D/3D networks. Interestingly, D-1P (100 µM) forms more uniform nanoparticles with diameter of 25±2 nm. As revealed by the dephosphorylation experiment (FIG. 4), D-1P undergoes ALP catalyzed dephosphorylation slightly faster than L-1P does. The $t_{1/2}$ was determined to be 0.55 h and 1.14 h for D-1P and L-1P, respectively, when the substrate is present at a 0.1 wt % and ALP is 0.1 U/mL. After 24 h, the percentages of enzymatic dephosphorylation of D-1P and L-1P are about 90% and 80%, respectively. The percentage of conversion changes a little with prolonged incubation, suggesting that the nanostructures formed mainly by L-1 (or D-1) likely incorporate the precursors to hinder their complete dephosphorylation. After being formed by dephosphorylation, L-1 and D-1 form different nanostructures. TEM indicates that, after being generated by treating L-1P with ALP (1 U/mL), L-1 (50 µM) forms vesicles that interact with each other strongly, which gives hollow colloids with a mean diameter of 79±2 nm and the thickness of 4±2 nm. Similar to L-1, D-1 forms aggregated hollow colloids with a larger mean diameter (106±2 nm) and slightly thicker layers (thickness of 6±2 nm). L-2P or D-2P (50 µM) forms amorphous aggregates after dissolving in PBS buffer (pH=7.4) (FIG. 5). While the addition of ALP converts L-2P to L-2 to form uniform nanofibers with diameter of 9±2 nm, the enzymatic conversion of D-2P to D-2 results in nanoscale aggregates with diameter of 16±2 nm. These results suggest that the TPP motif likely causes the morphology of the nanostructures of L-1P/D-1P to differ significantly from those of L-2P/D-2P. As a charged, steric-hindered motif being connected to the peptide backbone via a relatively flexible linker, TPP disrupts intermolecular packing to disfavor the formation of long nanofibers, but it promotes interparticle interaction to favor polymorphic aggregates before and after enzymatic dephosphorylation. Such a plasticity of the assemblies of small molecules may be useful to reduce the acquired drug resistance if the assemblies are cytotoxicity species (vide infra).

Figure 6:
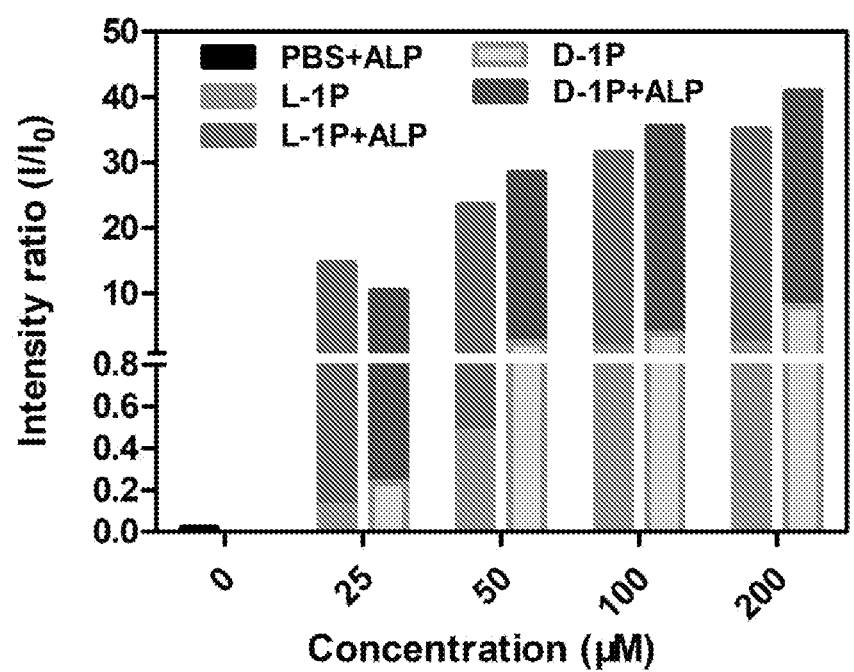
FIG. 6 is a graph showing the intensity of static light scattering (SLS) of the solutions of L-1P and D-1P (25-200 μM) before and after adding ALP (1 U/mL) for 24 hours at different concentrations in PBS buffer (pH 7.4).

To further evaluate the self-assembly properties of precursors before and after the addition of ALP, SLS was used to examine the signal changes of the precursor before and after the enzymatic dephosphorylation (FIG. 6). The solution of L-1P (or D-1P) exhibits enhanced signal with the increase of concentration (from 25 µM to 200 µM). This result indicates that both precursors are able form aggregates to some extent, agreeing with the results of TEM. After the addition of ALP to the solution of each precursor, the SLS signal increases significantly, up to more than ten-fold. Depending on the initial concentrations of the precursors, the increase of the SLS signals of L-1P is 120 fold (25 µM), 48 fold (50 µM), 18 fold (100 µM) and 14 fold (200 µM), while D-1P is 43 fold (25 µM), 10 fold (50 µM), 8 fold (100 µM) and 4 fold (200 µM). These results confirm that L-1P and D-1P are the excellent precursors for EISA based on ALP.

Example 3—Cytotoxicity and Selectivity

To investigate the cellular response to all the precursors, an MTT (3-(4,5-dimethylthiazol-2-yl)-2,5-diphenyl tetrazolium bromide) assay (Gerlier et al., *J. Immunol. Methods* 94:57 (1986), which is hereby incorporated by reference in its entirety) was first used to examine the viability of human osteosarcoma cells (Saos2, which expresses high level ALP (Farley et al., *Metabolism* 40:664 (1991), which is hereby incorporated by reference in its entirety)) cultured with the precursors. As a control, the viability of normal human bone marrow stromal cells (HS5) that express low level of ALP on cell surface was also examined (Zhou et al., *Chem* 1:246 (2016), which is hereby incorporated by reference in its entirety). As shown in FIG. 7, L-1P exhibits $IC_{50}$ of 61±2 µM (76.1±2.5 µg/mL, 48 h) against Saos2 cells in a dosage dependent manner. D-1P exhibits $IC_{50}$ of 46±2 µM (57.4±2.5 µg/mL, 48 h), lower than the $IC_{50}$ of L-1P. In the presence of exogenous ALP, L-1P (or D-1P) turns into L-1 (or D-1), which is innocuous to Saos2 cells at the concentrations up to 200 µM. This result confirms that L-1 (or D-1), if not being generated in-situ on the cancer cell surface, is innocuous to the cells. As another control, L-2P (or D-2P) by itself or co-incubated with the targeting motif TPP (3) hardly exhibits cytotoxicity against Saos2 cell, even at 500 µM (FIG. 7). This result indicates that the conjugation of TPP to the self-assembling peptide is responsible for the observed cytotoxicity. To investigate the retention of L-1 (or D-1) in the Saos2 cells, the cells were incubated with L-1P (D-1P, 50 µM) for different times. The result indicates that the intracellular concentration of L-1 increases over the first 6 h, and then decreases with the longer incubation time (FIG. 8A). On the contrary, the concentration of D-1 decreases little after 6 h incubation. Moreover, the intracellular concentration of D-1 is 3.5 fold of that of L-1 at 6 h incubation, but the ratio increases to 10 fold at 24 h incubation (FIG. 8B). This result agrees with the proteolytic stability of D-1, which is consistent with the higher cytotoxicity of D-1P than that of L-1P.

Figure 9A:
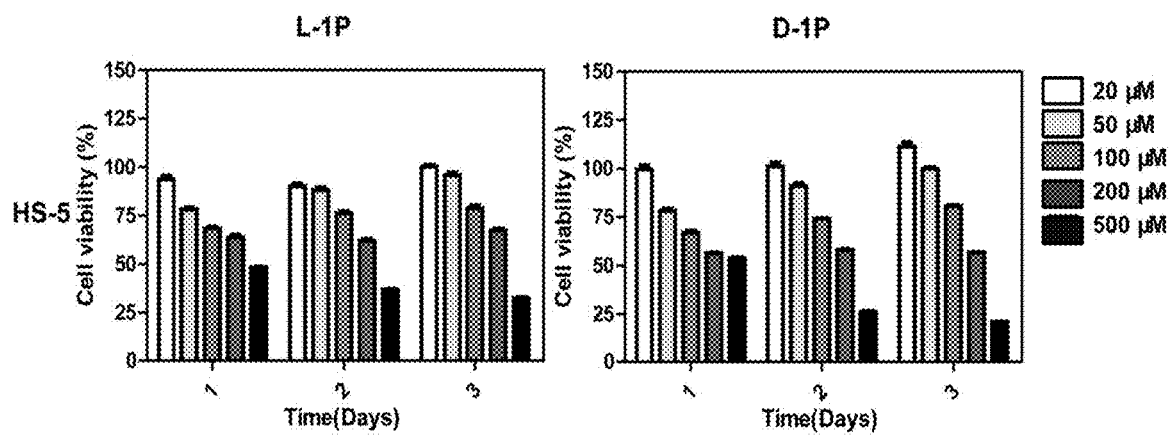
FIGS. 9A-B each contain a pair of graphs showing the viability of HS-5 cells (FIG. 9A) or HeLa cells (FIG. 9B) independently treated with various concentrations of L-1P and D-1P (from 20 μM to 500 μM). Cell viability is shown at 24, 48 and 72 h following treatment with 200 μM of L-1P or D-1P.
Figure 9B:
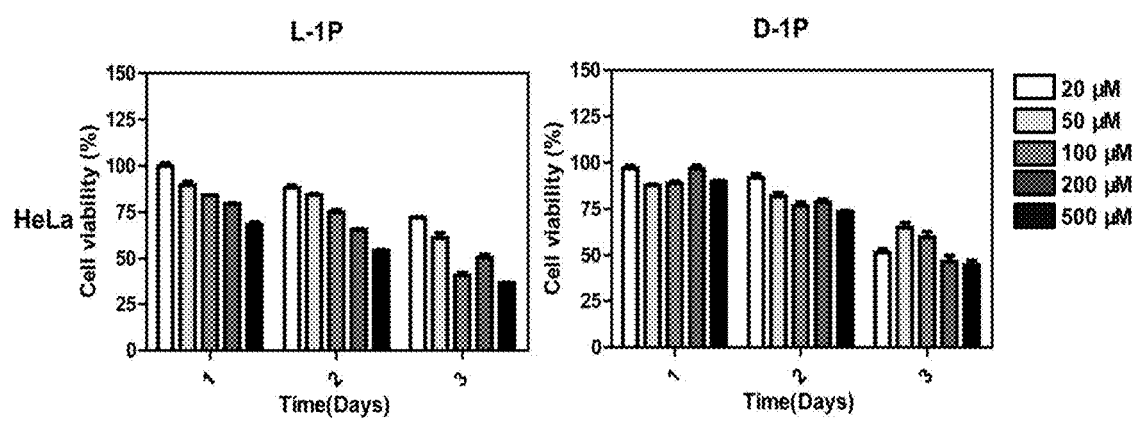
Figure 10A:
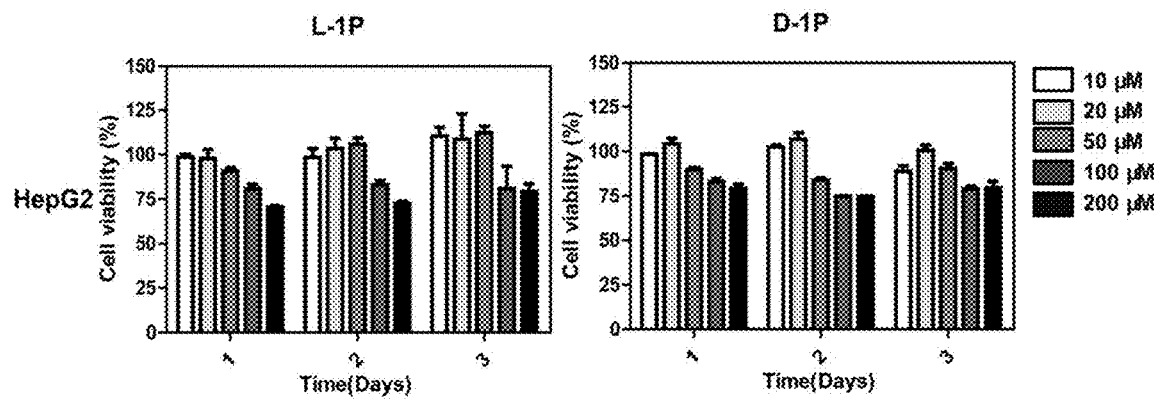
FIGS. 10A-C each contain a pair of graphs showing the viability of HepG2 cells (FIG. 10A), T98G cells (FIG. 10B) and MCF-7 cells (FIG. 10C) treated independently with various concentrations of L-1P and D-1P (from 20 μM to 500 μM). Cell viability is show at 24, 48 and 72 h following treatment.
Figure 10B:
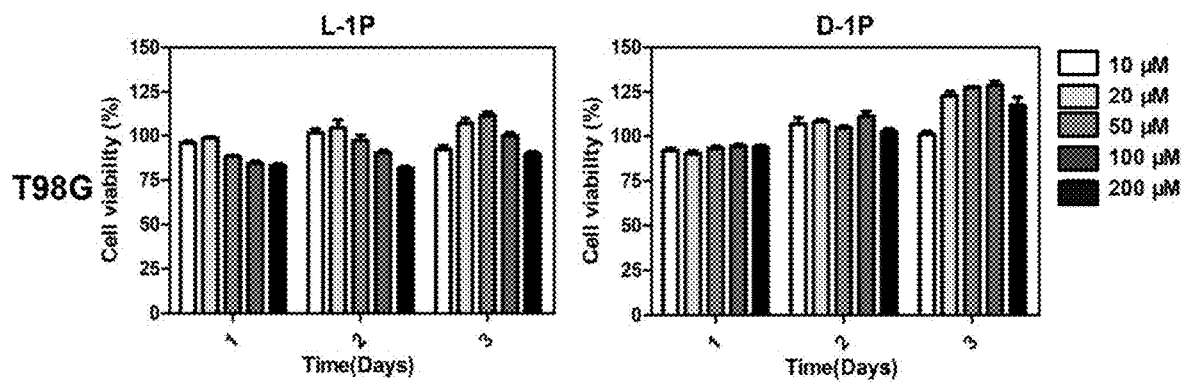
Figure 10C:
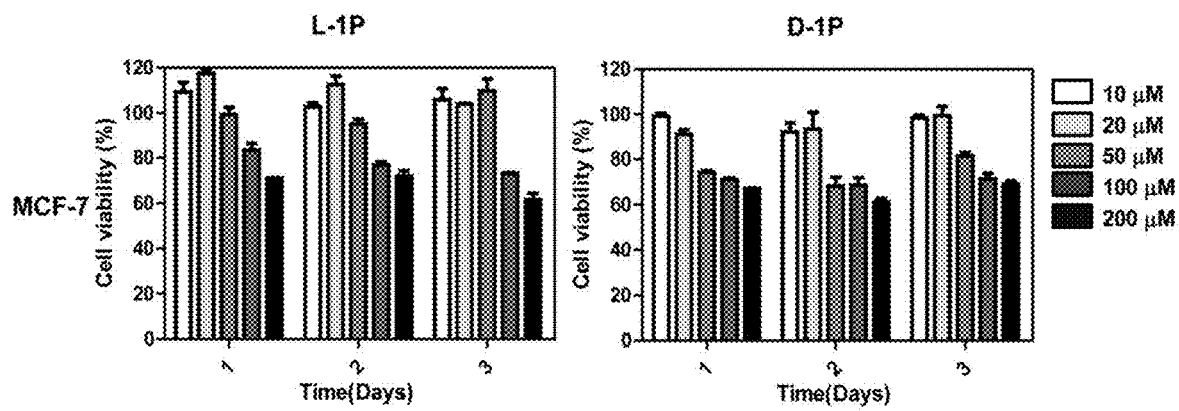

The cytotoxicity of L-1P and D-1P against HS5 cells was also examined. The results indicate that L-1P (or D-1P) is almost innocuous to HS5 cells at 100 µM, the concentrations that kill over 90% of Saos2 cells (compare FIG. 9A to FIG. 7). To evaluate whether the precursors inhibit other cancer cell lines that express low levels of ALPs, L-1P (or D-1P) was incubated with HeLa (human cervical adenocarcinoma cell line), HepG2 (human liver carcinoma cell line), T98G (glioblastoma multiforme tumor cell line), and MCF7 (human breast adenocarcinoma cell line). Expressing lower level of ALPs on their cell surfaces than on Saos2 cell surface, these cells are less susceptible than Saos2 cell to L-1P (or D-1P). That is, the $IC_{50}$ of L-1P (or D-1P) against these cells are higher than 200 µM (FIGS. 9B, 10). At 200 µM, L-1P and D-1P, exhibit similar cytotoxicities against HeLa, HepG2 or MCF7 cells at 48 h (FIGS. 9B, 10). Interestingly, D-1P is slightly less cytotoxic than L-1P against T98G cells. This difference may originate from the difference in stereochemistry and may deserve further investigation in future work. These results, together with TEM and SLS results, indicate that the integration of cell targeting (by EISA) and mitochondria targeting (by TPP) is an efficient combinedstrategy for selectively inhibiting the cancer cells that express high level of ALP (McComb et al., "Alkaline Phosphatase," *Springer Science & Business Media* (2013), which is hereby incorporated by reference in its entirety).

Example 4—Escaping from Lysosome and Targeting Mitochondria

Figure 11:
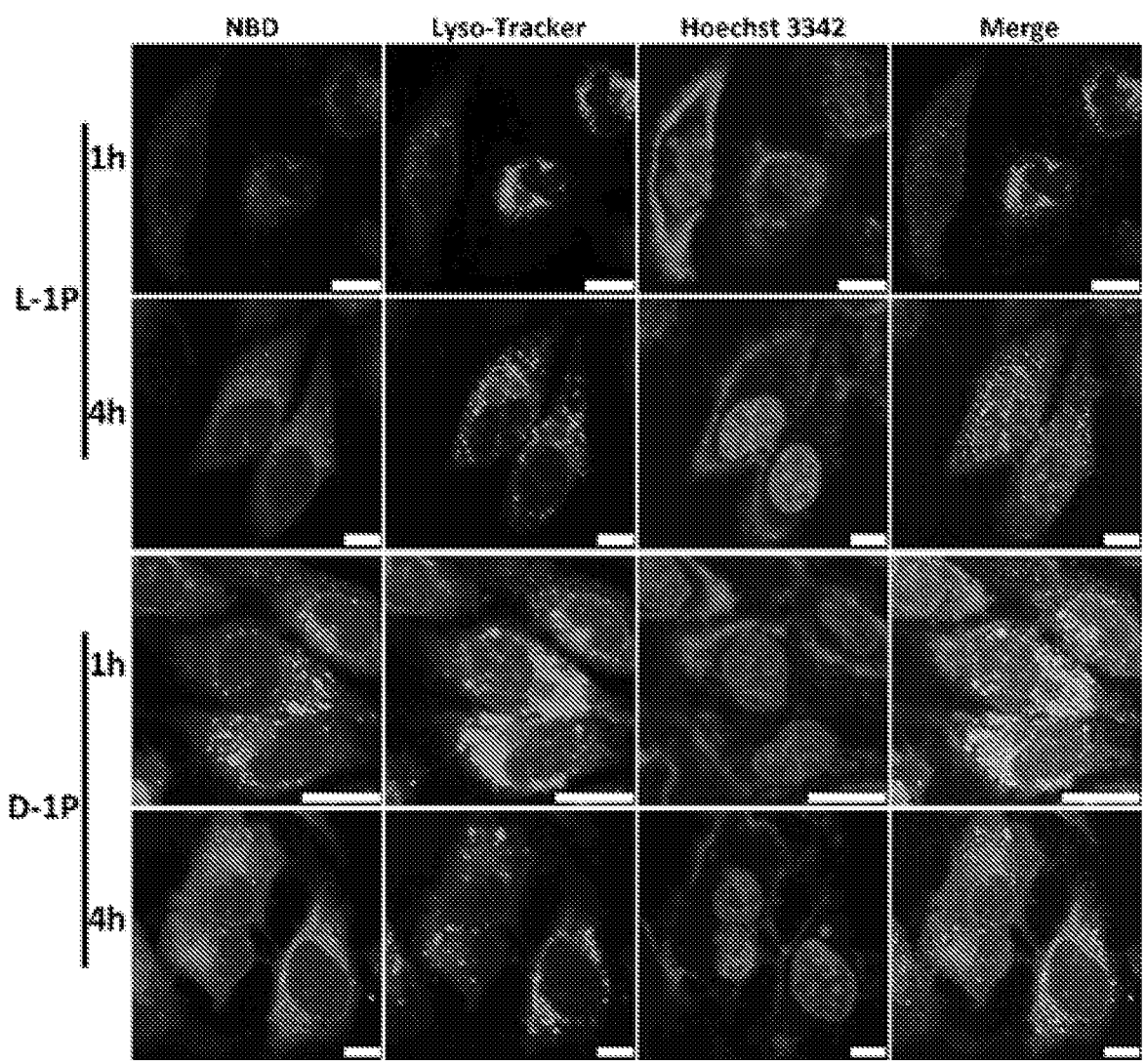
FIG. 11 is a panel of confocal laser scanning microscopy (CLSM) images showing Saos2 cells treated with L-1P or D-1P (50 μM) for 1 or 4 h and then stained with Lyso-Tracker®. The scale bar is 10 μm.

Confocal laser scanning microscopy was used to examine the intracellular localization of L-1 and D-1 in Saos2 cells. As shown in FIG. 11, most of the NBD fluorescence (from L-1 or D-1 in the Saos2 cells; green in color versions of figure) co-localize with the Lyso-Tracker® fluorescence (red in color versions of figure (Zhou et al., *Nature* 469:221 (2011) which is hereby incorporated by reference in its entirety)) within 1 h, indicating the uptake of L-1 (or D-1) by cells via endocytosis (Subach et al., *Nat. Chem. Biol.* 5:118 (2009), which is hereby incorporated by reference in its entirety). However, there is little overlap of the fluorescence between NBD and LysoTracker® signals after 4 h incubation, indicating that the assemblies of L-1 (or D-1) escape from late endosome/lysosome into cytosol. The escape of peptidic derivatives from endosome/lysosome is the first report of such phenomenon (Lock et al., *J. Am. Chem. Soc.* 138:3533 (2016), which is hereby incorporated by reference in its entirety), and certainly was not expected.

Figure 12:
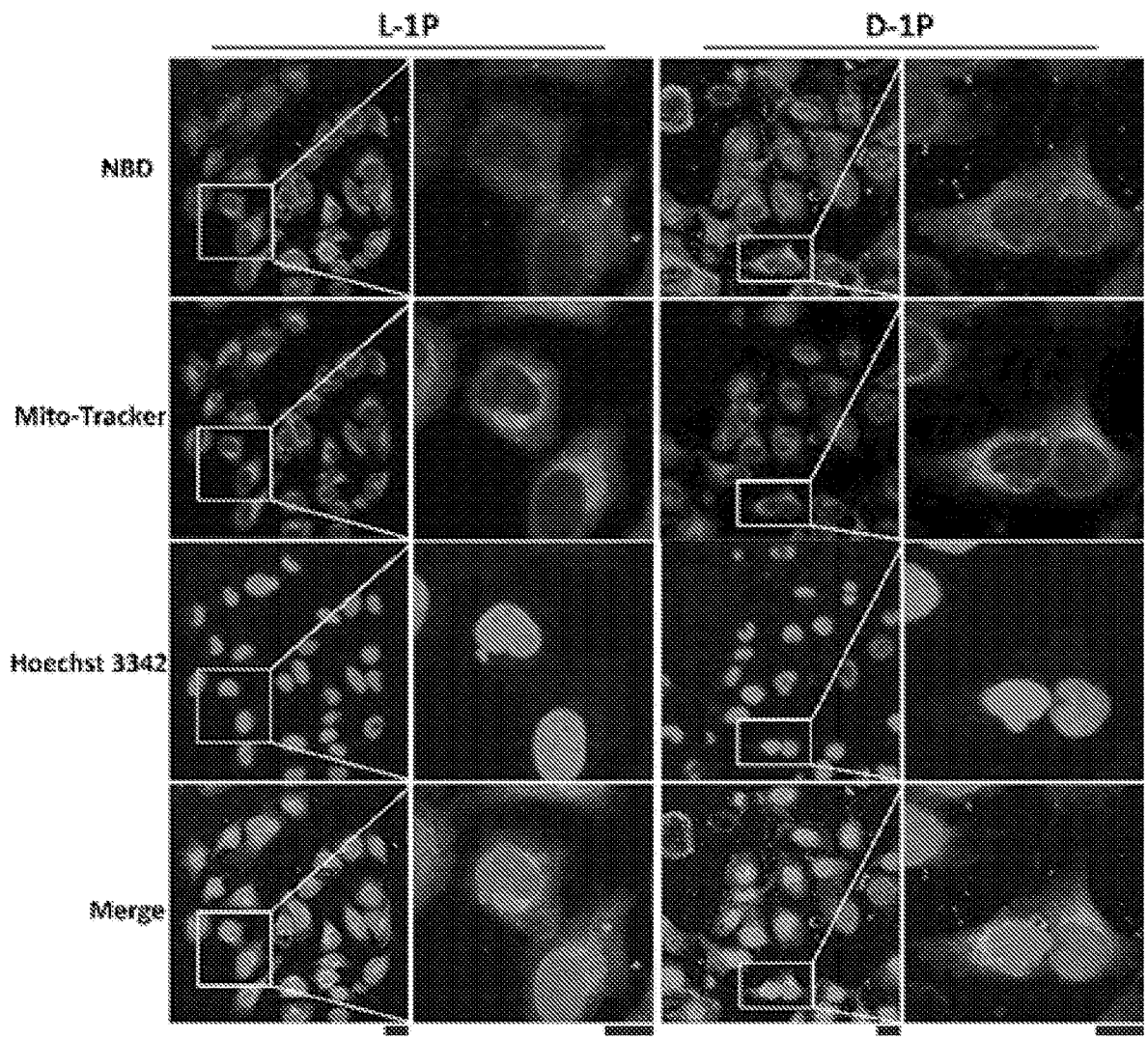
FIG. 12 is a panel of CLSM images showing Saos2 cells treated with L-1P or D-1P (50 μM) for 4 h, and then stained with Mito-Tracker®. The scale bar for low magnification is 25 μm and higher is 15 μm.

To further evaluate the cellular distribution of L-1 (or D-1) after its in-situ formation, Mito-Tracker® was used to co-stain with all the precursors (Shim et al., *Proc. Natl. Acad. Sci. U.S.A.* 109:13978 (2012), which is hereby incorporated by reference in its entirety). As shown in FIG. 12, the fluorescence signal from NBD (green in color versions) co-localizes well with the fluorescence signal from the Mito-Tracker® (red in color versions) in the cytosol after co-incubation for 4 h. Moreover, the NBD fluorescence on the cell surface indicates that the assemblies of L-1 (or D-1) not only enter the cell to target mitochondria, but also self-assemble on the cell surface, as demonstrated by 3D construction of confocal images. These results indicate that L-1P (or D-1P) induces cancer cell death likely via three key processes (FIG. 1):

i) L-1P (or D-1P) itself forms oligomers at certain concentration, which then interact with each other to form nanoscale assemblies.

ii) ALPs on the Saos2 cell surface, being expressed in high level, catalyze the rapid dephosphorylation of L-1P (or D-1P) for generating of L-1 (or D-1) (i.e., EISA occurs on the cancer cell surface (Kuang et al., *Angew. Chem., Int. Ed.* 53:8104 (2014), which is hereby incorporated by reference in its entirety)). The process of EISA further induces the assemblies of L-1 (or D-1) on cell surface, which then are internalized by the cancer cells through endocytosis.

iii) The internalized assemblies of L-1 (or D-1) escape from late endosome/lysosome, and then target mitochondria because of TPP. Unlike monomeric TPP that rescues cells (Mukhopadhyay et al., *Adv. Drug Delivery Rev.* 59:729 (2007), which is hereby incorporated by reference in its entirety), the assemblies (or aggregates) of the TPP-peptide conjugate function as multivalent TPPs, which enhance the disruption of the mitochondria. That is, the dynamic transport of the assemblies on cell surface to the surface of mitochondria is what ultimately kills the cancer cells.

Because HS5 expresses low levels of ALP, L-1P (or D-1P) is inefficient for undergoing EISA, thus L-1P (or D-1P) exhibits little toxicity to HS5 cells.

Example 5—Modes of Endocytosis

To examine the modes of endocytosis that involve the uptake of the TPP-peptide conjugates by the Saos2 cells, the Saos2 cells were incubated with L-1P (or D-1P, 50 µM) at 4° C. because all endocytic pathways are energy dependent processes that slow down at low temperature (Rejman et al., *Biochem. J.* 377:159 (2004); Gump et al., *Trends Mol. Med.*, 13:443 (2007), which are hereby incorporated by reference in their entirety). As revealed by the results of co-localization experiment, L-1P/L-1 (or D-1P/D-1) hardly enters the cells or associates with cell membranes at 4° C., confirming that the internalization of L-1 (or D-1) is energy-dependent.

To determine which kinds of endocytotic process are responsible for the uptake, several well-established endocytotic inhibitors were used to co-incubate with L-1P (or D-1P) in the culture of Saos2 cells. As shown in FIG. 13, the addition of 5-(N-ethyl-N-isopropyl)-amiloride (EIPA), an inhibitor of macropinocytosis and phagocytosis in most mammalian cells (Nakase et al., *Mol. Ther.* 10:1011 (2004), which is hereby incorporated by reference in its entirety), hardly affects the uptake of L-1 (or D-1). The addition of chlorpromazine (CPZ), a cationic amphipathic drug that inhibits clathrin mediated endocytosis (Inal et al., *Exp. Cell Res.* 310:54 (2005), which is hereby incorporated by reference in its entirety), reduces the uptake of L-1 for about 15% and D-1 for about 45% (according to the quantification of intracellular fluorescence of NBD obtained by CLSM). The additions of Filipin III and M-$\beta$CD, inhibitors of lipid raft/caveolae mediated endocytosis (Smart et al., *Methods Enzymol.* 353:131 (2002); Ros-Bare) et al. *Proc. Natl. Acad. Sci. U.S.A.* 98:12050 (2001); Monis et al., *Am. J. Pathol.* 169:1939 (2006), which are hereby incorporated by reference in their entirety), significantly affect the uptake of L-1 and D-1. Specifically, Filipin III reduced the uptake of L-1 and D-1 by about 55% and 64%, respectively. M-$\beta$CD reduced the uptake of L-1 and D-1 by about 86% and 72%, respectively. These results indicate that, after being generated by the dephosphorylation of L-1P (or D-1P) the assemblies of L-1 or D-1 mainly undergo caveolae/lipid-raft mediated endocytosis (Ostrom et al., *Br. J. Pharmacol.* 143:235 (2004), which is hereby incorporated by reference in its entirety) along with a limited extent of clathrin mediated endocytosis (Sigismund et al., *Proc. Natl. Acad. Sci. U.S.A.* 102:2760 (2005), which is hereby incorporated by reference in its entirety).

Example 6—Mechanism of Cell Death

To demonstrate the essential role of EISA for its anticancer activities, the precursor and the ALP inhibitors were co-incubated during cell viability experiments. Three kinds of established ALP inhibitors were used: L-phenylalanine (L-Phe) (Borgers, M. J., *Histochem. Cytochem.* 21:812 (1973), which is hereby incorporated by reference in its entirety), an efficient uncompetitive inhibitor of placental alkaline phosphatase (PLAP) levamisole, a well-known uncompetitive inhibitor of tissue-nonspecific alkaline phosphatase (TNAP) (Borgers, M. J., *Histochem. Cytochem.* 21:812 (1973), which is hereby incorporated by reference in its entirety) and CinnGEL 2Me (Zhu et al., *Cancer Res.* 67:10129 (2007), which is hereby incorporated by reference in its entirety), an inhibitor of protein tyrosine phosphatase (PTP1B) that localizes at the cytoplasmic face of the endoplasmic reticulum. As shown in FIG. 14A, co-incubating the precursors with L-Phe or CinnGEL 2Me hardly rescues the Saos2 cells, while levamisole increases the cell viability of Saos2 cells treated by L-1P or D-1P (even at the concentration as high as 200 µM). To be specific, the cell viability of Saos2 cells in the presence of L-1P or D-1P, respectively, increases from 21.6% or 11.5% to 65.3% or 66.0% at the concentration of 100 µM for 48 h, and from 2.1% or 1.8% (indicating that almost all the cells are dead) to 50.5% or 53.3% at the concentration of 200 µM for 48 h. These results are consistent with the expression levels of isoforms of ALPs on Saos2 cells, which express more TNAP than PLAP on the cell surface (Zhou et al., *J. Am. Chem. Soc.* 138:3813 (2016); Millán, J. L., "Mammalian Alkaline Phosphatases: From Biology to Applications in Medicine and Biotechnology," John Wiley & Sons (2006), which are hereby incorporated by reference in their entirety). Moreover, the PTP1B inhibitor (i.e., CinnGEL 2Me) is unable to rescue the cells, supporting the mechanism in FIG. 1 that EISA on the cell surface is the key processes for converting L-1P and D-1P to L-1 and D-1, respectively. To further confirm the role of ALPs on cell surface, the precursors were incubated together with ALP, which serves as an exogenous enzyme. The addition of ALP almost eliminates the cytotoxicity of the precursors. Thus, these results confirm that the process of EISA on cell surface plays an important role for the activity of the precursors, which further influences the uptake of the assemblies of L-1 or D-1.

To understand how the process of EISA on cell surface influences the uptake of L-1 (or D-1), a confocal microscope was used to detect the uptake of L-1 (or D-1) in the presence of different inhibitors of ALPs. As shown in FIG. 14B, Saos2 cells exhibit similar fluorescence without and with the presence of L-Phe, indicating that L-Phe hardly hinders the uptake of L-1 (or D-1). This result agrees that most of the ALPs on Saos2 are TNAPs. On the contrary, cells treated by the precursors with levamisole or exogenous ALPs show much weaker fluorescence than the control cells (only being incubated with the precursors). These results, therefore, confirm that the EISA, as a process, is critical for the uptake of L-1 (or D-1). In other words, when the inhibitor of ectoenzyme (TNAPs) or the presence exogenous ALPs blocks or disrupts the process of EISA, the precursors are unable to turn into the assemblies of L-1 or D-1 on the cancer cell surface, thus further hampering the uptake of the aggregates, so Saos2 cells remain viable, as shown in the MTT assay (FIG. 14A). This detailed exploration of EISA on Saos2 cell surface also illustrates a way of modulating EISA on other cells for controlling the behavior of the cells.

Figure 15:
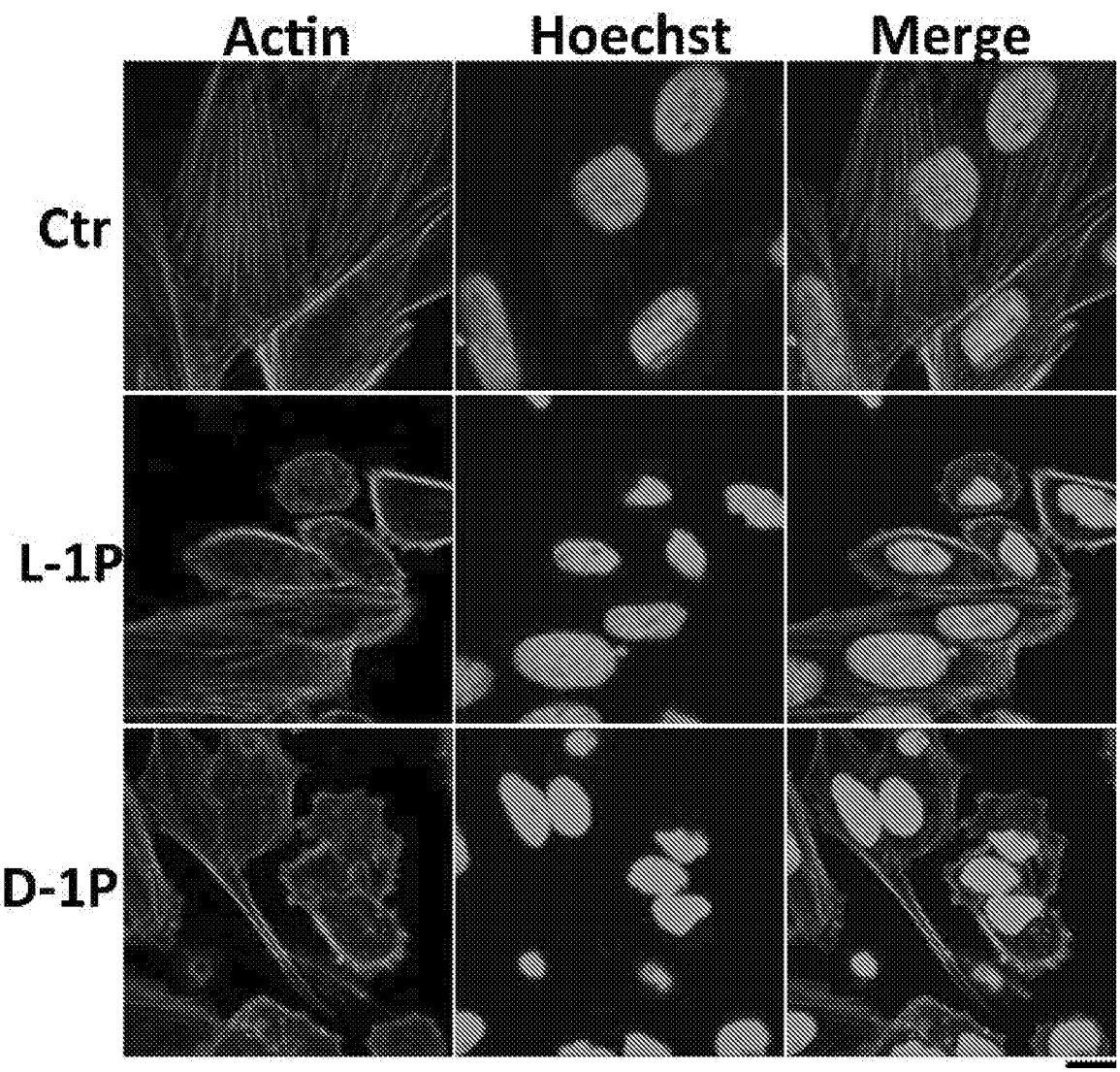
FIG. 15 is a panel of CLSM images showing Saos2 cells stained with Alexa Fluor 633 phalloidin (F-actin, red in color version) and Hoechst (nuclei, blue in color version) without or with the addition of L-1P or D-1P (100 μM) for 1 h (scale bar is 15 μm).

The endocytotic mechanism of the assemblies of L-1 (or D-1) and the presence of some fluorescence puncta on the Saos2 cell surface prompted the examination of the changes of the cytoskeleton of the Saos2 cells. Alexa Fluor 633 phalloidin was used (Eiseler et al., *Nat. Cell Biol.* 11:545 (2009), which is hereby incorporated by reference in its entirety), which induces specific staining of actin cytoskeleton to reveal the changes of actin filament. As shown in FIG. 15, the actin filaments in the control Saos2 cells (untreated cells) exhibit well-arranged parallel structures with long and thick fibers. After the cells were treated with L-1P (or D-1P) for 1 h at the concentration of 100 µM, some of the actin filaments become disorganized, aggregating into short and ill-defined fibers and puncta. In addition, there are more puncta in the cells treated by D-1P than in those treated by L-1P. These results indicate that the impaired actin cytoskeletons, caused by aggregates of L-1 (or D-1), contribute to the cell death. This observation implies that EISA on the cell surface not only is the key process for the subcellular targeting of mitochondria by the aggregates formed by L-1 (or D-1), but also is one of the key contributions for interacting with the cytoskeleton, which likely influences the dynamic of cell membrane, enhances the uptake of aggregates, and results in effective anticancer activity.

Example 7—Modality of Cell Death

Figure 16:
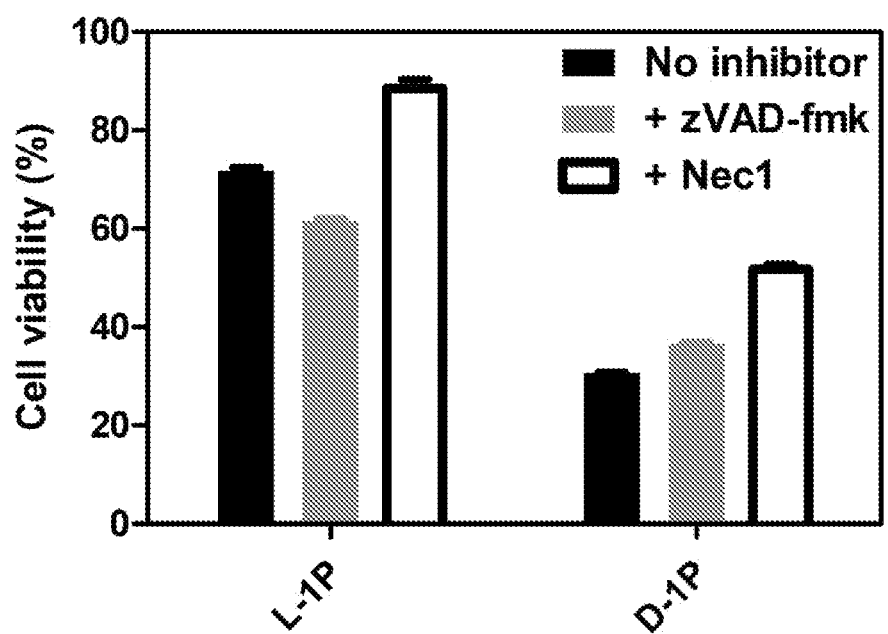
FIG. 16 is a graph showing cell viability of Saos2 cells treated by L-1P or D-1P (50 μM) in the presence of cell death signaling inhibitors at 48 h ([zVAD-fmk]=45 μM, [Nec-1]= 50 μM).

To evaluate the modality of cell death induced by L-1P (or D-1P), Saos2 cells were co-incubated with a pan-caspase inhibitor (zVAD-fmk) (Huijun et al., *Biochem. J.* 315:21 (1996), which is hereby incorporated by reference in its entirety), or a necroptosis inhibitor (Nec-1) (Degterev et al., *Nat. Chem. Biol.* 1:112 (2005), which is hereby incorporated by reference in its entirety) with the precursors. As shown in FIG. 16, zVAD-fmk (45 µM), which itself shows no toxicity on Saos2 cells, hardly rescues the cells but exhibits a little more toxicity when co-incubated with L-1P (50 µM) for 48 h. However, it can rescue Saos2 cells when it was co-incubated with D-1P. Notably, Nec-1 can reduce the toxicity of L-1P (or D-1P) to some extent. These results indicate that L-1P (or D-1P) induces cell death involving more necroptosis than apoptosis. Since Nec-1 is unable to rescue the cells fully, other mechanisms likely also contribute the death of Saos2 induced by the addition of L-1P (or D-1P).

Example 8—Apoptotic Signaling Induced by the Assemblies of L-1 (or D-1)

Figure 17:
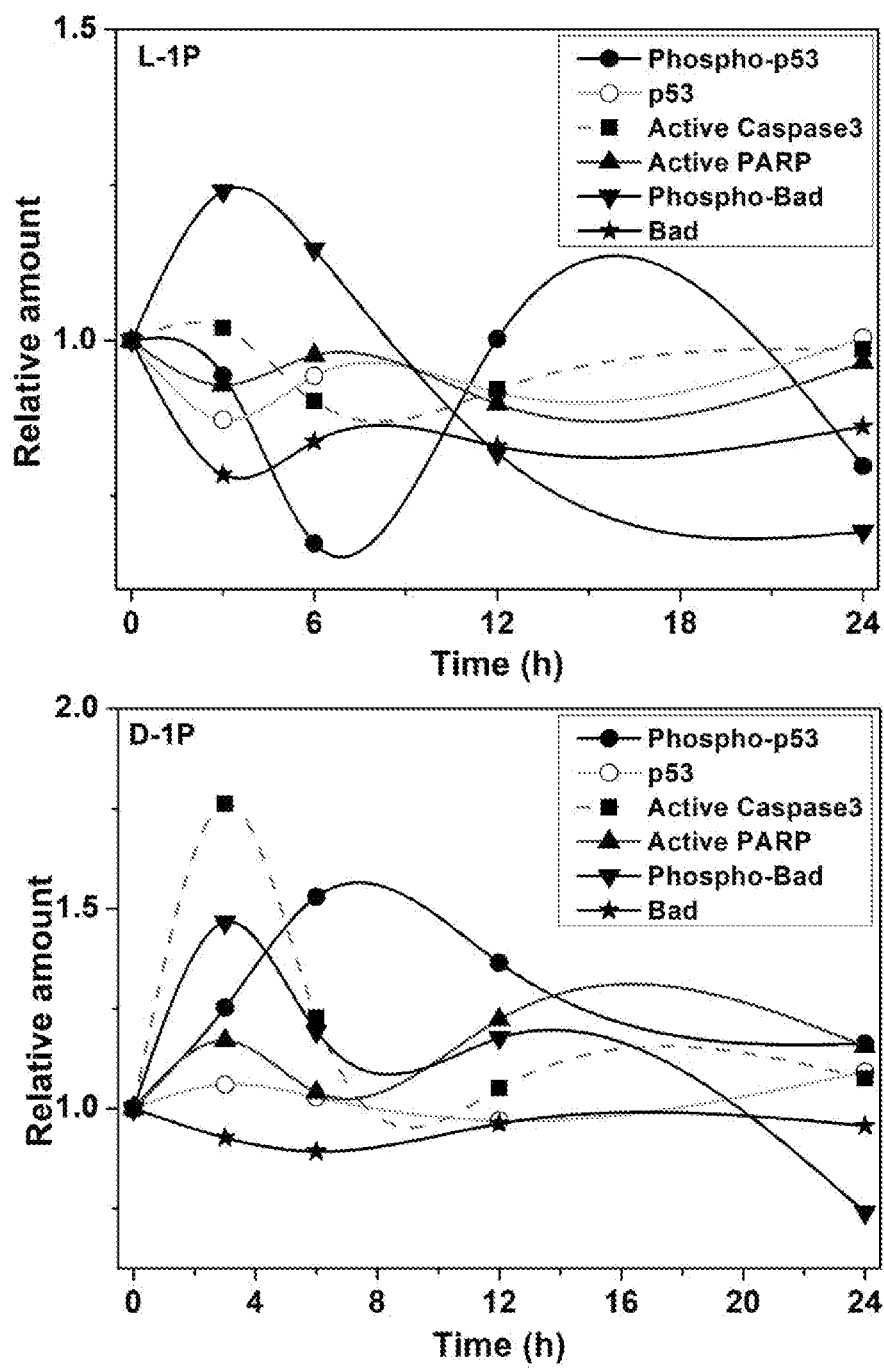
FIG. 17 is a pair of graphs showing the time-dependent activation of apoptotic proteins in Saos2 cells treated with L-1P or D-1P (50 μM).

To gain insight into the mechanism of Saos2 cell death induced by L-1P (or D-1P), a PathScan® apoptosis multi-target sandwich ELISA was used to detect the changes of endogenous level of key signaling proteins in pathways controlling survival and apoptosis (Budihardjo et al., *Annu. Rev. Cell Dev. Biol.* 15:269 (1999); Li et al., *Nature* 396:580 (1998), which are hereby incorporated by reference in their entirety). As shown in FIG. 17, the expression level of phosphorylated p53 decreases a slightly over the first 6 h and increases after 12 h incubation with L-1P, while the Saos2 cells treated with D-1P express high levels of phosphorylated p53 with extended incubation time to 8 h. The phosphorylated p53 level then decreases to a relatively constant amount for the next 8 h. The expression level of active caspase3 is significantly different between the Saos2 cells treated with L-1P and D-1P. Active caspase3 changes little following L-1P treatment of the Saos2 cells, but it increases about 1.7 fold over the first 3 h following treatment with D-1P, and then decreases to a relatively constant amount that is same as the untreated cells. Interestingly, the expression of active-PARP or Bad remains almost constant in the treatment of L-1P (or D-1P), while the expression level of phosphorylated Bad increases to the highest at the incubation time of 3 h, and drops quickly with the extended time incubation. Since Bad is a proapoptotic member of the Bcl-2 family (Yang et al., *Cell*, 80:285 (1995), which is hereby incorporated by reference in its entirety), the decreased expression level of phosphorylated Bad indicates that Bad is activated by dephosphorylation under stress, which then activates the apoptotic effector machinery, and triggers the release of Cytochrome c from mitochondria to the cytosol (Tan et al., *J. Biol. Chem.* 275:25865 (2000); Eskes et al., *J. Cell Biol.* 143:217 (1998); Shimizu et al., *Nature* 399:483 (1999), which are hereby incorporated by reference in their entirety) (vide infra).

Example 9—Release of Cytochrome c (Cyt c) to the Cytosol

Figure 18:
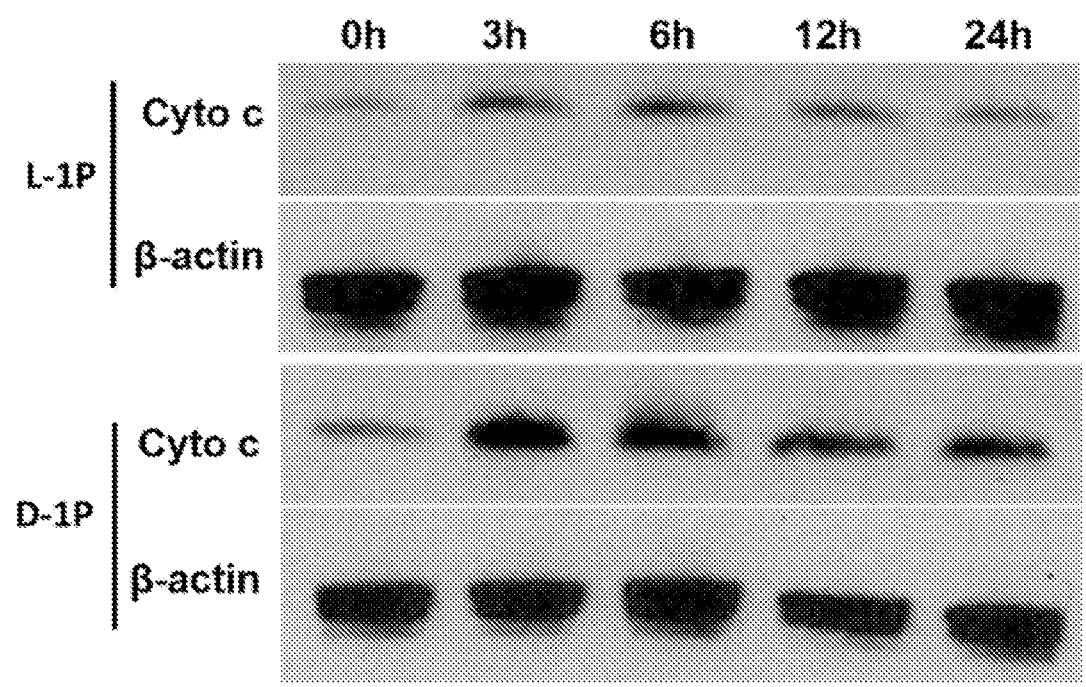
FIG. 18 shows a time-dependent Western blot analysis of cytochrome c (cyt c) from the cytosolic fraction of Saos2 cell treated with L-1P or D-1P (50 μM).

Based on the CLSM experiment (Example 4; FIG. 12), which indicates that L-1P (D-1P) can interact with and enrich in the cellular mitochondria, and that the modality of cell death (FIGS. 16 and 17) depends on intrinsic apoptosis to some extent, it was believed that the cell death induced by L-1P (or D-1P) involves the release of Cytochrome c ("Cyt c"), an essential component of the mitochondrial respiratory chain (Green et al., *Science* 281:1309 (1998); Kroemer et al., *Nat. Med.* 6 (2000), which are hereby incorporated by reference in their entirety), from the mitochondria to the cytosol. To confirm this belief, the cytosol from the Saos2 cells was prepared according to an established method (Dopp et al., *Drug Metab. Dispos.* 36:971 (2008), which is hereby incorporated by reference in its entirety) in the presence of 50 µM of L-1P (or D-1P) and time-dependent Western blot was used to detect the expression levels of Cyt c at different incubation times. As shown in FIG. 18, the Cyt c in the cytosol significantly increases over the first 6 h in the presence of L-1P (or D-1P), and remains in the cytosol over the 24 h test period. Moreover, the expression level of Cyt c in the presence of D-1P is higher than in the presence of L-1P, indicating D-1P is more efficient than L-1P for modulating the homeostasis of mitochondria on Saos2 cells. This result agrees with the relative cytotoxicity of L-1P and D-1P, (FIG. 7). As a control, the whole cell fraction of Saos2 cells treated with L-1P (or D-1P), containing both cytosol and mitochondria was also prepared. The time-dependent Western blot indicates that the Cyt c in the fraction of whole cell remains constant. These results indicate that assemblies of L-1 (or D-1), formed by EISA, result in dysfunction of mitochondria of the Saos2 cells, which release Cyt c to the cytosol to activate the caspase cascade signaling pathway, thus triggering intrinsic apoptosis of the Saos2 cells (Kluck et al., *Science* 275:1132 (1997); Yang et al., *Science* 275:1129 (1997), which are hereby incorporated by reference in their entirety) as one of the modes of the death of the Saos2 cells.

Example 10—L-1P (or D-1P) Causes No Acquired Drug Resistance

Figure 19:
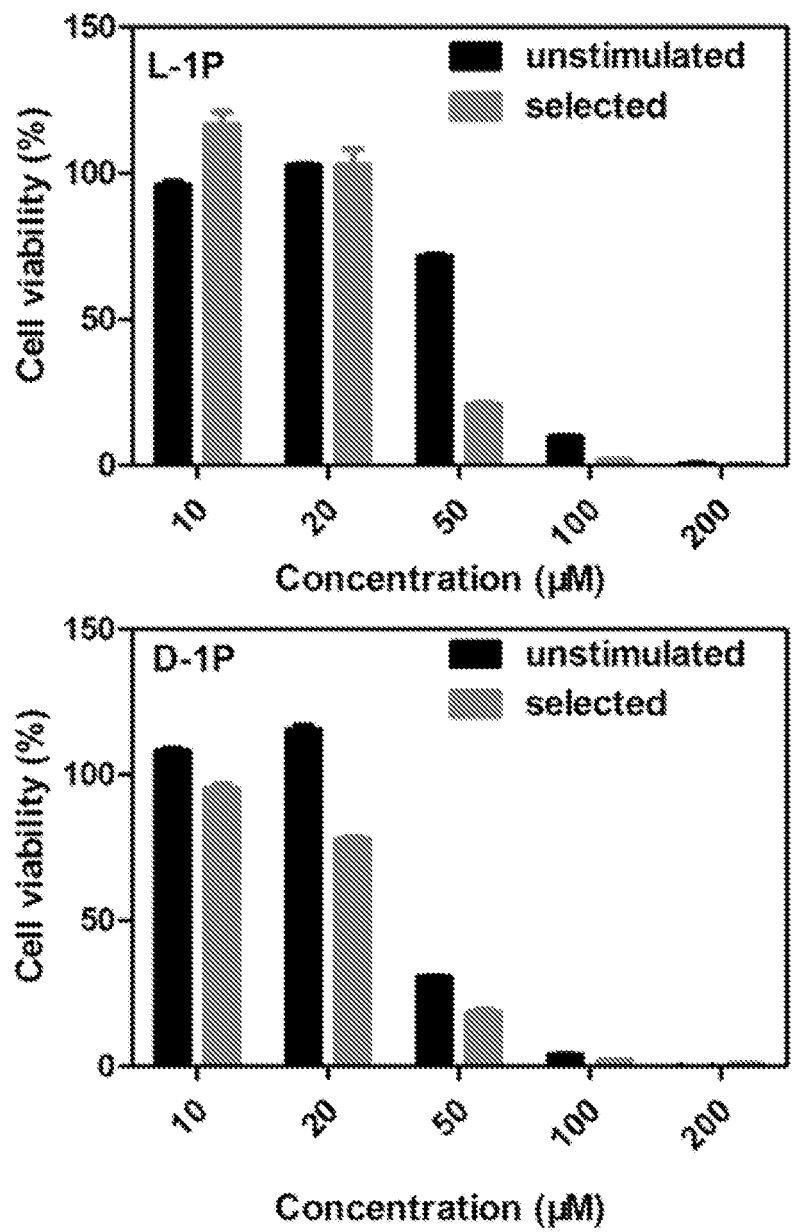
FIG. 19 shows cell viability of unstimulated Saos2 cell line or selected Saos2 cell line (after five weeks treatment of the precursors with gradually increase concentrations) incubated with L-1P or D-1P at different concentrations for 48 h. The concentration for treating cells started from 10 μM and then changed to 15 μM, 20 μM, 25 μM, 30 μM, 35 μM, 40 μM, 45 μM, and 50 μM.

Based on the above mechanism of cell death showing that L-1P (or D-1P) activates multiple death signaling pathways, it is believed that cancer cells unlikely would be able to evolve resistance toward this multiple targeting strategy. Moreover, the assemblies of L-1 (or D-1), unlike traditional small molecule inhibitors, are plastic (i.e., exhibiting polymorphism). Such a plasticity should minimize the path to drug resistance. Thus, it was examined whether Saos2 cells can evolve acquired resistance after being repeatedly stimulated by L-1P (or D-1P) at suboptimal concentrations, which is an established method to select drug resistant cancer cells (Cillo et al., *Cancer Res.* 47:2604 (1987); Riganti et al., *Cancer Res.* 65:516 (2005); Riganti et al., *J. Natl. Cancer Inst.* 107:djv046 (2015), which are hereby incorporated by reference in their entirety). The precursors were incubated with Saos2 cells by gradually increasing the concentration of L-1P (or D-1P) from 10 to 50 µM for five weeks and selecting the cells that survive treatment. After that, the selected Saos2 cells were tested with L-1P (or D-1P) by MTT assay. As shown in FIG. 19, the $IC_{50}$ of L-1P against Saos2 cells (after five weeks stimulation of L-1P) is 36.8 µNI for 48 h, and the $IC_{50}$ of D-1P is 35.2 µM against Saos2 cells (after five weeks stimulation of D-1P), which is similar with the previous results of cytotoxicities of the D-1P on the unstimulated Saos2 cells. Surprisingly, the repeated stimulation of Saos2 cells significantly sensitizes the Saos2 cells to the assemblies of L-1: at 50 µM of L-1P, the cell viability of unstimulated Saos2 is 71.7%, but it drops to 20.5% for the selected cells. While this observation deserves further mechanistic exploration, these preliminary results undoubtedly indicate that multiple targeting (cell and subcellular targetings) is a promising strategy for minimizing acquired drug resistance. Since one of the biggest challenges in cancer therapy and drug discovery is drug resistance (Ford et al., *Pharmacol. Rev.* 42:155 (1990); Dean et al. *Nat. Rev.*

Cancer 5:275 (2005); Brown et al., *Cancer Res.* 58:1408 (1998), which are hereby incorporated by reference in their entirety), this result indicates that combining EISA with other targeting strategies to generate anticancer supramolecular assemblies promises a fundamentally new direction for anticancer drug discovery.

Discussion of Examples 1-10

To achieve multi-targeting, high selectivity, and minimal drug resistance, a combination of mitochondria targeting with cell targeting was utilized. TPP was used for mitochondria targeting and enzyme-instructed self-assembly (EISA) was used for cell targeting. As a bioinspired (Whitesides, G. M., *Interface Focus* (2015), which is hereby incorporated by reference in its entirety), multiple step molecular process (Zhou et al., *Bioconjugate Chem.* 26:987 (2015); Zhou et al., *Chem* 1:246 (2016), which are hereby incorporated by reference in their entirety) that integrates enzymatic reaction and self-assembly (Yang et al., *Acc. Chem. Res.* 41:315 (2008); Li et al., *Angew. Chem., Int. Ed.* 50:9365 (2011); Li et al., *J. Am. Chem. Soc.* 133:17513 (2011); Yang et al., *Soft Matter* 5:2546 (2009); Zhou et al., *J. Am. Chem. Soc.* 138:3813 (2016), which are hereby incorporated by reference in their entirety), EISA is emerging as a promising strategy for targeting cancer cells (Yang et al., Adv. Mater. 19:3152 (2007); Pires et al., *J. Am. Chem. Soc.* 137:576 (2015); Tanaka et al., *J. Am. Chem. Soc.* 137:770 (2015); Huang et al., *ACS Nano* 9:9517 (2015), which are hereby incorporated by reference in their entirety). Specifically, TPP was conjugated with a peptide derivative that undergoes EISA. The peptide includes a self-assembling motif as the backbone, phosphorylated on a tyrosine residue and capped at the N-terminus by a fluorophore. Attaching TPP to the ε-amine of a lysine residue on the peptide forms the precursors (L-1P and D-1P), while replacing TPP by acetyl at the ε-position generates control peptides L-2P and D-2P. Upon dephosphorylation of the precursors by alkali phosphatase (ALP), the resulting products self-assemble to form nanoscale assemblies via non-covalent interactions, as evidenced by static light scattering (SLS) and transition electron microscopy (TEM).

Most importantly, L-1P or D-1P selectively kill human osteosarcoma cells (Saos2), while being innocuous to normal cell (HS5). D-1P, being more stable inside cells, is more potent than L-1P. L-2P or D-2P, even at ten times concentration of L-1P or D-1P, shows no toxicity to Saos2 cells, confirming cytotoxicity from the TPP. Moreover, Saos2 cells, being incubated with L-1P (or D-1P) for five weeks by a stepwise increase the concentrations of L-1P (or D-1P), shows little acquired drug resistance to L-1P or (D-1P). Unexpectedly, the treated cells become more sensitive to the assemblies of TPP. The preliminary mechanistic study reveals that L-1 or D-1, after being generated via in-situ dephosphorylation of L-1P or D-1P, respectively, are taken-up by the cancer cells (mainly via caveolae/raft dependent endocytosis, plus clathrin-mediated endocytosis in some extent), and after escaping from lysosome localize on mitochondria. The assemblies of L-1 or D-1 disrupt the homeostasis of mitochondria, triggering the release Cyt c, and activation of caspase cascade (Liu et al., *Cell* 86:147 (1996); Li et al., *Cell* 91:479 (1997), which are hereby incorporated by reference in their entirety), to result in cancer cell death. As the first case of integration of cell and subcellular targeting processes, this work demonstrates a new strategy to selectively kill cancer cells via targeting an organelle in a cell-specific manner. Moreover, this work illustrates a new way for the uptake of self-assembled short peptides and the effective release of the load from endosomes and lysosomes, which can be useful for designing enzyme-instructed systems to promote the endocytosis of drug candidates that fails due to poor cell uptake.

This report is believed to be the first case of integrating cell and subcellular targeting of therapeutic agents for selectively killing cancer cells without causing acquired drug resistance. By rationally designing the precursors to contain a peptide segment of EISA and a mitochondria targeting motif, testing the precursors in cell assays, and preliminarily examining the mechanisms of cellular uptake and cell death, the use of molecular processes for both cell and subcellular targeting is validated. Moreover, stimulating the Saos2 cells by the precursors hardly induces acquired resistance. As anticancer drug resistance remains the challenge for most modern drug discovery and the reason for the failure of most clinical drugs (e.g., cisplatin, doxorubicin (Hamilton et al., *Biochem. Pharmacol.* 34:2583 (1985); Gottesman, M. M., *Annu. Rev. Med.* 53:615 (2002), which are hereby incorporated by reference in their entirety)), the strategy demonstrated in the preceding Examples promises more profound impact than just killing the Saos2 cells. In addition, the use of the enantiomer pairs (i.e., L-1P and D-1P) to treat the same set of cells, undoubtedly, validates the molecular processes and targets involving in the cell death of the cancer cells. The concept demonstrated here should be applicable to the design of other the precursors as the substrates of other enzymes overexpressed by cancer cells (Hirst et al., *Nat. Chem.* 2:1089 (2010); Komatsu et al., *Angew. Chem., Int. Ed.* 53:3993 (2014), which are hereby incorporated by reference in their entirety) (e.g., CD73 (Wu et al., *J. Colloid Interface Sci.* 447:269 (2015), which is hereby incorporated by reference in its entirety), MMP9 (Yang et al., *Soft Matter* 5:2546 (2009); Kalafatovic et al., *Biomater. Sci.* 3:246 (2015); Lin et al., *Biomacromolecules* 15:1419 (2014); Huang et al., *Pept. Sci.* 100:790 (2013), which are hereby incorporated by reference in their entirety), and furin (Liang et al., *Nat. Chem.* 2:54 (2010); Ye et al., *Nat. Chem.* 6:519 (2014); Miao et al., *Chem. Commun.* 48:9738 (2012), which are hereby incorporated by reference in their entirety)) and other subcellular organelle (Ferri et al., *Nat. Cell Biol.* 3:E255 (2001); Kiyonaka et al., *Nature Methods* 10:1232 (2013); Ishida et al., *J. Am. Chem. Soc.* 135:12684 (2013), which are hereby incorporated by reference in their entirety). Although the concentration required for killing cells is higher than current clinical standard based on highly potent yet unselective drugs (e.g., cisplatin), the exceptional selectivity exhibited by the precursors (i.e., L-1P ad D-1P) should achieve acceptable therapeutic index. Currently, the molecules are being engineered for achieve high activity against cancer cells and tuning the distribution of bioactive molecules (Feng et al., *Chem. Commun.* 52:6332 (2016), which is hereby incorporated by reference in its entirety).

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. A peptide-redox modulator conjugate comprising a peptide that comprises the amino acid sequence of FFKY (SEQ ID NO: 51) or FFYK (SEQ ID NO: 50), optionally up to 20 amino acids in total, wherein the tyrosine residue is phosphorylated and the N-terminal amino acid is covalently bound to an arylacyl capping moiety, and a redox modulator conjugated to a sidechain of a lysine residue present in SEQ ID NO: 50 or SEQ ID NO: 51.

2. The peptide-redox modulator conjugate according to claim 1, wherein, upon exposure to a cell that expresses an ectoenzyme that hydrolyzes the phosphate group, the peptide self-assembles to form nanofibrils externally of the cell.

3. The peptide-redox modulator conjugate according to claim 1, wherein the peptide includes one or more additional aromatic amino acid residues selected from the group consisting of phenyalanine, phenylalanine derivatives, napthylalanine, napthylalanine derivative, tyrosine, and tyrosine derivatives.

4. The peptide-redox modulator conjugate according to claim 1, wherein the amino acids ae al D-amino acids or al L-amino acids.

5. The peptide-redox modulator conjugate according to claim 1, wherein the peptide further Includes an additional phosphorylated residue selected from the group of phosphoserine, phosphothreonine, phosphotyrosine, and phosphohistidine.

6. The peptide-redox modulator conjugate according to claim 1, wherein said peptide is resistant to a protease.

7. The peptide-redox modulator conjugate according to claim 1, wherein the arylacyl capping moiety Is selected from 2-naphthalacetyl, phenylacetyl, fluorenyl-9-methoxycarbonyl, pyrenylbutanoyl, cinnamoyl and 3-((7-nitrobenzo(c)-1,2,5-oxadiazol-4-yl)amino)proprionyl.

8. The peptide-redox modulator conjugate according to claim 1, wherein said peptide Is between 4 to 10 amino acids.

9. The peptide-redox modulator conjugate according to claim 1, wherein the redox modulator Is triphenyl phosphonium, a substituted phthalazinedione, substituted N,N'-diethylaminotriphenylmethane or a porphyrin.

10. A supermolecular hydrogel formed upon self-assembly of a hydrolytic product of the peptide-redox modulator conjugate according to claim 1.

11. A pharmaceutical composition comprising a pharmaceutically acceptable carrier and a peptide-redox modulator conjugate according to claim 1.

12. The pharmaceutical composition according to claim 11 wherein the carrier is an aqueous medium.

13. The pharmaceutical composition according to claim 11, wherein the peptide-redox modulator conjugate is present at a concentration of about 1 µM to about 10 mM.

14. The peptide-redox modulator conjugate according to claim 1, wherein the arylacyl capping moiety is 2-naphthylacetyl or 3-((7-nitrobenzo(c)-1,2,5-oxadiazol-4-yl)amino) proprionyl and said peptide is up to 10 amino acids in length.

15. A peptide-redox modulator conjugate selected from the group consisting of:
  Naphthyl-acetyl-NH-D-Phe-D-Phe-D-Tyr(phospho)-D-Lys(TPP)-COOH,
  Naphthyl-acetyl-NH-D-Phe-D-Phe-D-Lys(TPP)-D-Tyr(phospho)-COOH,
  Naphthyl-acetyl-NH-L-Phe-L-Phe-L-Tyr(phospho)-L-Lys(TPP)-COOH (SEQ ID NO:2),
  Naphthyl-acetyl-NH-L-Phe-L-Phe-L-Lys(TPP)-L-Tyr(phospho)-COOH (SEQ ID NO:3),
  NBD-proprionyl-NH-D-Phe-D-Phe-D-Tyr(phospho)-D-Lys(TPP)-COOH,
  NBD-proprionyl-NH-D-Phe-D-Phe-D-Lys(TPP)-D-Tyr(phospho)-COOH,
  NBD-proprionyl-NH-L-Phe-L-Phe-L-Tyr(phospho)-L-Lys(TPP)-COOH (SEQ ID NO: 4),
  NBD-proprionyl-NH-L-Phe-L-Phe-L-Lys(TPP)-L-Tyr(phospho)-COOH (SEQ ID NO: 5),
  Naphthyl-acetyl-NH-D-Phe-D-Phe-D-Tyr(phospha)-D-Lys(phthalazinedione)-COOH,
  Naphthyl-acetyl-NH-D-Phe-D-Phe-D-Lys(phthazinedione)-D-Tyr(phospho)-COOH,
  Naphthyl-acetyl-NH-L-Phe-L-Phe-L-Tyr(phospho)-L-Lys(phthalazinedione)-COOH (SEQ ID NO: 6),
  Naptyl-acetyl-NH-L-Phe-L-Phe-L-Lys(phthalazinedone)-L-Tyr(phospho)-COOH (SEQ ID NO: 7),
  NBD-acetyl-NH-D-Phe-D-Phe-D-Tyr(phospho)-D-Lys(phthalazinedone)-COOH,
  NBD-acetyl-NH-D-Phe-D-Phe-D-Lys(phthamzinedone)-D-Tyr(phospho)-COOH,
  NBD-acetyl-NH-L-Phe-L-Phe-L-Tyr(phospho)-L-Lys(phthalazinedone)-COOH (SEQ ID NO: 8),
  NBD-acetyl-NH-L-Phe-L-Phe-L-Lys(phtainedione)-L-Tyr(phospho)-COOH (SEQ ID NO: 9),
  Naphthyl-acetyl-NH-D-Phe-D-Phe-D-Tyr(phospho)-D-Lys(DEATPM)-COOH,
  Naphthyl-acetyl-NH-D-Phe-D-Phe-D-Lys(DEATPM)-D-Tyr(phospho)-COOH,
  Naphthyl-acetyl-NH-L-Phe-L-Phe-L-Tyr(phospho)-L-Lys(DEATPM)-COOH (SEQ ID NO: 10),
  Naphthyl-acetyl-NH-L-Phe-L-Phe-L-Lys(DEATPM)-L-Tyr(phospho)-COOH (SEQ ID NO: 11),
  NBD-acetyl-NH-D-Phe-D-Phe-D-Tyr(phospho)-D-Lys(DEATPM)-COOH,
  NBD-acetyl-NH-D-Phe-D-Phe-D-Lys(DEATPM)-D-Tyr(phospho)-COOH,
  NBD-acetyl-NH-L-Phe-L-Phe-L-Tyr(phospho)-L-Lys(DEATPM)-COOH (SEQ ID NO: 12),
  NBD-acetyl-NH-L-Phe-L-Phe-L-Lys(DEATPM)-L-Tyr(phospho)-COOH (SEQ ID NO: 13),
  Naphthyl-acetyl-NH-D-Phe-D-Phe-D-Tyr(phospho)-D-Lys(porphyrin)-COOH,
  Naphthyl-acetyl-NH-D-Phe-D-Phe-D-Lys(porphyrin)-D-Tyr(phospho)-COOH,
  Naphthyl-acetyl-NH-L-Phe-L-Phe-L-Tyr(phospho)-L-Lys(porphyrin)-COOH (SEQ ID NO: 14),
  Naphthyl-acetyl-NH-L-Phe-L-Phe-L-Lys(porphyin)-L-Tyr(phospho)-COOH (SEQ ID NO: 15),
  NBD-proprionyl-NH-D-Phe-D-Phe-D-Tyr(phospho)-D-Lys(porphyrin)-COOH,
  NBD-proprionyl-NH-D-Phe-D-Phe-D-Lys(porphyin)-D-Tyr(phospho)-COOH,
  NBD-proprionyl-NH-L-Phe-L-Phe-L-Tyr(phospho)-L-Lys(porphyrin)-COOH (SEQ ID NO: 16),
  NBD-proprionyl-NH-L-Phe-L-Phe-L-Lys(porphyin)-L-Tyr(phospho)-COOH (SEQ ID NO: 17),
  Naphthyl-acetyl-NH-D-Phe-D-Phe-D-Tyr-D-Lys(porphyrin)-di(isopropyloxycarbonyloxymethyl)phosphoester,
  Naphthyl-acetyl-NH-D-Phe-D-Phe-D-Lys(porphyrin)-D-Tyr-di(isopropyloxycarbonyloxymethyl)phosphoester,
  Naphthyl-acetyl-NH-L-Phe-L-Phe-L-Tyr-L-Lys(porphyrin)-di(isopropyloxycarbonyloxymethyl)phosphoester (SEQ ID NO: 18),
  Naphthyl-acetyl-NH-L-Phe-L-Phe-L-Lys(porphyrin)-L-Tyr-di(isopropyloxycarbonyloxymethyl)phosphoester (SEQ ID NO: 19),
  NBD-acetyl-NH-D-Phe-D-Phe-D-Tyr-D-Lys(porphyrin)-di(isopropyloxycarbonyloxymethyl)phosphoester,
  NBD-acetyl-NH-D-Phe-D-Phe-D-Lys(porphyrin)-D-Tyr-di(isopropyloxycarbonyloxymethyl)phosphoester,
  NBD-acetyl-NH-L-Phe-L-Phe-L-Tyr-L-Lys(porphyrin)-di(isopropyloxycarbonyloxymethyl)phosphoester (SEQ ID NO: 20),
  NBD-acetyl-NH-L-Phe-L-Phe-L-Lys(porphyrin)-L-Tyr-di(isopropyloxycarbonyloxymethyl)phosphoester (SEQ ID NO: 21),
  Naphthyl-acetyl-NH-D-Phe-D-Phe-D-Tyr-D-Lys(TPP)-di(isopropyloxycarbonyloxymethyl)phosphoester,
  Naphthyl-acetyl-NH-D-Phe-D-Phe-D-Lys(TPP)-D-Tyr-di(isopropyloxycarbonyloxymethyl)phosphoester, Naphthyl-acetyl-NH-L-Phe-L-Phe-L-Tyr-L-Lys(TPP)-di(isopropyloxycarbonyloxymethyl)phosphoester (SEQ ID NO: 22), Naphthyl-acetyl-NH-L-Phe-L-Phe-L-Lys(TPP)-L-Tyr-di(isopropyloxycarbonyloxymethyl)phosphoester (SEQ ID NO: 23), NBD-acetyl-NH-D-Phe-D-Phe-D-Tyr-D-Lys(TPP)-di(isopropyloxycarbonyloxymethyl)phosphoester, NBD-acetyl-NH-D-Phe-D-Phe-D-Lys(TPP)-D-Tyr-di(isopropyloxycarbonyloxymethyl)phosphoester, NBD-acetyl-NH-L-Phe-L-Phe-L-Tyr-L-Lys(TPP)-di(isopropyloxycarbonyloxymethyl)phosphoester (SEQ ID NO: 24), NBD-acetyl-NH-L-Phe-L-Phe-L-Lys(TPP)-L-Tyr-di(isopropyloxycarbonyloxymethyl)phosphoester (SEQ ID NO: 25), Naphthyl-acetyl-NH-D-Phe-D-Phe-D-Tyr-D-Lys(TPP)-di(isopropyloxycarbonyloxymethyl)phosphoester, Naphthyl-acetyl-NH-D-Phe-D-Phe-D-Lys(phthalazinedione)-D-Tyr-di(isopropyloxycarbonyloxymethyl)phosphoester, Naphthyl-acetyl-NH-L-Phe-L-Phe-L-Tyr-L-Lys(phthalazinedione)-di(isopropyloxycarbonyloxymethyl)phosphoester (SEQ ID NO: 26), Naphthyl-acetyl-NH-L-Phe-L-Phe-L-Lys(phthalazinedione)-L-Tyr-di(isopropyloxycarbonyloxymethyl)phosphoester (SEQ ID NO: 27), NBD-acetyl-NH-D-Phe-D-Phe-D-Tyr-D-Lys(phthalazinedione)-di(isopropyloxycarbonyloxymethyl)phosphoester, NBD-acetyl-NH-D-Phe-D-Phe-D-Lys(phthalazinedione)-D-Tyr-di(isopropyloxycarbonyloxymethyl)phosphoester, NBD-acetyl-NH-L-Phe-L-Phe-L-Tyr-L-Lys(phthalazinedione)-di(isopropyloxycarbonyloxymethyl)phosphoester (SEQ ID NO: 28), NBD-acetyl-NH-L-Phe-L-Phe-L-Lys(phthalazinedione)-L-Tyr-di(isopropyloxycarbonyloxymethyl)phosphoester (SEQ ID NO: 29), Naphthyl-acetyl-NH-D-Phe-D-Phe-D-Tyr-D-Lys(DEATPM)-di(isopropyloxycarbonyloxymethyl)phosphoester, Naphthyl-acetyl-NH-D-Phe-D-Phe-D-Lys(DEATPM)-D-Tyr-di(isopropyloxycarbonyloxymethyl)phosphoester, Naphthyl-acetyl-NH-L-Phe-L-Phe-L-Tyr-L-Lys(DEATPM)-di(isopropyloxycarbonyloxymethyl)phosphoester (SEQ ID NO: 30), Naphthyl-acetyl-NH-L-Phe-L-Phe-L-Lys(DEATPM)-L-Tyr-di(isopropyloxycarbonyloxymethyl)phosphoester (SEQ ID NO: 31), NBD-acetyl-NH-D-Phe-D-Phe-D-Tyr-D-Lys(DEATPM)-di(isopropyloxycarbonyloxymethyl)phosphoester, NBD-acetyl-NH-D-Phe-D-Phe-D-Lys(DEATPM)-D-Tyr-di(isopropyloxycarbonyloxymethyl)phosphoester, NBD-acetyl-NH-L-Phe-L-Phe-L-Tyr-L-Lys(DEATPM)-di(isopropyloxycarbonyloxymethyl)phosphoester (SEQ ID NO: 32), NBD-acetyl-NH-L-Phe-L-Phe-L-Lys(DEATPM)-L-Tyr-di(isopropyloxycarbonyloxymethyl)phosphoester (SEQ ID NO: 33), and Naphthyl-acetyl-NH-D-Phe-D-Phe-D-Tyr-D-Lys(DEATPM)-di(isopropyloxycarbonyloxymethyl)phosphoester, where NBD is a (7-nitro-1,2,5-benzoxadiazolyl amino) proprionyl group.

16. A product formed by exposing the peptide-redox modulator conjugate of claim 1 to an enzyme that hydrolyzes the phosphate group, wherein the peptide is dephosphorylated.

17. The product according to claim 16, wherein the product is selected from the group consisting of:

Naphthyl-acetyl-NH-D-Phe-D-Phe-D-Tyr-D-Lys(TPP)-COOH,

Naphthyl-acetyl-NH-D-Phe-D-Phe-D-Lys(TPP)-D-Tyr-COOH,

Naphthyl-acetyl-NH-L-Phe-L-Phe-L-Tyr-L-Lys(TPP)-COOH (SEQ ID NO: 34),

Naphthyl-acetyl-NH-L-Phe-L-Phe-L-Lys(TPP)-L-Tyr-COOH (SEQ ID NO: 35),

NBD-acetyl-NH-D-Phe-D-Phe-D-Tyr-D-Lys(TPP)-COOH,

NBD-acetyl-NH-D-Phe-D-Phe-D-Lys(TPP)-D-Tyr-COOH,

NBD-acetyl-NH-L-Phe-L-Phe-L-Tyr-L-Lys(TPP)-COOH (SEQ ID NO: 36),

NBD-acetyl-NH-L-Phe-L-Phe-L-Lys(TPP)-L-Tyr-COOH (SEQ ID NO: 37),

Naphthyl-acetyl-NH-D-Phe-D-Phe-D-Tyr-D-Lys(phthalazinedione)-COOH,

Naphthyl-acetyl-NH-D-Phe-D-Phe-D-Lys(phthalazinedione)-D-Tyr-COOH,

Naphthyl-acetyl-NH-L-Phe-L-Phe-L-Tyr-L-Lys(phthalazinedione)-COOH (SEQ ID NO: 38), Naphthyl-acetyl-NH-L-Phe-L-Phe-L-Lys(phthalazinedione)-L-Tyr-COOH (SEQ ID NO: 39), NBD-acetyl-NH-D-Phe-D-Phe-D-Tyr-D-Lys(phthalazinedione)-COOH, NBD-acetyl-NH-D-Phe-D-Phe-D-Lys(phthalazinedione)-D-Tyr-COOH, NBD-acetyl-NH-L-Phe-L-Phe-L-Tyr-L-Lys(phthalazinedione)-COOH (SEQ ID NO: 40), NBD-acetyl-NH-L-Phe-L-Phe-L-Lys(phthalazinedione)-L-Tyr-COOH (SEQ ID NO: 41), Naphthyl-acetyl-NH-D-Phe-D-Phe-D-Tyr-D-Lys(DEATPM)-COOH, Naphthyl-acetyl-NH-D-Phe-D-Phe-D-Lys(DEATPM)-D-Tyr-COOH, Naphthyl-acetyl-NH-L-Phe-L-Phe-L-Tyr-L-Lys(DEATPM)-COOH (SEQ ID NO: 42), Naphthyl-acetyl-NH-L-Phe-L-Phe-L-Lys(DEATPM)-L-Tyr-COOH (SEQ ID NO: 43), NBD-acetyl-NH-D-Phe-D-Phe-D-Tyr-D-Lys(DEATPM)-COOH, NBD-acetyl-NH-D-Phe-D-Phe-D-Lys(DEATPM)-D-Tyr-COOH, NBD-acetyl-NH-L-Phe-L-Phe-L-Tyr-L-Lys(DEATPM)-COOH (SEQ ID NO: 44), NBD-acetyl-NH-L-Phe-L-Phe-L-Lys(DEATPM)-L-Tyr-COOH (SEQ ID NO:45), Naphthyl-acetyl-NH-D-Phe-D-Phe-D-Tyr-D-Lys(porphyrin)-COOH, Naphthyl-acetyl-NH-D-Phe-D-Phe-D-Lys(porphyrin)-D-Tyr-COOH, Naphthyl-acetyl-NH-L-Phe-L-Phe-L-Tyr-L-Lys(porphyrin)-COOH (SEQ ID NO: 46), Naphthyl-acetyl-NH-L-Phe-L-Phe-L-Lys(porphyrin)-L-Tyr-COOH (SEQ ID NO: 47), NBD-proprionyl-NH-D-Phe-D-Phe-D-Tyr-D-Lys(porphyrin)-COOH, NBD-proprionyl-NH-D-Phe-D-Phe-D-Lys(porphyrin)-D-Tyr-COOH, NBD-proprionyl-NH-L-Phe-L-Phe-L-Tyr-L-Lys(porphyrin)-COOH (SEQ ID NO: 48), and
NBD-proprionyl-NH-L-Phe-L-Phe-L-Lys(porphyrin)-L-Tyr-COOH (SEQ ID NO: 49),
where NBD is a (7-nitro-1,2,5-benzoxadiazolyl amino) proprionyl group.

18. A supermolecular hydrogel formed upon self-assembly of the product of claim 16.

* * * * *

UNITED STATES PATENT AND TRADEMARK OFFICE
CERTIFICATE OF CORRECTION

PATENT NO.        : 12,246,068 B2
APPLICATION NO.   : 16/476183
DATED             : March 11, 2025
INVENTOR(S)       : Xu et al.

It is certified that error appears in the above-identified patent and that said Letters Patent is hereby corrected as shown below:

In the Claims

At Claim 4, Column 71, Line 8, please delete "ae al" and insert --are all-- in its place.

At Claim 4, Column 71, Line 8, please delete "al" and insert --all-- in its place.

At Claim 5, Column 71, Line 11, please delete "Includes" and insert --includes-- in its place.

At Claim 7, Column 71, Line 18, please delete "Is" and insert --is-- in its place.

At Claim 8, Column 71, Line 23, please delete "Is" and insert --is-- in its place.

At Claim 9, Column 71, Line 26, please delete "Is" and insert --is-- in its place.

At Claim 15, Column 71, Lines 62-63, please delete "Naphthyl-acetyl-NH-D-Phe-D-Phe-D-Tyr(phospha)-D-Lys(phthalazinedione)-COOH" and insert --Naphthyl-acetyl-NH-D-Phe-D-Phe-D-Tyr(phospho)-D-Lys(phthalazinedione)-COOH-- in its place.

At Claim 15, Column 71, Lines 64-65, please delete "Naphthyl-acetyl-NH-D-Phe-D-Phe-D-Lys(phthazinedione)-D-Tyr(phospho)-COOH" and insert --Naphthyl-acetyl-NH-D-Phe-D-Phe-D-Lys(phthalazinedione)-D-Tyr(phospho)-COOH-- in its place.

At Claim 15, Column 72, Lines 1-2, please delete "Naptyl-acetyl-NH-L-Phe-L-Phe-L-Lys(phthalazinedone)-L-Tyr(phospho)-COOH" and insert --Naphthyl-acetyl-NH-L-Phe-L-Phe-L-Lys(phthalazinedione)-L-Tyr(phospho)-COOH-- in its place.

At Claim 15, Column 72, Lines 3-4, please delete "NBD-acetyl-NH-D-Phe-D-Phe-D-Tyr(phospho)-D-Lys(phthalazinedone)-COOH" and insert --NBD-acetyl-NH-D-Phe-D-Phe-D-Tyr(phospho)-D-Lys(phthalazinedione)-COOH-- in its place.

Signed and Sealed this
Thirteenth Day of May, 2025

Coke Morgan Stewart
*Acting Director of the United States Patent and Trademark Office*

CERTIFICATE OF CORRECTION (continued)
U.S. Pat. No. 12,246,068 B2

At Claim 15, Column 72, Lines 5-6, please delete "NBD-acetyl-NH-D-Phe-D-Phe-D-Lys(phthamzinedone)-D-Tyr(phospho)-COOH" and insert --NBD-acetyl-NH-D-Phe-D-Phe-D-Lys(phthalazinedione)-D-Tyr(phospho)-COOH-- in its place.

At Claim 15, Column 72, Lines 7-8, please delete "NBD-acetyl-NH-L-Phe-L-Phe-L-Tyr(phospho)-L-Lys(phthalazinedone)-COOH" and insert --NBD-acetyl-NH-L-Phe-L-Phe-L-Tyr(phospho)-L-Lys(phthalazinedione)-COOH-- in its place.

At Claim 15, Column 72, Lines 9-10, please delete "NBD-acetyl-NH-L-Phe-L-Phe-L-Lys(phtainedione)-L-Tyr(phospho)-COOH" and insert --NBD-acetyl-NH-L-Phe-L-Phe-L-Lys(phthalazinedione)-L-Tyr(phospho)-COOH-- in its place.

At Claim 15, Column 72, Lines 33-34, please delete "Naphthyl-acetyl-NH-L-Phe-L-Phe-L-Lys(porphyin)-L-Tyr(phospho)-COOH" and insert --Naphthyl-acetyl-NH-L-Phe-L-Phe-L-Lys(porphyrin)-L-Tyr(phospho)-COOH-- in its place.

At Claim 15, Column 72, Lines 37-38, please delete "NBD-proprionyl-NH-D-Phe-D-Phe-D-Lys(porphyin)-D-Tyr(phospho)-COOH" and insert --NBD-proprionyl-NH-D-Phe-D-Phe-D-Lys(porphyrin)-D-Tyr(phospho)-COOH-- in its place.